United States Patent
Mourad et al.

(10) Patent No.: US 7,547,283 B2
(45) Date of Patent: *Jun. 16, 2009

(54) METHODS FOR DETERMINING INTRACRANIAL PRESSURE NON-INVASIVELY

(75) Inventors: Pierre D. Mourad, Seattle, WA (US); Brandt Mohr, Seattle, WA (US); Michel Kliot, Bellevue, WA (US); Robert C. A. Frederickson, Victoria (CA)

(73) Assignee: PhysioSonics, Inc., Seattle, WA (US)

( * ) Notice: Subject to any disclaimer, the term of this patent is extended or adjusted under 35 U.S.C. 154(b) by 615 days.

This patent is subject to a terminal disclaimer.

(21) Appl. No.: 10/861,197

(22) Filed: Jun. 3, 2004

(65) Prior Publication Data

US 2005/0015009 A1  Jan. 20, 2005

Related U.S. Application Data

(63) Continuation-in-part of application No. 09/995,897, filed on Nov. 28, 2001, now Pat. No. 6,875,176.

(60) Provisional application No. 60/508,836, filed on Oct. 1, 2003, provisional application No. 60/475,803, filed on Jun. 3, 2003, provisional application No. 60/253,959, filed on Nov. 28, 2000.

(51) Int. Cl.
*A61B 8/14* (2006.01)

(52) U.S. Cl. .................................... 600/459
(58) Field of Classification Search .......... 600/407–480
See application file for complete search history.

(56) References Cited

U.S. PATENT DOCUMENTS 3,872,858 A    3/1975 Hudson et al.

(Continued)

FOREIGN PATENT DOCUMENTS

WO        98/49934 A1    11/1998

(Continued)

OTHER PUBLICATIONS

Czosnyka, Marek, et al., "Monitoring of Cerebral Autoregulation in Head-Injured Patients," *Stroke*, vol. 27, No. 10, pp. 1829-1834 (Oct. 1996).

(Continued)

*Primary Examiner*—Brian L. Casler
*Assistant Examiner*—Nasir Shahrestani
(74) *Attorney, Agent, or Firm*—Ann W. Speckman; Speckman Law Group PLLC

(57) ABSTRACT

Systems and methods for determining ICP based on parameters that can be measured using non-invasive or minimally invasive techniques are provided, wherein a non-linear relationship is used to determine ICP based on one or more variable inputs. The first variable input relates to one or more properties of a cranial blood vessel and/or blood flow, such as acoustic backscatter from an acoustic transducer having a focus trained on a cranial blood vessel, flow velocity in a cranial blood vessel, and the like. Additional variables, such as arterial blood pressure (ABP), may be used in combination with a first variable input relating to one or more properties of a cranial blood vessel, such as flow velocity of the middle cerebral artery (MCA) to derive ICP using a non-linear relationship. Methods and systems for locating target areas based on their acoustic properties and for acoustic scanning of an area, identification of a target area of interest based on acoustic properties, and automated focusing of an acoustic source and/or detector on a desired target area are also provided. Acoustic transducer assemblies are described.

43 Claims, 18 Drawing Sheets

U.S. PATENT DOCUMENTS

| | | | |
|---|---|---|---|
| 4,043,321 A | 8/1977 | Soldner et al. | |
| 4,771,792 A | 9/1988 | Seale | |
| 4,907,595 A | 3/1990 | Strauss | |
| 4,984,567 A | 1/1991 | Kageyama et al. | |
| 5,074,310 A | 12/1991 | Mick | |
| 5,086,775 A | 2/1992 | Parker et al. | |
| 5,099,848 A | 3/1992 | Parker et al. | |
| 5,117,835 A | 6/1992 | Mick | |
| 5,241,964 A | 9/1993 | McQuilkin | |
| RE34,663 E | 7/1994 | Seale | |
| 5,388,583 A | 2/1995 | Raguauskas et al. | |
| 5,411,028 A | 5/1995 | Bonnefous | |
| 5,524,636 A | 6/1996 | Sarvazyan et al. | |
| 5,579,774 A | 12/1996 | Miller et al. | |
| 5,606,971 A | 3/1997 | Sarvazyan | |
| 5,617,873 A | 4/1997 | Yost et al. | |
| 5,678,565 A | 10/1997 | Sarvazyan | |
| 5,685,313 A | 11/1997 | Mayevsky | |
| 5,749,364 A | 5/1998 | Sliwa, Jr. et al. | |
| 5,806,521 A | 9/1998 | Morimoto et al. | |
| 5,807,250 A | 9/1998 | Ohtomo et al. | |
| 5,810,731 A | 9/1998 | Sarvazyan et al. | |
| 5,830,131 A | 11/1998 | Caro et al. | |
| 5,836,894 A | 11/1998 | Sarvazyan | |
| 5,840,018 A | 11/1998 | Michaeli | |
| 5,844,140 A * | 12/1998 | Seale | 73/633 |
| 5,873,840 A | 2/1999 | Neff | |
| 5,903,516 A | 5/1999 | Greenleaf et al. | |
| 5,916,171 A | 6/1999 | Mayevsky | |
| 5,919,144 A | 7/1999 | Bridger et al. | |
| 5,921,928 A | 7/1999 | Greenleaf et al. | |
| 5,951,476 A | 9/1999 | Beach | |
| 5,951,477 A | 9/1999 | Raguskas et al. | |
| 5,971,927 A | 10/1999 | Mine | |
| 6,020,675 A | 2/2000 | Yamashita et al. | |
| 6,039,691 A | 3/2000 | Walker et al. | |
| 6,042,545 A | 3/2000 | Hossack et al. | |
| 6,042,556 A | 3/2000 | Beach et al. | |
| 6,066,097 A | 5/2000 | Glenn et al. | |
| 6,086,533 A | 7/2000 | Madson et al. | |
| 6,099,471 A | 8/2000 | Torp et al. | |
| 6,110,114 A | 8/2000 | Nock et al. | |
| 6,113,559 A | 9/2000 | Klopotek | |
| 6,117,089 A | 9/2000 | Sinha | |
| 6,129,682 A | 10/2000 | Borchert et al. | |
| 6,210,346 B1 * | 4/2001 | Hall et al. | 600/561 |
| 6,328,694 B1 * | 12/2001 | Michaeli | 600/438 |
| 6,352,507 B1 | 3/2002 | Torp et al. | |
| 6,368,277 B1 | 4/2002 | Mao et al. | |
| 6,488,626 B1 | 12/2002 | Lizzi et al. | |
| 6,527,717 B1 | 3/2003 | Jackson et al. | |
| 6,589,189 B2 * | 7/2003 | Meyerson et al. | 600/561 |
| 6,635,017 B1 | 10/2003 | Moehring et al. | |
| 6,682,483 B1 | 1/2004 | Abend et al. | |
| 6,689,064 B2 | 2/2004 | Hager et al. | |
| 6,692,443 B2 | 2/2004 | Crutchfield et al. | |
| 6,723,051 B2 | 4/2004 | Davidson et al. | |
| 6,761,695 B2 | 7/2004 | Yost et al. | |
| 6,854,338 B2 * | 2/2005 | Khuri-Yakub et al. | 73/861.27 |
| 6,875,176 B2 * | 4/2005 | Mourad et al. | 600/442 |
| 7,122,007 B2 | 10/2006 | Querfurth | |
| 7,125,383 B2 | 10/2006 | Hoctor et al. | |
| 2002/0095087 A1 | 7/2002 | Mourad et al. | |
| 2004/0049105 A1 | 3/2004 | Crutchfield et al. | |
| 2004/0059220 A1 | 3/2004 | Mourad et al. | |
| 2004/0138563 A1 | 7/2004 | Moehring | |
| 2004/0267127 A1 | 12/2004 | Abend et al. | |

FOREIGN PATENT DOCUMENTS

| | | | |
|---|---|---|---|
| WO | WO 99/56625 | * 11/1999 | |
| WO | WO-0057766 | 10/2000 | |
| WO | WO-0068647 | 11/2000 | |
| WO | WO-01/89358 A2 | 11/2001 | |

OTHER PUBLICATIONS

Nichols, John S., et al., "Detection of Impaired Cerebral Autoregulation Using Spectral Anaiysis of Intracranial Preesure Waves," *Journal of Neurotrauma*, vol. 13, No. 8, pp. 439-456 (1996).

Daley, M.L., et al., "Correlation Coefficient Between Intracranial and Arterial Pressures: A Gauge of Cerebral Vascular Dilation," *Acta Neurochir*, [Suppl] vol. 71, pp. 285-288 (1998).

Wayengerg, J.-L., "Non-Invasisve Measurement of Intercranial Pressure in Neonates and Infants: Experience with the Rotterdam Teletransducer," *Acta Neurochir*, [Suppl] vol. 71, pp. 70-73 (1998).

Nightingale, Kathryn R., et al., "On the Feasibility of Remote Palpation Using Acoustic Radiation Force," *J. Acoust. Soc. Am.*, vol. 110, No. 1, pp. 625-634 (Jul. 2001).

Fry, F. J., et al., "Threshold Ultrasonic Dosages for Structural Changes in the Mammalian Brain," *J. Acoust. Soc. Am.*, vol. 48, No. 6 (Part 2), pp. 1413-1417 (May 1970).

Davies, Iolo ab Ithel, et al., "Application of Focused Ultrasound for Research on Pain," *Pain*. vol. 67, pp. 17-27 (1996).

Parker, Kevin J., Ph.D., "Sonoelasticity Imaging," http://www.ee.Rochester.edu:8080/projects/sonoelasticity/patents.html, (printed Oct. 17, 2000).

Sujimoto, Tsuneyhoshi et al., "Tissue Hardness Measurement Using the Radiation Force of Focused Ultrasound," *Tokyo Institute of Technology, Research Laboratory of Precision Machinery and Electronics Ultrasonics Symposium*, pp. 1377-1380 (1990).

Braukus, Michael et al., "NASA Tests Painless Ways of Measuring Intracranial Pressure." http://www.qadas.com/qadas/nasa/nasa-hm/0092.html (printed Oct. 3, 2000).

Fatemi, Mostafa et al., "Ultrasound-Stimulated Vibro-Acoustic Spectrography," *Science*. vol. 280, No. 3, pp. 82-85 (Apr. 1998).

Schmidt, Bernhard et al., "Noninvasive Prediction of Intracranial Pressure Curves Using Transcranial Doppler Ultrasonography and Blood Pressure Curves," *Stroke*. vol. 28, No. 12, pp. 2465-2472 (Dec. 1997).

IBM Technical Disclosure Bulletin, "Noninvasisve Pressure Measurement," http://www.delphion.com/tdbs/tdb?&order+78A=00387 (printed Nov. 22, 2000).

M. Czosnyka, P., et al., "Continuous Monitoring of Cerebrovascular Pressure-Reactivity in Head Injury," *Acta Neurochir*, [Suppl] vol. 71, pp. 74-77 (1998).

* cited by examiner

METHODS FOR DETERMINING INTRACRANIAL PRESSURE NON-INVASIVELY

REFERENCE TO PRIORITY APPLICATION

This application claims priority to U.S. Provisional Application No. 60/475,803 filed Jun. 3, 2003 and U.S. Provisional Application No. 60/508,836 filed Oct. 1, 2003. This application is also a continuation-in-part of U.S. patent application Ser. No. 09/995,897, filed Nov. 28, 2001, issued Apr. 5, 2005 as U.S. Pat. No. 6,875,176, which claims priority to U.S. Provisional Application No. 60/253,959, filed Nov. 28, 2000. These patent applications are incorporated herein by reference in their entireties.

STATEMENT AS TO RIGHTS TO INVENTIONS MADE UNDER FEDERALLY SPONSORED RESEARCH AND DEVELOPMENT

The U.S. Government has a paid-up license in this invention and the right in limited circumstances to require the patent owner to license others on reasonable terms as provided for by the terms of Grant No. K25NS02234-02 awarded by the National Institutes of Health.

TECHNICAL FIELD OF THE INVENTION

In one aspect, the present invention relates to methods and systems for determining intracranial pressure (ICP) based on variable physiological parameters that can be measured using non-invasive or minimally invasive techniques. In another aspect, the present invention relates to methods and systems for acquiring and processing acoustic data to derive accurate ICP determinations non-invasively. In yet another aspect, the present invention provides methods and systems for locating target areas based on their acoustic properties and for acoustic scanning of an area, identification of a target site within the area of interest based on its acoustic properties, and automated focusing of an acoustic source and/or detector at the target site. Acoustic transducer assemblies, arrays and source/detector combinations for use in methods and systems of the present invention are also provided.

BACKGROUND OF THE INVENTION

Ultrasound imaging is a non-invasive, diagnostic modality that provides information relating to tissue properties and spatial location of physiological structures. In the field of medical imaging, ultrasound may be used in various modes to produce images of objects or structures within a patient. In a transmission mode, an ultrasound transmitter is placed on one side of an object and the sound is transmitted through the object to an ultrasound receiver. An image may be produced in which the brightness of each image pixel is a function of the amplitude of the ultrasound that reaches the receiver (attenuation mode), or the brightness of each pixel may be a function of the time required for the sound to reach the receiver (time-of-flight mode). Alternatively, if the receiver is positioned on the same side of the object as the transmitter, an image may be produced in which the pixel brightness is a function of the amplitude of reflected ultrasound (reflection or backscatter or echo mode). In a Doppler mode of operation, the tissue (or object) is imaged by measuring the phase shift of the ultrasound reflected from the tissue (or object) back to the receiver.

Ultrasonic transducers for medical applications are constructed from one or more piezoelectric elements activated by electrodes. Such piezoelectric elements may be constructed, for example, from lead zirconate titanate (PZT), polyvinylidene diflouride (PVDF), PZT ceramic/polymer composite, and the like. The electrodes are connected to a voltage source, a voltage waveform is applied, and the piezoelectric elements change in size at a frequency corresponding to that of the applied voltage. When a voltage waveform is applied, the piezoelectric elements emit an ultrasonic wave into the media to which it is coupled at the frequencies contained in the excitation waveform. Conversely, when an ultrasonic wave strikes the piezoelectric element, the element produces a corresponding voltage across its electrodes. Numerous ultrasonic transducer constructions are known in the art.

When used for imaging, ultrasonic transducers are provided with several piezoelectric elements arranged in an array and driven by different voltages. By controlling the phase and amplitude of the applied voltages, ultrasonic waves combine to produce a net ultrasonic wave that travels along a desired beam direction and is focused at a selected point along the beam. By controlling the phase and the amplitude of the applied voltages, the focal point of the beam can be moved in a plane to scan the subject. Many such ultrasonic imaging systems are well known in the art.

Doppler ultrasound has been in use in medicine for many years. Doppler ultrasound techniques measure the frequency shift (the "Doppler Effect") of reflected sound, which indicates the velocity of the reflecting material. Long-standing applications of Doppler ultrasound include monitoring of the fetal heart rate during labor and delivery and evaluating blood flow in the carotid artery. The use of Doppler ultrasound has expanded greatly in the past two decades, and Doppler ultrasound is now used in many medical specialties, including cardiology, neurology, radiology, obstetrics, pediatrics, and surgery. Doppler technology today allows detection of flow in intracranial arteries.

Transcranial Doppler (TCD) techniques require application of the ultrasound to those areas of the skull where the bone is relatively thin. The frequency of the Doppler signal is also adjusted, and pulsed wave rather than continuous wave ultrasound is used to augment the transmission of ultrasound waves through the skull. Velocities from the cerebral arteries, the internal carotids, the basilar and the vertebral arteries can be sampled by altering the transducer location and angle, and the instrument's depth setting. The most common windows in the cranium are located in the orbit (of the eye), and in the temporal and suboccipital regions.

TCD ultrasonography provides an easy-to-use, non-invasive, non-radioactive, and relatively inexpensive method to assess intracerebral hemodynamics with time resolution and provides reliable detection of cerebral perfusion changes. Using TCD ultrasonography, cerebrovascular responsiveness to various physiological and pharmacological challenges can be assessed instantaneously, and various cerebral circulatory tests can be repeated often and safely. Rapid changes of cerebral perfusion over time can be easily followed, documented and analyzed.

Intracranial Pressure

Normal, healthy mammals, particularly humans, have a generally constant intracranial volume and, hence, a generally constant intracranial pressure. Various conditions produce changes in the intracranial volume and, consequently, produce changes in intracranial pressure. Increases in intracranial pressure may produce conditions under which the intracranial pressure rises above normal and approaches or even equals the mean arterial pressure, resulting in reduced blood flow to the brain. Elevated intracranial pressure not only reduces blood flow to the brain, but it also affects the normal metabolism of cells within the brain. Under some conditions, elevated intracranial pressures may cause the brain to be mechanically compressed, and to herniate.

The most common cause of elevated intracranial pressure is head trauma. Additional causes of elevated intracranial pressure include shaken-baby syndrome, epidural hematoma, subdural hematoma, brain hemorrhage, meningitis, encephalitis, lead poisoning, Reye's syndrome, hypervitaminosis A, diabetic ketoacidosis, water intoxication, brain tumors, other masses or blood clots in the cranial cavity, brain abcesses, stroke, ADEM (acute disseminated encephalomyelitis), metabolic disorders, hydrocephalus, and dural sinus and venous thrombosis. Changes in intracranial pressure, particularly elevated intracranial pressure, are very serious and may be life threatening. They require immediate treatment and continued monitoring.

Conventional intracranial pressure monitoring devices include: epidural catheters; subarachnoid bolt/screws; ventriculostomy catheters; and fiberoptic catheters. All of these methods and systems are invasive. An epidural catheter may be inserted, for example, during cranial surgery. The epidural catheter has a relative low risk of infection and it does not require transducer adjustment with head movement, but the accuracy of sensing decreases through dura, and it is unable to drain CSF. The subarachnoid bolt/screw technique requires minimal penetration of the brain, it has a relatively low risk of infection, and it provides a direct pressure measurement, but it does require penetration of an intact skull and it poorly drains CSF. The ventriculostomy catheter technique provides CSF drainage and sampling and it provides a direct measurement of intracranial pressure, but the risks of infection, intracerebral bleeding and edema along the cannula track are significant, and it requires transducer repositioning with head movement. Finally, the fiber optic catheter technique is versatile because the catheter may be placed in the ventricle or in the subarachnoid space or brain tissue, and it does not require adjustment of the transducer with head movement, but it requires a separate monitoring system.

All of these conventional techniques require invasive procedures and none is well suited to long term monitoring of intracranial pressure on a regular basis. Moreover, these procedures can only be performed in hospitals staffed by qualified neurosurgeons. In addition, all of these conventional techniques measure ICP locally, and presumptions are made that the local ICP reflects the whole brain ICP.

Various methods and systems have been developed for measuring intracranial pressure indirectly and/or non-invasively. Several of these methods involve ultrasound techniques.

U.S. Pat. No. 5,951,477 of Ragauskas et al., for example, discloses an apparatus for non-invasively measuring intracranial pressure using an ultrasonic Doppler device that detects the velocities of the blood flow inside the optic artery for both intracranial and extracranial optic artery portions. The eye in which the blood flow is monitored is subjected to a small pressure, which is sufficient to equalize the blood flow measurements of the intracranial and extracranial portions of the optic artery. The pressure at which such equalization occurs is disclosed to be an acceptable indication of the intracranial pressure. In practice, a pressurized chamber is sealed to the perimeter around an eye and the pressure in the chamber is controlled to equalize blood velocities of intracranial and extracranial portions of the optic artery.

U.S. Pat. No. 5,388,583, to Ragauskas et al., discloses an ultrasonic non-invasive technique for deriving the time dependencies of characteristics of certain regions in the intracranial medium. Precise measurements of the transit travel times of acoustic pulses are made and processed to extract variable portions indicative of, for example, the pulsatility due to cardiac pulses of a basal artery or a cerebroventricle or the variation in the pressure of brain tissue, as well as changes in the cross-sectional dimension of the basal artery and ventricle. Frequency and phase detection techniques are also described.

U.S. Pat. No. 5,411,028 to Bonnefous discloses an ultrasonic echograph used for the measurement of various blood flow and blood vessel parameters that provide information for calculating determinations relating to the elasticity or compliance of an artery and its internal pressure.

U.S. Pat. No. 5,117,835 to Mick discloses a method and apparatus for non-invasively measuring changes in intracranial pressure by measuring changes in the natural frequency and frequency response spectrum of the skull bone. Changes in the natural frequency and frequency response spectrum of the skull are measured by applying a mechanical forced oscillation stimulus that creates a mechanical wave transmission through the bone, and then sensing the frequency response spectrum. Comparison of spectral response data over time shows trends and changes in ICP.

U.S. Pat. No. 6,129,682 to Borchert et al. discloses a method for non-invasively determining ICP based on intraocular pressure (IOP) and a parameter of the optic nerve, such as thickness of the retinal nerve fiber layer or anterior-posterior position of the optic nerve head.

U.S. Pat. No. 6,086,533 to Madsen et al. discloses systems for non-invasive measurement of blood velocity based on the Doppler shift, and correlation of blood velocity before and after the manual application of an externally applied pressure, to provide a measure of intracranial pressure, ophthalmic pressure, and various other body conditions affecting blood perfusion.

U.S. Pat. No. 5,919,144 to Bridger et al. discloses a non-invasive apparatus and method for measuring intracranial pressure based on the properties of acoustic signals that interacted with the brain, such as acoustic transmission impedance, resonant frequency, resonance characteristics, velocity of sound, and the like. Low intensity acoustic signals having frequencies of less than 100 kHz are used.

U.S. Pat. No. 4,984,567 to Kageyama et al. discloses an apparatus for measuring intracranial pressure using ultrasonic waves. Data from interference reflection waves caused by multiple reflections of incident ultrasonic waves at the interstitial boundaries within the cranium are analyzed for frequency, and the time difference between the element waves of the interference reflection wave is calculated and provided as output. The device described incorporates an electrocardiograph for detecting the heart beat, a pulser for generating a voltage pulse, an ultrasonic probe for receiving the pulse and transmitting an ultrasonic pulse into the cranium and receiving the echo of the incident wave, and a processor for making various calculations.

U.S. Pat. No. 5,951,476 to Beach provides a method for detecting brain microhemorrhage by projecting bursts of ultrasound into one or both of the temples of the cranium, or into the medulla oblongata, with the readout of echoes received from different depths of tissue displayed on a screen. The readouts of the echoes indicated accrued microshifts of the brain tissue relative to the cranium. The timing of the ultrasound bursts is required to be synchronized with the heart pulse of the patient.

U.S. Pat. No. 6,042,556 discloses a method for determining phase advancement of transducer elements in high intensity focused ultrasound. Specific harmonic echoes are distributed in all directions from the treatment volume, and the temporal delay in the specific harmonic echoes provides a measure of the propagation path transit time to transmit a pulse that converges on the treatment volume.

U.S. Pat. No. 3,872,858 discloses an echoencephalograph for use in the initial diagnosis of midline structure lateral shift that applies an ultrasonic pulse to a patient's head, the pulse traveling to a predetermined structure and being partially reflected as an echo pulse. Shifts are determined by measuring the travel time of the echo pulse.

U.S. Pat. No. 4,984,567 describes an apparatus for measuring intracranial pressure based on the ultrasonic assay of changes in the thickness of the dura covering the brain induced by changes in ICP.

Michaeli et al., in PCT International Publication No. WO 00/68647, describe determination of ICP, non-invasively, using ultrasonic backscatter representative of the pulsation of a ventricle in the head of the patient. This includes the analysis of echo pulsograms (EPG). Michaeli et al., in U.S. Pat. No. 6,328,694 B1, disclose apparatus and methods for tissue resonance analysis involving generating an ultrasound pulse that propagates through the skull and brain of the patient and is reflected off the skull and soft tissue lying in a path perpendicular to the ultrasound probe. The reflected signals are processed, in a known manner, to generate an echo encephalogram (Echo EG), which is plotted as a function of amplitude vs. distance. A portion of the Echo EG signal is selected and integrated over the selected portion to generate an echo pulsograph (EPG) signal. Using an ECG signal as a reference, the EPG signal is used to provide information regarding the physiological state of tissue. In one specific embodiment, the EPG signal is used to provide a quantitative measure of ICP using the relationship described at Col. 8, line 7.

PCT International Publication No. WO 02/43564, which is incorporated herein by reference in its entirety, discloses methods and systems for assessment of tissue properties, non-invasively, by acquiring data relating to at least one aspect of intrinsic and/or induced tissue displacement, or associated biological responses. Data relating to tissue displacement and associated biological changes are acquired by detecting acoustic properties of tissue using ultrasound interrogation pulses, preferably in a scatter or Doppler detection mode. Specific applications for such systems and methods include noninvasive assessment and monitoring of ICP, arterial blood pressure (ABP), CNS autoregulation status, vasospasm, stroke, local edema, infection and vasculitis, as well as diagnosis and monitoring of diseases and conditions that are characterized by physical changes in tissue properties.

NASA has also worked on the development of methods and systems for noninvasive intracranial pressure measurement. Intracranial pressure dynamics are important for understanding adjustments to altered gravity. ICP may be elevated during exposure to microgravity conditions. Symptoms of space adaptation syndrome are similar to those of elevated intracranial pressure, including headache, nausea and projectile vomiting. The hypothesis that ICP is altered in microgravity environments is difficult to test, however, as a result of the invasive nature of conventional ICP measurement techniques. NASA has therefore developed a modified pulsed phase-locked loop (PPLL) method for measuring ICP based on detection of skull movements which occur with fluctuations in ICP. Detection of skull pulsation uses an ultrasound technique in which slight changes in the distance between an ultrasound transducer and a reflecting target are measured. The instrument transmits a 500 kHz ultrasonic tone burst through the cranium, which passes through the cranial cavity, reflects off the inner surface of the opposite side of the skull, and is received by the same transducer. The instrument compares the phase of emitted and received waves and alters the frequency of the next stimulus to maintain a 90 degree phase difference between the ultrasound output and the received signal. Experimental data demonstrated that the PPLL output was highly and predictably related to directly measured ICP.

Schmidt et al., in several publications, describe a non-invasive methodology for monitoring ICP in several literature articles using a mathematical model that relates arterial blood pressure (ABP) and blood flow velocity (FV) to ICP using linear transformation rules. Flow velocity measurements were taken using Transcranial Doppler (TCD) devices. Correlations were also made to cerebral autoregulation.

The model of Schmidt et al. was able to realistically simulate ICP curves in a subset of patients, although not to a clinically useful degree. We hypothesized that while a linear systems analysis of ICP mechanics is a well-considered approach, the non-linear features inherent in the cardiovascular system (non-linear viscoelastic characteristics of arteries and non-Newtonian fluid properties of blood, among others) would be better characterized by a non-linear systems analysis model.

U.S. Patent Applications 2001/0039386 A1 and 2002/0183650 A1 disclose methods for eliminating slow drift artifacts from sonomicrometer signals to improve the quality of ICP measurement data obtained from skull diameter measurements. These methods involve using a neural network or another non-linear engine to extract a heartbeat component from the sonomicrometer output.

Arterial Blood Pressure

Arterial blood pressure (ABP) is a fundamental objective measure of the state of an individual's health. Indeed, it is considered a "vital sign" and is of critical importance in all areas of medicine and healthcare. The accurate measure of ABP assists in determination of the state of cardiovascular and hemodynamic health in stable, urgent, emergent, and operative conditions, indicating appropriate interventions to maximize the health of the patient.

Currently, ABP is most commonly measured non-invasively using a pneumatic cuff, often described as pneumatic plethysmography or Kortkoff's method. While this mode of measurement is simple and inexpensive to perform, it does not provide the most accurate measure of ABP, and it is susceptible to artifacts resulting from the condition of arterial wall, the size of the patient, the hemodynamic status of the patient, and autonomic tone of the vascular smooth muscle. Additionally, repeated cuff measurements of ABP result in falsely elevated readings of ABP, due to vasoconstriction of the arterial wall. To overcome these problems, and to provide a continuous measure of ABP, invasive arterial catheters are used. While such catheters are very reliable and provide the most accurate measure of ABP, they require placement by trained medical personnel, usually physicians, and they require bulky, sophisticated, fragile, sterile instrumentation. Additionally, there is a risk of permanent arterial injury causing ischemic events when these catheters are placed. As a result, these invasive monitors are only used in hospital settings and for patients who are critically ill or are undergoing operative procedures.

SUMMARY OF THE INVENTION

Methods and systems of the present invention provide accurate assessment and monitoring of ICP based on one or more variable physiological parameters that can be measured using non-invasive or minimally invasive techniques. One of the variable physiological parameters may relate to intracranial blood flow and may, for example, be quantified as an acoustic property of tissue or blood that is related to intracranial blood flow or intracranial flow velocity, such as cerebral blood flow or flow velocity. In one embodiment, ICP is determined based on an acoustic property of cerebral tissue, or on blood flow or cerebral blood flow velocity, and/or arterial blood pressure (ABP).

In an exemplary embodiment described in detail below, patient ICP is determined based on at least two variable parameters: (1) acoustic scatter or flow velocity in the middle cerebral artery (V_mca) measured, for example, using a TCD device; and (2) ABP measured invasively or non-invasively. ABP may be measured using conventional techniques, or using ultrasound techniques as described herein. In one embodiment, ABP is measured non-invasively, using "active" and/or "passive" ultrasound techniques, in a cranial blood vessel such as the MCA or a carotid or vertebral artery. In this embodiment, V_mca may be determined simultaneously or alternatively with ABP using an ultrasound device of the present invention.

In another embodiment, patient ICP is determined based on: (1) Doppler or other acoustic measurements, such as acoustic scatter, taken from a target site on or within or in proximity to a cranial blood vessel such as the MCA, a carotid artery, or another cranial blood vessel; and (2) ABP and/or CNS tissue displacement measured using active and/or passive acoustic techniques described herein in one or more target CNS sites different from the target site on or within or in proximity to a cranial blood vessel. In yet another embodiment, patient ICP is determined based on: (1) acoustic scatter data acquired from a target site on or within or in proximity to a cranial blood vessel, such as the MCA or a carotid or a vertebral artery; and (2) ABP and/or acoustic scatter data acquired from one or more target CNS sites different from the target site on or within or in proximity to a cranial blood vessel.

Other physiological properties of blood and/or central nervous system (CNS) tissue, such as tissue stiffness, endogenous and/or induced tissue displacement, partial pressure of gases associated with brain respiration and metabolism such as $pCO_2$, blood perfusion, hematocrit, EKG and/or electrophysiological properties of tissue, such as evoked potentials, may also be used to determine ICP in accordance with methods and systems of the present invention. In many embodiments, one or more of these physiological properties of blood and/or CNS tissue is used, together with acoustic scatter data and/or Doppler analysis of scatter data, and/or ABP, to determine instantaneous ICP. In alternative embodiments, one or more physiological properties of blood and/or CNS tissue may be used, without requiring data relating to flow velocity, to determine instantaneous ICP.

Acoustic properties of tissues, including blood, blood vessel walls and blood vessels, and tissue displacement, may be evaluated using ultrasound techniques described in PCT International Publication WO 02/43564 and U.S. Patent Application No. US 2002/0095087 A1, which are incorporated herein by reference in their entireties. These publications disclose "active" and "passive" acoustic modes, both of which may be used in methods and systems of the present invention. In a "passive" mode, acoustic (ultrasound) techniques are used to acquire data relating to intrinsic (endogenous) tissue displacement. In one "active" mode, acoustic (ultrasound) techniques are used to stimulate or probe target tissue, or induce a response at a target tissue site, by the application of focused ultrasound. In another "active" mode, acoustic (ultrasound) techniques use the application of focused ultrasound to produce oscillation of targeted tissue. Ultrasound backscatter and/or emission data, for example, are related to intrinsic tissue displacements, which can be related to ICP, ABP, CPP, autoregulation status and various tissue properties and physiological conditions. In some embodiments of methods and systems of the present invention, both passive and active ultrasound techniques may be used, simultaneously or alternatively, to assess tissue properties. In one embodiment of the present invention, for example, "passive" ultrasound techniques, such as TCD techniques, are used to determine V_mca, while "passive" and/or "active" ultrasound techniques are used to measure ABP. The V_mca and ABP measurements may be used, for example, to determine ICP.

For example, the magnitude and/or amplitude and/or phase of acoustic scatter from target tissue sites in the CNS undergoing intrinsic displacements during the course of arterial blood flow and CSF supply, is directly related to the stiffness, e.g. Young's modulus, of the CNS tissue, and is therefore empirically related to ICP. Alternatively or additionally, relationships between the major and minor intrinsic oscillations of CNS tissue within a cardiac cycle, or within a cardiac cycle as modulated by one or more respiratory cycles, are empirically related to ICP. Additional properties of the intrinsic tissue displacement that may be determined and related to tissue properties include: various components of amplitude, such as maximum amplitude within a cardiac cycle, the ratio of the maximum amplitude to that of the mean or variance of subsequent oscillations within a cardiac cycle, all possible rates of change of intrinsic CNS tissue displacement or relaxation, such as the velocity or acceleration of displacement, and the like. Additional data, such as ABP measurements and/or respiration data, may be collected and used, with the acoustic data, to make various assessments and determinations of ICP, CPP, autoregulation status or capacity, and the like.

In a first "active" acoustic data acquisition mode, methods and systems of the present invention stimulate or probe target tissue, or induce a response at a target tissue site, by application of focused ultrasound. The response of the targeted tissue to the application of focused ultrasound may be displacement or a change in relative position, a sensation such as pain, a change in temperature, a change in blood flow, or another detectable response. For example, application of an acoustic radiation force to "palpate" a target tissue location may be accomplished by administering one or more acoustic signals. Non-invasive techniques, such as ultrasound, optical techniques such as near infrared spectroscopy and optical coherence tomography, and other techniques, including magnetic resonance techniques, external electrophysiological stimulation, patient response, and the like are used to assess at least one response to the application of focused ultrasound. A visualization or imaging technique, such as ultrasound imaging or magnetic resonance imaging, may also be employed to assist in targeting the focused ultrasound pulse(s) and to assist in differentially localizing responsive tissues.

Biological materials, such as CNS tissue, absorb some of the ultrasound as it propagates into and through the material. See, e.g., Rudenko et al. (1996), "Acoustic radiation force and streaming induced by focused non-linear ultrasound in a dissipative medium," J. Acoust. Soc. Am 99(5) 2791-2798. Also, at the boundaries between different tissue types, such as between CSF and brain tissue, there is an 'impedance mismatch' (that is, differences between the product of density and speed of sound from one tissue to another) that allows ultrasound to push on the interface. See, e.g., Chu and Apfel (1982) "Acoustic radiation pressure produced by a beam of sound," J. Acoust. Soc. Am 72(6), 1673-1687. The deflection caused by the radiation force described by Chu is likely greater for brain than that of radiation force described by Rudenko et al., either at the CSF/brain interface for ultrasound with a wavelength significantly smaller than the distance between dura and brain, or at the effective bone/brain interface for ultrasound with a wavelength significantly larger than the distance between dura and brain. The formula for the two contributions to radiation pressure can be modified for wavelengths of sound comparable to the distance between dura and brain.

In the described embodiments, we have made certain simplifying assumptions, just described, without limiting the scope of the application. It is useful to note the following formula for the net pressure (force per unit area) P at an interface between two tissues given by Chu and Apfel, their equation (69):

$$P = 2(rho\_1/rho\_0) * K * <E> * (1 + (rho\_1 * c\_1)/(rho\_0 * c\_0))^{(-2)}$$

where rho_i is the density of the medium (i), c_i is its sound speed, K is the "non-linearity" parameter of medium 1, and <E> is the time-averaged energy density associated with the ultrasonic wave incident on the target site, which can be calculated if one knows the amplitude of the acoustic wave at the interface of interest. For present purposes, medium "1" is the brain, while medium "0" is either the CSF or bone.

Tissue displacement may thus be induced, and tissue may be acoustically palpated or oscillated, to produce displacement and other biological responses, and acoustic emissions, by application of focused ultrasound. Using an acoustic radiation force, a single frequency acoustic source causes materials that are at least somewhat compliant, such as brain tissue, to move in a single direction relative to the source during propagation, while the material returns to its original location when propagation from the acoustic source is discontinued. Repeated pulses induce a repeated series of displacements and relaxations of the tissue.

For assessment of CNS tissue and determination of ICP, for example, one or more acoustic transducer(s) is placed in contact with or in proximity to a subject's skull. An initial environmental assessment, described below and preferably employing ultrasound techniques, may be made, if desired, to assess the characteristics of the environment between the acoustic source and the target tissue site, so that the magnitude of the acoustic force applied to the target tissue may be determined. Environmental factors, such as the distance between the acoustic transducer and various structural landmarks, such as the brain surface, the thickness of the skull, the thickness of the dura matter, the thickness of the arachnoid layer containing CSF, impedance mismatches between the various structures and tissues, and the like, may be determined. The initial environmental assessment is determinative of various method and system parameters. Environmental assessments may additionally be updated at intervals throughout a diagnostic or monitoring procedure.

Following the environmental assessment, an acoustic force is applied by an acoustic transducer, at a predetermined frequency, to displace the brain tissue at a desired location, such as at the surface of the brain. The deformation may be produced at any desired location within tissue, depending on the focus (foci) of the ultrasonic transducer(s) producing the acoustic radiation force. In some systems, variable foci ultrasonic transducers are provided, and a diagnostic procedure is carried out using a plurality of target tissue sites. According to one embodiment for assessment of ICP, the focus (foci) of the ultrasonic transducer(s) is preferably provided in proximity to the cortical surface or a small distance below the cortical surface, to maximize the tissue displacement induced by the radiation pressure that a rises from the impedance mismatch between brain and CSF or between brain and bone (depending on the frequency of the applied ultrasound). It is important to note, again, that the methods and systems of the present invention do not require the radiation force arising from the impedance mismatch described by Chu and Apfel to be significantly greater than that described by Rudenko et al.

The applied acoustic radiation force is sufficient to induce a detectable displacement in the CNS tissue, or the applied ultrasound beam is sufficient to produce a detectable biological response, without producing any medically undesirable changes in the examined tissue. For example, the acoustic radiation force applied must not produce shear in tissues in proximity to the target tissue of a magnitude sufficient to tear or damage tissue. The applied ultrasound, moreover, must not appreciably increase the temperature of examined tissue to the point of causing unacceptable damage, and it must not induce extensive or damaging cavitation or other sources of deleterious mechanical effects in the examined tissue. Suitable ultrasound dosages may be determined using well known techniques. For example, Fry et al. studied the threshold ultrasonic dosages causing structural changes in mammalian brain tissue and illustrate, in their FIG. 1, the acoustic intensity v. single-pulse time duration producing threshold lesions in white matter of the mammalian (cat) brain. Fry et al., *Threshold Ultrasonic Dosages for Structural Changes in the Mammalian Brain*, The Journal of the Acoustical Society of America, Vol. 48, No. 6 (Part 2), p. 1413-1417 (1970).

Additionally, the acoustic frequency must be low enough to penetrate the skull and high enough to produce measurable deformation in the target tissue at the location of interest. Within the parameters outlined above, higher frequency acoustic waves are more easily focused and, therefore, preferred. The intensity must be high enough to deform the tissue, but not be so great as to induce undesirable changes in the examined tissue. The pulse length is preferably relatively short, but long enough to create a measurable deformation or oscillation of the target tissue, as desired, while the pulse repetition frequency must be large enough to resolve medically interesting temporal features in the tissue, without inducing medically unacceptable changes in the tissue.

In general, at least one acoustic property related to tissue displacement, or an associated biological response, is determined and related to a tissue property and, ultimately, to a clinically important parameter. For example, the magnitude, or amplitude, of the displacement induced by the known acoustic force is directly related to the elasticity (or stiffness or compliance, e.g., Young's modulus) of the CNS tissue, and can therefore be empirically related to ICP. Additional properties of the target tissue displacement that may be determined and related to tissue properties include: various components of amplitude, such as maximum amplitude in the direction of the acoustic force or maximum amplitude perpendicular to the direction of acoustic force; all possible rates of change of the displacement or subsequent relaxation of the tissue, such as the velocity or acceleration of displacement or relaxation; the amplitude or rates of change of various components of the shape of the displacement; changes in Fourier or wavelett representations of the acoustic scatter signal associated with the displacement; properties of shear waves generated by the acoustic radiation force; properties of induced second harmonic deformation(s), and the like. Time displacements of pulse echoes returning from the target tissue are also indicative of the displacement amplitude and may be determined. These properties are all referred to as measures of "displacement."

In a second "active" mode of operation, application of focused ultrasound produces oscillation of targeted tissue, and data relating to the acoustic signals emitted from the targeted tissue are collected. These signals are referred to herein as acoustic emissions. In general, methods and systems of the present invention that relate to application of focused ultrasound may be used to produce oscillation of targeted tissue, and emitted acoustic signals are related to tissue properties and physiological conditions.

In one embodiment, methods and systems of the present invention employ a confocal acoustic system comprising at least two acoustic transducers, driven at different frequencies, or a focal acoustic system comprising a single acoustic transducer driven at a given pulse repetition frequency (PRF), to induce an oscillatory radiation force in the target tissue, such as brain tissue. The resulting oscillation is at a frequency that is the difference of the applied frequencies, at the target location that is marked by the overlap of the two confocal acoustic beams or, for the single transducer case, at the PRF. During and after the application of focused ultrasound, the targeted tissue emits acoustic signals related to its intrinsic properties. The second, active mode of operation may therefore be used to characterize tissue. Diagnostic ultrasound techniques may be used to measure the frequency or other properties of the emitted acoustic signal, which are empirically related to tissue properties.

Data relating to acoustic scatter produced as a result of focusing an ultrasound source on, or in, or in proximity to, an intracranial blood vessel may be acquired using non-invasive means and may provide data for determining ICP using methodologies and systems of the present invention. Properties of intracranial blood flow, such as flow velocity, may also be determined using Transcranial Doppler (TCD) techniques, and may provide data for determining ICP. Methods and systems of the present invention may use raw acoustic scatter data from a target site within the CNS or within, on or in proximity to (collectively, "on") a cranial blood vessel such as the MCA, or tissue in proximity to such a target site, or may use processed acoustic data, such as Doppler data.

Acoustic properties of tissue, including blood, blood vessel walls, tissue in proximity to blood flow, and other tissue sites, may be determined, for example, by collecting acoustic scatter data using an ultrasound transducer aimed at, or having a focus on an intracranial blood vessel, and/or at another target site. For purposes of determining ICP, the target site is preferably a CNS tissue site, such as a cranial blood vessel, brain tissue, or the like. The target site may be any tissue site (including blood, cerebral spinal fluid [CSF], dura etc., which are included in references to "tissue"), that is not predominantly bony tissue. For particular embodiments, a CNS target tissue site may be located on or within or in proximity to (collectively, "on") the spinal cord. In one embodiment, acoustic scatter data is acquired at a target site that is on the middle cerebral artery (MCA) using TCD techniques, as described below. Alternatively, acoustic properties of, such as acoustic scatter from, cranial blood vessels and other physiological structures that traverse the brain or are in communication with CNS tissue sites, such as the carotid and vertebral arteries, may be taken at locations outside the cranial cavity, and provide good target sites for measurement of acoustic data in methods of the present invention. Thus, while exemplary methods and systems of the present invention are described with reference to acquisition of acoustic data from target sites on the MCA, it will be recognized that target sites on other cranial blood vessels that are in communication with or traverse the CNS may also be used.

Ultrasound detection techniques are preferred for assessing the acoustic properties of target CNS tissue sites for many embodiments. Ultrasound sources and detectors may be employed in a transmission mode, or in a variety of reflection or scatter modes, including modes that examine the transference of pressure waves into shear waves, and vice versa. Detection techniques involving measurement of values for or changes in acoustic scatter, such as back scatter or forward scatter, or reflection, and particularly backscatter, are preferred for use in many embodiments of methods and systems of the present invention. Exemplary acoustic data that may be used to determine ICP according to the present invention include: values for or changes in acoustic scatter, including values of and changes in the amplitude, phase and/or frequency of acoustic signals, values for or changes in length of scattered signals relative to the interrogation signal, values for or changes in the primary and/or other maxima and/or minima amplitudes of an acoustic signal within a cardiac and/or respiratory cycle; values for or changes in ratios of the maximum and/or minimum amplitude to that of the mean or variance or distribution of subsequent signals within a cardiac cycle, values for or changes in temporal or spatial variance of scattered or emitted signals at different times in the same target location and/or at the same time in different target locations, values for or changes in endogenous and/or induced brain tissue displacement or relaxation, and rates of change for such displacements, such as the velocity or acceleration of displacement, and the like, and combinations of these data.

Multiple acoustic interrogation signals may be employed, at the same or different frequencies, pulse lengths, pulse repetition frequencies, intensities, and the multiple interrogation signals may be emitted from the same location, or multiple locations, simultaneously and/or sequentially. Acoustic scatter data may be collected, for example, from a cranial blood vessel at different points along the vessel, within or outside the cranial cavity, or from multiple sites at or in proximity to different vessels, or from multiple CNS tissue sites. Scatter from single or multiple interrogation signals may be detected at single or at multiple frequencies, at single or multiple time points, and at single or multiple locations. In one embodiment, methods and systems of the present invention may be used to localize differences in ICP within CNS tissue, thereby localizing areas of trauma or dysfunction. This may be achieved by acquiring acoustic data from a plurality of CNS sites and processing the plurality of data sets to determine ICP at corresponding multiple spatial locations within CNS tissue.

A property of intracranial blood flow, such as acoustic scatter or flow velocity, may be determined in any blood vessel that traverses, or enters or exits CNS tissue (collectively, "cranial blood vessels"), with arteries being preferred, and the Middle Cerebral Artery (MCA), carotid and vertebral arteries being especially suitable. Intracranial blood flow properties may be determined using any noninvasive or minimally invasive modality and is preferably determined using ultrasound techniques such as Transcranial Doppler (TCD) ultrasound techniques, which are well known in the art. In one embodiment, TCD techniques are used to measure flow velocity in the MCA (V_mca), and V_mca measurements are used alone, or with other physiological parameters such as ABP, and/or CNS tissue displacement, to determine ICP. Although evaluation of cranial blood vessel flow velocity using TCD is suitable for many embodiments of the methods and systems of the present invention, cranial blood vessel and/or blood flow characteristics, and other CNS tissue properties, may alternatively or additionally be measured, or predicted, using other modalities such as non-invasive optical detection techniques, such as near infrared spectroscopic (NIRS) techniques.

In one embodiment of methods and systems of the present invention that is described in detail below, two variable inputs, namely cranial blood flow velocity (or acoustic scatter data collected from a target site on a cranial blood vessel) and arterial blood pressure (ABP), are used to determine ICP. Ultrasound techniques are preferably used, non-invasively, to measure an acoustic property of cranial blood vessel(s) or blood flow, such as flow velocity. TCD is a preferred ultrasound technique and can provide substantially continuous measurement of flow velocity. Many types of TCD devices are known in the art and may be used for collecting the acoustic back scatter and/or cranial blood flow velocity data used as a variable input for ICP determinations of the present invention. The Spencer Technologies TCD 100M Power M-Mode Digital Transcranial Doppler device is one such suitable device. ABP is preferably measured using noninvasive techniques, although invasive techniques may be used.

Cranial blood vessel and/or blood flow characteristics and ABP may be measured on a substantially continuous or an intermittent basis. Blood flow velocity measurements may be determined on a substantially continuous basis, or on an intermittent basis, using TCD techniques. ABP may be determined on a substantially continuous basis using, for example, an invasive arterial line. ABP may be measured non-invasively, on an intermittent basis, using an arm or leg cuff. ABP may also be measured non-invasively, on an intermittent or substantially continuous basis using acoustic techniques as described in PCT International Publication No. WO 02/43564. ABP measurements may also be measured non-invasively using, for example, the VASOTRAC® device manufactured by Medwave, Inc., 4382 Round Lake Road West, St. Paul, Minn. 55112-3923.

In one aspect, ICP is determined by measuring an acoustic property relating to a cranial blood vessel, such as acoustic backscatter produced when an ultrasound beam is focused on a cranial blood vessel, or blood flow velocity measured, for example, using TCD techniques, and then using a non-linear relationship to relate the acoustic property and/or blood flow velocity to ICP. The non-linear relationships used to predict ICP in methods and systems of the present invention may be derived empirically, using first principles, or using a combination of empirical data with first principles. The non-linear relationship between blood vessel and/or blood flow properties may be derived, for example, based on non-linear empirical analytical methods such as the use of Hidden Markov Models, Support Vector Machines, Artificial Neural Networks, cellular automata and non-linear filters, as well as non-linear numerical methods. Several exemplary methodologies are described below.

In another aspect, ICP may be determined by measuring an acoustic property relating to a cranial blood vessel, such as acoustic scatter produced when an ultrasound beam is focused on a cranial blood vessel, or blood flow velocity, and then using a linear relationship between blood vessel and/or blood flow or CNS tissue properties (as described above) to relate the acoustic property and/or blood flow velocity to ICP. Linear relationships may be derived, for example, using first principles methods based on linear differential equations or based on linearized equations derived from non-linear fluid dynamics equations such as Navier-Stokes equations. Methodologies that are a hybrid of first principles methods and empirical methods may also be used. Exemplary methodologies are described below.

A neural network, set up and trained as described below, was used to derive a non-linear relationship, which is further characterized below, and which provided accurate determinations of ICP in experimental protocols based on two variable parameters: V_mca measurements taken using TCD techniques; and ABP measured using an arterial line. The ABP data collected using an invasive arterial line was also computationally adjusted to mimic ABP data that could be collected non-invasively using, for example, a pressure cuff. Accurate ICP determinations using V_mca measurements and the adjusted ABP data were also demonstrated using methodologies and systems of the present invention. Data, such as V_mca data and ABP data, may be acquired intermittently or on a substantially continuous basis. Data is preferably collected at least twice in a cardiac cycle. By measurement on a "substantially continuous basis" we mean collection at least four data points, and preferably at least six data points per cardiac cycle. Various methods and systems for predicting ICP based one or more variables that may be measured non-invasively or minimally invasively are described below.

In yet another aspect, methods and systems of the present invention may be used to non-invasively determine the autoregulation status of a patient together with, or separately from, a determination of ICP, ABP, and other CNS properties. Challenges resulting in a modulation of the arterial blood pressure may be administered, for example, by having a subject perform actions that modulate the ABP in a predictable fashion, by adjusting intrathoracic pressure using a ventilator, by restricting blood flow to an extremity, or by administering an agent, such as a diuretic and/or vasodilator or vasoconstrictor, that modulates arterial blood flow, may be used with methods and systems of the present invention to assess autoregulation.

Methods and systems of the present invention are preferably integrated in a controller component having data processing, storage and display features that provide meaningful information to professional clinicians. The controller component may be integrated with other clinical devices, or may be programmed to receive additional data inputs relating to other clinical parameters. In one embodiment, a "long term" ICP trace corresponding to ICP determinations made over a time period of at least several minutes and up to several hours or days is provided to illustrate trends and fluctuations in ICP determinations over time. ICP determinations taken over time and relating to a particular patient may also be stored and displayed, in a variety of formats, to illustrate ICP trends over various time periods. A "short term" ICP trace showing substantially instantaneous ICP measurements taken over two or more cardiac cycles may also be provided. An exemplary data display unit is described below.

In another aspect, methods and systems of the present invention provide spatial location of desired target areas based on their acoustic properties and automated focusing of an acoustic source at the desired target area. Suitable source/detector combinations and transducer assemblies for scanning and locating desired target areas are also described.

DETAILED DESCRIPTION OF THE INVENTION

Figure 1:
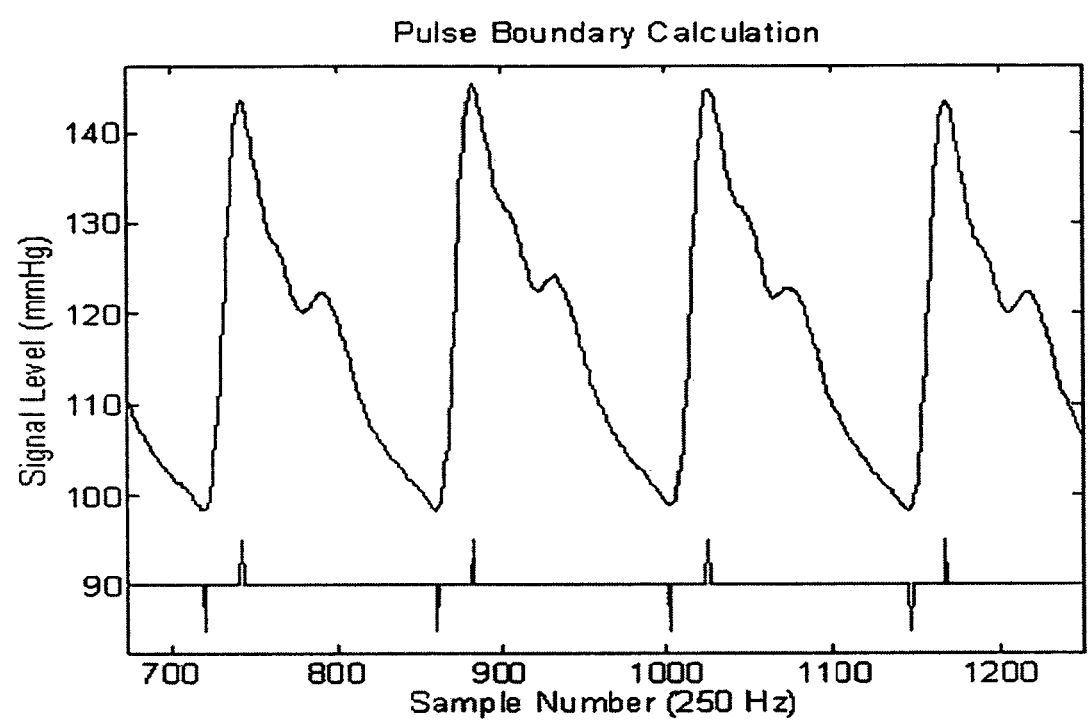
FIG. 1 shows exemplary output from the pulse boundary calculation used to delineate the beginning and end of each cardiac cycle. The upper trace represents the ABP signal. The lower trace marks systole (positive tick), and diastole (negative tick).

One aspect of methods and systems of the present invention relates to determination of ICP using variable input data that can be measured using non-invasive and/or minimally invasive measurement techniques. Methods and systems for determining ICP based on non-invasive or minimally invasive measurements of V_mca and/or ABP are described in detail. While the methods and systems of the present invention may be embodied in a variety of different forms, the specific embodiments shown in the figures and described herein are presented with the understanding that the present disclosure is to be considered exemplary of the principles of the invention, and is not intended to limit the invention to the illustrations and description provided herein. There are several alternative methods for determining ICP, most of which make use of a non-linear relationship between variable parameters, such as acoustic back scatter from within, on or in proximity to a cranial blood vessel alone, or in combination with ABP and/or other variable parameters and ICP.

Determination of ICP based on physiological measurements taken using non-invasive or minimally invasive techniques, including ultrasound techniques such as measurement of acoustic scatter and/or Doppler flow velocity, e.g. in the middle cerebral artery (V_mca) and invasive or non-invasive (e.g. cuff or tonometric) arterial blood pressure (ABP), among others, may be accomplished using a variety of empirical methods. In one embodiment, V_mca is measured (non-invasively) using Doppler techniques, and ABP is measured (non-invasively) in a cranial blood vessel such as the middle cerebral artery using "active" ultrasound techniques, as described herein. Both linear and non-linear systems and relationships may be used, though methodologies that implement non-linear relationships to determine ICP are generally preferred. Several different methodologies for determining a relationship between variable inputs, such as acoustic scatter, V_mca and ABP and the desired output, such as ICP, are described below.

Linear Filters

ICP prediction may be implemented using linear filters, including those with both infinite impulse response (IIR) and finite impulse response (FIR) properties. Linear filter operations are capable of scaling (i.e. filter output is proportional to input) and superposition (i.e. the sum of filter outputs from two separate inputs is the same as the filter output from the sum of two inputs). Such operations are described in Chen C, Linear System Theory and Design, Oxford University Press, 1999. The related quality of time-invariance (i.e. an operation having the same characteristic, such as frequency response, at all points in time) is also true for many linear systems, although an ICP prediction algorithm would not necessarily have to be time-invariant. Instead, the properties of the input signal(s) could dynamically dictate the response characteristics of the linear filter portion of the algorithm.

Although the assumption of linearity in the cardiovascular system is not strictly accurate, it may lead to an approximation that is sufficient for particular applications. As the output of a linear filter, ICP may be represented as a sum and/or the convolution product of one or more samples of ABP and V_mca, or other TCD-derived measurement(s) such as a tapped delay line in which two or more samples of data, usually with fixed sample interval, are considered simultaneously, with an impulse response vector. The impulse response vector is adjusted through well-known means (e.g., least-squares error minimization) so that the error produced by the operation is minimized when applied to the data gathered from real patients. This linear filter method has been adopted, with limited success, by prior investigators and is described, for example, in Schmidt B, Czosnyka M, Raabe A, Yahya H, Schwarze J J, Sackerer D, Sander D, Klingelhofer J, Adaptive non-invasive assessment of intracranial pressure and cerebral autoregulation, Stroke, 2003 January; 34(1):84-9.

Certain properties of the cardiovascular system are demonstrably non-linear. That is, they do not meet the linear systems criteria of scalability and superposition described by Hashizume, Y., 1988, "Non-linear Pressure Wave Propagation in Arteries," Journal of the Physical Society of Japan, Vol. 57, N12, pp. 4160-4168. For this reason, standard linear systems approaches such as frequency decomposition may not work sufficiently well in an analytical approach. These non-linear properties include the variation of the viscosity of blood with respect to shear rate and the visoelasticity of arterial walls, among others.

Non-linear Methodologies

We hypothesized that the non-linear features inherent in the cardiovascular system (non-linear viscoelastic characteristics of arteries and non-Newtonian fluid properties of blood, among others) would be best characterized using a non-linear systems analysis model. There are several non-linear analytical methods available that could be applied to the problem of probabilistic time series prediction in general and noninvasive ICP measurement in particular. These methods range from the use of Hidden Markov Models as described below and in Bengio Y., Markovian models for sequential data, Dept. Informatique et Recherche Operationnelle, NEC Research Institute Online Archive—http://citeseer.nj.nec.com and Support Vector Machines as described in Burges C., A tutorial on support vector machines for pattern recognition, Data Mining and Knowledge Discovery 1998; 2(2):1-47, to the use of Artificial Neural Network (ANN) analysis, also described below. Non-linear methodologies may be used, under some circumstances, with linear methodologies to provide non-invasive ICP determinations. ICP determinations maybe derived, for example, using a non-linear, empirically derived, relationship in combination with a linear first principles relationship.

A non-linear operation called a non-linear filter can be used to describe the relationship between ICP and related physiologic measurements including ABP and V_mca. Generally speaking, a non-linear filter is any operation for which the properties of scaling and superposition do not hold true. Therefore, each input to the non-linear filter has a unique output that cannot be described by the standard methods of linear systems theory. There are a number of means by which an empirical model may be constructed using non-linear filter theory.

Empirical relationships between the variable inputs discussed herein and the desired determination, such as ICP, may be derived using numerous mathematical techniques, including correlations, artificial neural networks, non-linear regression methodologies, Baysian statistical methods, artificial life methodologies, and the like. Exemplary techniques are described below.

Hidden Markov Model Prediction

Determination of ICP based on variable physiological parameters may also be thought of as a Hidden Markov Model (HMM), in which a system may be in one a finite set of states, hidden from the outside world, but which can be inferred from emissions, or observable phenomena, which are particular to each state. Such models are described, for example, in Boyer, X., Koller, D, Tractable Inference for Complex Stochastic Processes, Technical report, Stanford University, USA, 1998. The Bayesian probability of transition from one state to any other may be inferred from observing the emissions of a system over time. All relevant information about a system described by a HMM can be inferred from the current state of a system, rather than prior states the system may have adopted.

In this context, ICP can be thought of as taking on a finite number of unknown states (e.g. state 1 equals 1 mmHg, state 2 equals 2 mmHg, and so on), and minimally invasive or noninvasive measurements such as ABP or V_mca may be considered as emissions from which the state of the system (ICP value) can be inferred. This HMM system could be trained to calculate the probability of a transition from one ICP level to another based on experimental measurements. These probabilities can then be used to calculate the likelihood that the system is at a particular state, or ICP level, based on recent ABP and V_mca measurements.

Knowledge-Based Expert Systems/Artificial Intelligence/Heuristics, Fuzzy Logic

Although the relationship between ICP, ABP, and V_mca can be expressed in a mathematical form as a system of first-principles or empiric statistical equations, this relationship may also be expressed in the form of rules. Rules in this context may be if-then type decisions or continuous, probabilistic decisions (i.e. fuzzy logic) based on observable data. Such knowledge-based expert systems have been examined in the context of medical diagnostic decision support for some time and can reasonably be applied to the diagnosis of elevated ICP. Exemplary systems are described, for example, in Im EO, Chee W, Decision support computer program for cancer pain management, Comput Inform Nurs. 2003 January-February; 21(1):12-21, and McNeely M D, The use of expert systems for improving test use and enhancing the accuracy of diagnosis, Clin Lab Med. 2002 June; 22(2):515-28. Review.

For example, the following rule may be based on observations regarding the relationship between ICP, ABP, and V_mca:

if arterial pulse pressure <equals>'within normal limits'
and systolic BP<equals>'within normal limits'
and diastolic BP<greater than>'within normal limits'
and V_mca <equals>'significantly reduced flow'
and vasospasm criteria <equals>'not met'
then ICP <equals>'elevated'

Dozens or hundreds of such rules may be constructed based on empirical data or on the output of first-principles mathematical models. This approach may be used as the primary means to diagnose elevated ICP or as an adjunct method to classify results or predict the likelihood that specific pathologies might be at work.

Empirical Methods using ANN Training and Validation

One technique for modeling non-linear relationships uses an Artificial Neural Network (ANN) as a non-linear filtering system. These techniques are described, generally, in Maas W, Sontag E D, Neural systems as non-linear filters, Neural Comput. 2000 August; 12(8):1743-72.

For various reasons, an algorithm utilizing an ANN was chosen for deriving ICP predictions based on variable inputs of V_mca and ABP. Neural network analysis is a well-described and important signal-processing technique that has found a number of uses in the medical field, including voice recognition, radiologic image analysis, and physiologic signal processing. Exemplary techniques are described in the following articles: Boone J M, Sigillito V G, Shaber G S, Neural networks in radiology: an introduction and evaluation in a signal detection task, Med Phys 1990 March-April; 17(2):234-41; Lo S C, Li H, Wang Y, Kinnard L, Freedman M T, A multiple circular path convolution neural network system for detection of mammographic masses, IEEE Trans Med Imaging 2002 February; 21(2):150-8; and Sepulveda F, Cliquet Junior A, An artificial neural system for closed loop control of locomotion produced via neuromuscular electrical stimulation, Artif Organs 1995 March; 19(3):231-7.

An ANN is a mathematical construct inspired by the biological nervous system, in which connection weights between individual network units known as neurons determines the relationship between network input and output values. When designed with a sufficiently complex multilayer architecture and provided with non-linear activation functions (functions which determine the output value of a single neuron given a particular input value), ANNs can reproduce any continuous function with an arbitrary level of accuracy. Blum E, Leong K, Approximation theory and feedforward networks, Neural Networks 1991; 4:511-515.

ANNs have been shown to be of particular value in the prediction of time series data, as described by Elsner J B, Predicting time series using a neural network as a method of distinguishing chaos from noise, J. Phys. A: Math 1992 25:843 and Mozer M C, Neural net architectures for temporal sequence processing, In Weigend A and Gershenfeld N, editors, Predicting the future and understanding the past, Addison-Wesley 1993. ANNs have also been shown to be capable of learning to predict blood flow parameters from empirical data. Allen J, Murray A, Modeling the relationship between peripheral blood pressure and blood volume pulses using linear and neural network system identification techniques, Physiol Meas. 1999 August; 20(3):287-301.

ANNs are trained to simulate a given relationship between input and desired target or output values through exposure to a training set; that is, a set of data in which inputs are matched to known output or target values. During training, the error between known target values and actual ANN output is used in an iterative fashion to modify network connection weights so as to minimize network error. Following training, a validation (or test) data set similar to the training set but not used in network training is used to validate network performance. Through the use of statistically representative training and validation sets, an ANN can be produced which is likely to perform well when exposed to real-world input data. In an exemplary scenario, the training set would consist of inputs, containing data derived from ABP and V_mca measurements, and matched target values, containing data derived from invasive ICP measurements. A network trained on a data set suitably representative of the clinical population on which the filter is to be used would be able to predict ICP from future ABP and V_mca input data.

Alternatively, there are a number of methods (e.g. bagging, boosting, and stacking) by which the outputs of multiple neural networks, each trained on subsets of patients, may be combined for more accurate results. Exemplary methods are described in Brazdil P, Soares C, A Comparison of Ranking Methods for Classification Algorithm Selection, In Proceedings 11th European Conference on Machine Learning (ECML-2000): 63-74. For example, a series of networks may be each trained on a particular subclass of patients segregated on the basis of input parameters, ICP levels, or other characteristics. Analytical methods (for example, another neural network) may then be applied to input data from an unknown patient to determine how closely the input data of that patient matches each of the patient sets used to create the subset neural networks. The degree of match could then be used to determine how much each of these subset networks contributes to the final ICP prediction.

A methodology involving a particular neural network, represented by a unique combination of connection weights produced through training with a representative training set, may be fixed once it has demonstrated the ability to appropriately predict or simulate the invasive ICP recorded as part of a representative validation set not included in the training set. The network used in clinical practice may be fixed and, if fixed, would not undergo any changes with exposure to patients it encountered in practice. Alternatively, both experimental and commercial devices implementing a neural network to determine ICP may contain calibration network elements that are not fixed, but that facilitate individualized calibration of the device to a particular subject, or to a subset of subjects having certain characteristics, or to a subset of conditions having predetermined characteristics.

The components of one exemplary non-linear ICP prediction method and system implemented using an ANN are described below in the context of ongoing research protocols. The relationship between these variables was derived, in one embodiment, using a neural network and empiric analysis of data acquired from telemetry-monitored Neurosurgical ICU patients at Harborview Medical Center in Seattle, Wash. Results and patient ICP determinations are described below in Examples 1-3.

Preliminary Data Conditioning/Database Preparation

A significant amount of preparatory work was performed on raw physiological data gathered in the context of the current experimental protocol before it was used to determine ICP. The experimental work carried out to date has used a Spencer Technologies TCD100M Transcranial Doppler device (although alternative TCD equipment could equivalently be used), which does not have the capability to acquire physiologic data from study patients' ICU telemetry monitors (this includes ABP, iICP [invasively measured ICP], and other data important for ICP prediction). During the experimental phase, telemetry data was acquired separately using a notebook computer with a National Instruments 6024E PCMCIA data acquisition card. Methods and systems of the present invention are preferably integrated to provide data acquisition and processing of a variety of patient measurements.

Because multiple data records are preferably synchronized to facilitate processing, an important first step in data conditioning is the preparation of a monolithic, synchronized database file. Although telemetry and TCD data is initially acquired at differing rates, synchronized database file(s) for a given patient's data contains the data at a uniform rate. In one embodiment, a 250 Hz downsampled data rate is used because it contains nearly all important physiologic information and is industry-standard, in that it is commonly used by other investigators. TCD and telemetry data records conventionally contain an external synchronization signal which has been fed to both devices during data acquisition. The data may be synchronized through cross-correlation analysis and alignment of the digitized external synchronization signal stored simultaneously in both the TCD and telemetry data records.

Synchronized database files, such as 250 Hz database files, produced from each patient's data forms the basis of all further data preparation and analysis. Although the signals stored in the database are synchronized in an absolute sense, they remain out of phase with one another as a consequence of the physical locations in the body at which the measurements were generated. For example, the cardiac pulse does not reach the radial artery at the same time as it reaches the middle cerebral artery, so these signals will remain out of phase with one another even though they are synchronized with respect to time. This discrepancy is taken into account during building of the training set, described below. The particular form in which data is stored is arbitrary, although the experimental database format was designed to allow data to be easily imported into Matlab, a commercial computing environment designed for algorithm development.

Neural Network Design

There are numerous means by which ANN software may be prepared and almost a limitless array of possible network topologies which might be selected for use in the methods and systems described herein. For our initial research, we used a relatively simple and well-known network topology. ANN software and network topologies other than those described below may be used in methods and systems of the present invention and are know to those having ordinary skill in the art.

A non-linear multilayer perceptron (a 2-layer feed-forward ANN) was chosen as the experimental prototype architecture for its well-known characteristics and relatively straight-forward training process. This system is described in the following publications: Elsner J B, Predicting time series using a neural network as a method of distinguishing chaos from noise, J. Phys. A: Math 1992 25:843; Møller M F, Efficient training of feed-forward neural networks, PhD thesis, Computer Science Department, Århus university 1993; Riedmiller M. Advanced supervised learning in multi-layer perceptrons—from backpropagation to adaptive learning algorithms, Computer Standards and Interfaces 1994; 16:265-278; and Saarinen S, Bramely R, Cybenko G, Ill-conditioning in neural network training problems, SIAM J Sci Comp 1993; 3:693-714. The hidden neuron layer utilizes an approximation of the hyperbolic tangent function as a transfer function, which allows the network to model non-linear input-target relationships; the output neuron layer uses a linear transfer function so that network outputs can be linearly scaled. Network inputs consist of normalized, arbitrary-duration tapped delay-lines of invasive ABP and Doppler ultrasound V_mca data in which each input contains pulse-contour data from one or more cardiac cycles. Network output represents a continuous ICP pulse contour normalized to the duration of one cardiac cycle.

Network input, hidden layer, and output size is somewhat arbitrary and the best configuration for a given problem must often finally be determined through trial-and-error. In one embodiment, the system of the present invention employs an ANN with an input size of 42 samples (20 ABP pulse-contour samples, 20 V_mca pulse-contour samples, 1 instantaneous heart-rate value, and 1 value representing the measured static pressure difference between the invasive arterial line and the middle cerebral artery), a hidden layer consisting of 5 neurons, and an output layer consisting of 20 ICP pulse-contour samples. Alternative input data formats include non-invasive blood pressure (derived through cuff, tonometric, or other means) which is represented as systolic, mean, and diastolic pressure values that are updated intermittently.

Good preliminary results were achieved without considering additional patient information that would highlight differences in blood viscosity and shear resistance, such as hematocrit. However, this and other patient information was collected and may be analyzed to provide accurate ICP predictions for specific subgroups of patients, such as those who have undergone massive fluid resuscitation following trauma, or those with polycythemia or other causes of blood hyperviscosity.

Although a relatively simple (yet powerful) neural network architecture was chosen for the initial analysis, there are a number of alternative network topologies that would also be suitable and may provide improved performance. One example of particular interest is the family of topologies known as Recurrent Neural Networks (RNNs), such as those described by Elman (supra) and other investigators, including Giles C, Lawrence S, Tsoi A, Noisy time-series prediction using a recurrent neural network and grammatical inference, Machine Learning 2001 July/August; 44(1):161-183. This family of topologies maintains an internal memory of previous network inputs and/or outputs for improved time-series prediction. Rather than relying on a finite tapped delay-line input, RNNs can maintain an infinite impulse response. RNNs present training challenges, as described in Atiya A, Parlos A, New results on recurrent network training: unifying the algorithms and accelerating convergence, IEEE Trans. On Neural Networks 2000 May; 11(3), but they are promising and would be suitable for use in methods and systems of the present invention.

Neural network software designed as part of this research program was implemented in Matlab 6.5 using portions of the Mathworks Neural Network Toolbox, a commercial neural network computing package used extensively in industry.

Preparation of Training Set Data

The format of the data presented to the ANN is somewhat arbitrary, provided that data from multiple sources is synchronized. In one embodiment, synchronized 250 Hz data undergoes transformation from the time-domain to the pulse-domain and is presented to the network as a series of pulse-contours represented by a fixed, arbitrary number of data points normalized to the duration of one or more cardiac cycles. Many other implementations are suitable, and several have been tried with varying results. The pulse-domain implementation presented here has been the most effective of the methods tried. It is important to understand that the data presented to the network is essentially absolute-valued pressure and flow data (following a linear scaling), and can therefore be used to track and predict absolute ICP values.

The process by which pulse-domain transformation and input/target set building occurs is straightforward but somewhat involved. The process is generally done in a piecemeal fashion so that a manageable amount of data is handled at any one time (e.g. 30 seconds of data may be processed at a time). The steps are as follows:

(1) Phase synchronization—As mentioned earlier, the database record is synchronized with regard to absolute acquisition time, but contains cardiac-cycle phase discrepancies between signal records. The first step in training set preparation is to align ABP, V_mca, and ICP records (e.g. with cross-correlation spectrum analysis and alignment) so that they are in phase with regard to cardiac-cycle boundaries. This results in multiple records, one for each physiologic signal, that are in phase with one another.

(2) Cardiac cycle delineation—The location in time of systolic and diastolic peaks and minimums, which define the boundaries of each cardiac cycle, must be determined for either the ABP or V_mca 250 Hz linear record. Since both records can be assumed to have simultaneous cardiac cycle boundaries once the phase discrepancy between signals has been addressed, examination of one of these records is sufficient for pulse-domain transformation of both. In the case of an invasive ABP contour, which is generally smooth and continuous, location of the cardiac cycle boundaries is a simple process involving the algorithmic detection of local minima and maxima through analysis of $1^{st}$ and $2^{nd}$ derivative curves. In the case of the V_mca record, which may contain a significant amount of noise, cardiac cycle boundaries can be similarly gleaned from the flow record after it has been passed through a low-pass digital finite impulse response (FIR) filter (it has been found that a 4-Hz LPF of order 50 is sufficient for most records) or following smoothing by other means. In addition, since V_mca and ABP are largely synchronous once phase shift has been accounted for, the pulse boundaries of the V_mca can be assumed to be identical relative to the ABP record. Each of these methods works well on real-world data. FIG. 1 shows exemplary output from the pulse boundary calculation used to delineate the beginning and end of each cardiac cycle, with the upper trace representing the ABP signal and the lower trace marking systole (positive-going) and diastole (negative-going).

(3) Resampling and transformation—After cardiac cycle boundaries are recorded, the data in each linear signal record from each subsequent cardiac cycle is isolated and resampled using standard signal-processing techniques such that it occupies a fixed, arbitrary number of data points. Experimental work was carried out with a pulse-domain width of 20 samples, although other pulse domain widths would be operative and suitable. Following resampling and transformation, each signal can be thought of as occupying a two-dimensional array in which each successive column contains successive pulse beats normalized to a fixed pulse-domain width.

(4) Moving window Doppler envelope—Although successive resampled ABP pulse beats derived in this way generally represent smooth continuous data that is appropriate for presentation to a neural network, V_mca flow data as it is currently gathered contains noise and is best represented as a pulse-envelope over a moving window of time. In other words, each point in pulse-time (a particular sample index in a given normalized pulse) can be considered to be best represented by the maximum Doppler velocity occurring in a window of arbitrary width of successive normalized pulse beats. This moving window process then "fills in" the missing data in each V_mca pulse as it produces the flow envelope, allowing each V_mca pulse record to contain time-smoothed information. The V_mca pulse-domain flow-envelope process we implemented was designed for use with the Spencer TCD100M internal autocorrelation phase-velocity calculation. This part of the methodology may not be necessary in alternative embodiments of methods and systems of the present invention in which V_mca flow data is acquired in alternative ways or using different types of Doppler devices.

(5) Normalization—Each signal record now occupies a phase-domain array, in which rows represent cardiac-cycle normalized 'fast time' and columns represent pulse-to-pulse 'slow time'. However, signal values are still in real units. Neural networks operate best when input data falls within a relatively narrow range (e.g. −1 to 1), so the data at this stage must be normalized between defined extremes (e.g. physiologic values likely to be encountered in clinical use). Because these normalization extremes are fixed, the normalization operation represents a reversible transformation. This means that although the input values have been rescaled, they still represent absolute values.

(6) Concatenation of elements—Each input vector preferably contains elements of each signal record (ABP and V_mca), so the normalized pulse-domain elements from step 5 are concatenated to one another. Finally, instantaneous heart rate and static pressure head measured between the site of blood pressure measurement and the MCA is concatenated to each input vector. The data may be concatenated within or across multiple cardiac cycles, or may be normalized to other cyclical (or non-cyclical) physiological events. These values may not be necessary, but they may improve network performance. The input records are now complete.

Figure 2:
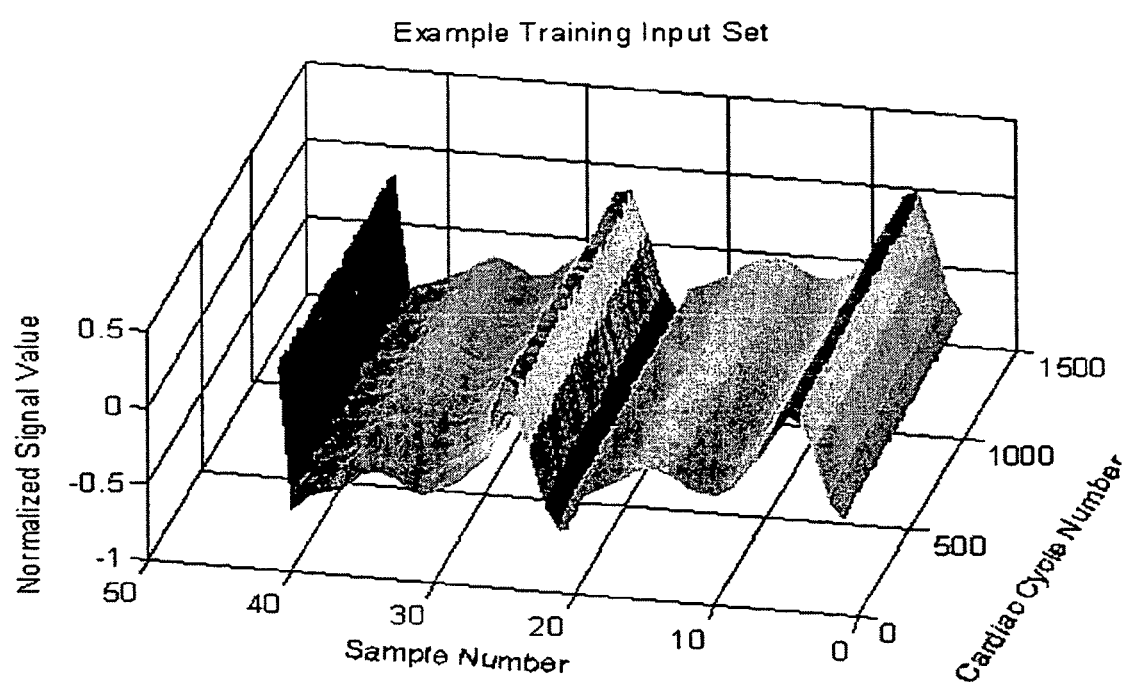
FIG. 2 shows an example of a training set for a given patient using an ANN as described below. There are approximately 1500 individual cardiac cycle records displayed pulse by pulse. Each input vector record has 42 values and is made up of an ABP pulse, V_mca Pulse, instantaneous heart rate, and static pressure difference, concatenated together.

(7) Preparation of matched target records—For training to be successful, each input vector in the training set must have a matched target vector. The current implementation defines the target vector as one or more cardiac cycles of ICP data resampled to a fixed number of values. The ICP data is therefore normalized in time, but since it is synchronous with the input data, the ICP pulse can be stretched or shrunk using the original heart rate data stored in the input set so that it represents a realistic ICP pulse contour. The target set is built at the same time as the input set, and undergoes each of the steps above except for step 6, since target vectors do not currently contain any additional information beside ICP. Exemplary data from a training set for a patient is illustrated in FIG. 2. There are approximately 1500 individual cardiac cycle records displayed pulse by pulse. Each input vector record has 42 values and is made up of an ABP pulse, V_mca Pulse, instantaneous heart rate, and status pressure measured between the site of V_mca and ABP measurement, concatenated together.

Pulse domain input and/or target data can be stored to disk or created in real-time from telemetry and Doppler flow data. Patients representative of those likely to be encountered in clinical practice (by virtue of ICP, gender, ethnicity, pathology, etc.) are selected to populate the training panel. Each of these patients' 250 Hz database(s) (or the equivalent linear records stored in memory) undergoes training set preparation and is included in the set of input-target vectors that are presented to the neural network during training.

Training Methods

In general, ANNs are trained through exposure to a well-defined data set representative of that likely to be encountered in real-world practice. In a naive network undergoing training, error between network output and known target output is passed to a training algorithm, which adjusts network connection weights in order to minimize error. Over successive iterations of training set presentation and training algorithm connection weight adjustment, network error is minimized.

Proper selection of the network training methodology is important, because it may influence both the efficiency and accuracy of ANN training. There are constraints that may play a role. Certain types of network problems may respond differently to different training methodologies; the size of the network and/or training set mandates practical memory and processing requirements that must be met if training is to be successful; and the "goodness of fit" following training may be susceptible to a number of other related parameters, including the quality (i.e. how well the training set data has been prepared) and appropriateness (i.e. level to which training set data is representative of data likely to be encountered in practice) of training set data.

We implemented the most robust and well-described training methodology that met the computing resources available. For this reason, training was carried out using Scaled-Conjugate Backpropagation methodology as described in Møller M F, A scaled conjugate gradient algorithm for fast supervised learning, Neural Networks 1993; 6:525-533. This methodology has been demonstrated to perform well for a wide variety of ANN architectures and problems and has modest memory and processing requirements. It is important to remember that a number of other training methods may alternatively be used, although the aforementioned constraints apply. Other training algorithms that may be used include, for example, Resilient Backpropagation, as described in Riedmiller M, Braun H, A direct adaptive method for faster backpropagation learning: The RPROP algorithm, Proceedings of the IEEE International Conference on Neural Networks, 1993, the Fletcher-Reeves Conjugate Gradient, as described in Fletcher R, Reeves C, Function minimization by conjugate gradients, Computer Journal 1964; 7:149-154, and the Levenberg-Marquardt methodology described in Hagan M, Menhaj M, Training feedforward networks with the Marquardt algorithm, IEEE Trans. on Neural Networks 1994 November; 5(6):989-993, among others.

Assessment of the optimum level of training is an important and quantifiable process. The training error should usually be the minimum achievable level of error. This is a valid assumption as long as the network is not "over-powered" (possessing more hidden nodes than necessary) and will not over-fit the data. An excellent discussion of this problem is given by Caruana et al. in Caruana R, Lawrence S, Giles C, Overfitting in neural nets: backpropagation, conjugate gradients, and early stopping, Neural Information Processing Systems, Denver Colo. 2000 Nov 28-30. To avoid this problem, a number of different networks with varying numbers of hidden nodes and varying degrees of training must be used and the results of the validation input set compared to the known validation ICP target data. For example, networks with 5, 10, 15, 20, and 25 hidden nodes may be trained for 500, 1000, 1500, 2000, 2500 and 3000 epochs. Analysis of the validation set error produced by each network delineates which architecture is the suitable for the given training and validation set. Threshold values for the validation set error (i.e. acceptable levels of ICP error) will continue to be refined as the clinical requirements and capabilities of methods and systems of the present invention are further developed.

An additional aim of the experimental process was to identify subgroups of patients which may share common noninvasive ICP measurement characteristics (e.g. on the basis of vascular properties) and which may be identified on the basis of ABP or TCD characteristics (e.g. hypertension, vasospasm), mechanism of injury, physical exam or laboratory findings, patient demographics (e.g. age, sex, weight), or a combination of these parameters. It is likely that such subgroups exist (e.g., segregation of patients with subarachnoid hemorrhage as those likely to encounter some degree of autoregulatory dysfunction), and it is reasonable to suggest that a network specifically trained for the purpose of non-invasively measuring ICP in a particular group may have better response characteristics when confronted with unknown patients that segregate to that group than a network trained on all patients.

We are currently developing methodologies for identifying subgroups of patients based on noninvasive data including $V\_mca$ and ABP characteristics, and to segregate the training data for these patients for networks designed to carry out subgroup analysis. One method utilizes the Principal Component Analysis as described in Jolliffe, I T, Principal Component Analysis, Springer, Verlag 1986, to identify the most important orthogonal dimensions of the input set and to identify the Euclidean distance of each unknown patient's input data set from the center of gravity of each training set patient or subgroup. Each training set subgroup's network is then weighted according to the inverse of the relative distance.

A different version of Principal Component Analysis that may be used in determining ICP based on measured variable parameters, or for subgroup analysis, is described in Stewart, I, Regime change in meteorology, Nature Vol. 422, 10 April 2003, Cromellin, D, Non-linear dynamics of atmospheric regime transitions, Thesis, Univ. Utrecht (2003) and Cromellin, D, J. Atmos. Sci 59, 1533-1549. Using these techniques, the principal components or common patterns, referred to as empirical eigenfunctions, are identified in real data and are then used in association with prognostic equations to track the temporal evolution of the components.

Another method uses a Kohonen Self-Organizing Map (SOM) as described in Kohonen T, Self organizing maps, Second Extended Addition, Springer, Springer Series in Information Sciences 1997. This methodology uses an unsupervised type of neural network closely associated with biological memory in which differing network inputs are mapped to unique regions of a dimensionally-reduced output space. In this scheme, unknown patients' data would map to regions of the SOM representing input characteristics most similar to a particular patient or subgroup of the input set, and the network trained on that data would be chosen to non-invasively predict ICP. These methods are expected to improve noninvasive ICP determination in specific patients or subgroups of patients with vascular parameters differing appreciably from the majority of patients in the training set.

The methods described above for neural network training preferably result in one or more fixed methodologies for predicting ICP based on individual patient input and variables. Systems and methodologies of the present invention comprehend both the experimental systems and methodologies used to derive relationships between variable parameters such as $V\_mca$ and/or ABP and ICP, such as neural networks that undergo training and validation, as well as clinically useful and commercial methodologies and systems implementing one or more fixed methodologies for determining ICP based in individual patient data resulting from neural network training and validation.

Validation of Network Performance

Validation of the network performance is achieved by presenting validation or test data from one or more patients (patient data identical to training set data in that invasive ICP and ABP are known, but which has not been included in the training set) to the ANN and comparing the subsequent predicted ICP output to the test patients' known or target invasive ICP. Analysis of algorithmic performance with this validation set helps predict how the algorithm will perform with patient data likely to be encountered in clinical practice.

Assessment of Network Stability, Appropriateness of Input Data

Since the validated neural network methodology forms the heart of an instrument which has the potential to alter patient management, it is important that the stability and reliability of this algorithm be well established. The neural network employed as part of the research described above may be configured to be perfectly stable, in that its connection weights are fixed and are not influenced by the type or order of data presented to its inputs.

The response characteristics of the final methodology must be carefully delineated. One stage of this characterization is through network validation, described above. A second stage is through the relatively straightforward step of input space mapping, in which thousands of canonical inputs encompassing the input set likely to be encountered in clinical practice (e.g. ABP waveforms throughout the physiologic range in increments of 1 mm Hg, each with $V\_mca$ waveforms throughout the physiologic range in increments of 1 cm/s) are presented to the validated network, and the resultant ICP outputs recorded. This process characterizes the network response over the entire input space likely to be encountered. Such input-mapping highlights any problem areas in terms of input space response, and checks the physiologic ranges over which the network can be expected to perform adequately.

Figure 3:
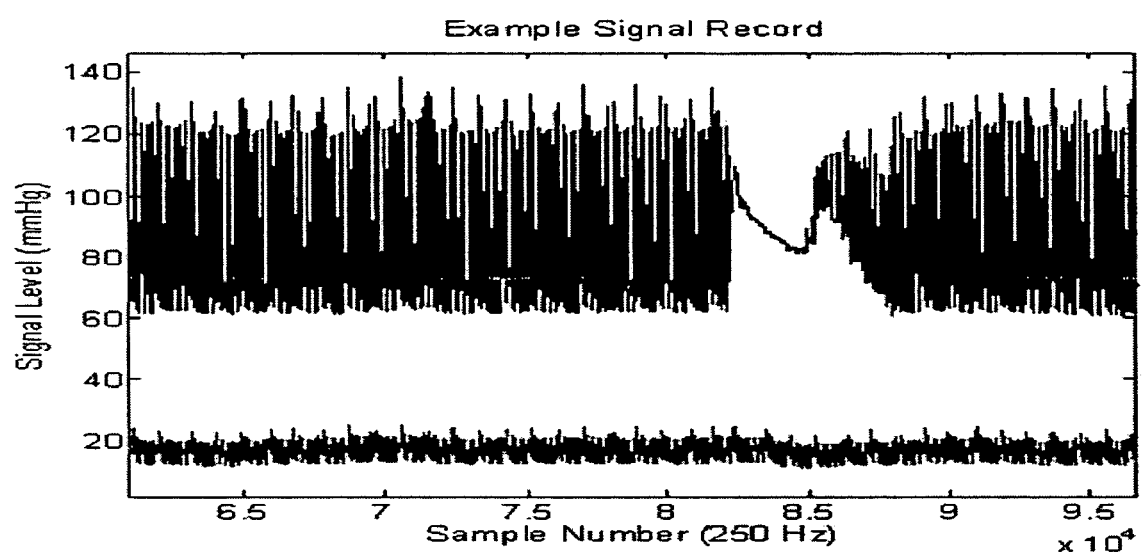
FIG. 3 shows an exemplary signal record produced by patient manipulation during data acquisition. The ABP record (the upper trace) shows evidence that this patient has undergone a blood draw from the arterial line. The invasive ICP trace (lower trace) is not affected.

One important aspect of the foregoing description is that in this methodology, as in any other, the appropriateness of the input (and target) data must be safeguarded. "Bad data" must be thrown out prior to training, as well as prior to ICP prediction using input data from an unknown patient. FIG. 3 shows an example of a signal record produced by patient manipulation during data acquisition. The ABP record (upper trace) shows evidence that this patient has undergone a blood draw from the arterial line. The invasive ICP trace (lower trace) is not affected. Most disruptions that occur during data acquisition are similarly obvious, lending themselves to automated detection.

This data monitoring and safeguarding process may be implemented in any of a number of ways. In one embodiment, the patient's ABP and ICP data collection devices (e.g.) transducers may be recalibrated prior to and monitored continuously during data acquisition, with the time and duration of any manipulation during data acquisition (e.g. blood draw) being recorded. Once data acquisition is complete, the database record entries corresponding to these recorded times of patient manipulation may be marked for exclusion from training set data. Following this step, the synchronized (e.g. 250 Hz) database records may then be inspected (e.g. visually or computationally) for V_mca, ABP, and ICP curve abnormalities (e.g., significant blunting suggesting arterial line malposition and V_mca dropout from a malpositioned data acquisition device). Any abnormal records are marked for exclusion from training set data. Signal values that do not remain in the expected physiological ranges are also excluded. Manual data checking and/or automated software methods may be implemented. The data-checking function is preferably implemented as a fully automated software process.

A final note regarding data processing and safeguards involves the issue of real-time ICP output characterization. ICP data output derived using the methodology described above can be characterized in a number of ways to ensure that relevant physiological values are conveyed to the user. These include methods to assure that the range and rate of change of the ICP waveform is physiologically reasonable (e.g. noninvasive ICP should be a positive value less than 75 mmHg), that the ICP pulse shape, height, and other parameters are realistic, and that there is a reasonable degree of concordance between the forcing functions inherent in the system (ABP and V_mca) and the system output (ICP).

Neural networks can be considered to operate using Bayesian probability estimates, and can therefore also provide a measure of confidence in a given ICP prediction, a capability that has been utilized in other medical signal processing tasks, as described in Dorfner G, Can neural networks improve signal processing? A critical assessment from the ANDEE project, NEC Research Institute Online Archive—http://citeseer.nj.nec.com/186775.html. Providing high and/or low confidence values allows the instrument and/or the health care provider to give particular weight to the predicted ICP value or to discard it, or to prompt the provider to make sure that all sensors and lines are properly attached to the patient.

Implementation of a Clinical System for Predicting ICP based on ANN Methodology

The various components of an ICP prediction methodology, as implemented in ongoing research protocols, have been outlined above. When implemented in a clinical system, the methodology may be simpler, since real-time ICP data is critical to clinical usefulness. The following features are considered important in implementation of a clinical methodology and system:

(1) Acquisition of ABP and V_mca data. ABP and V_mca data are preferably acquired and processed in an integrated electronic device and may therefore be conveniently synchronous with respect to acquisition time, eliminating the need for data synchronization. In other embodiments, ABP and V_mca may be acquired using different devices and/or synchronization rates, with the data being collected and processed in an integrated processing unit that provides data synchronization, as necessary.

(2) Downsampling/resampling of telemetry and Doppler flow data. This allows each linear signal record to occupy the same amount of space so that standard signal processing techniques may be employed more easily.

(3) Data cleaning. This ensures that all signal records are continuous, within expected physiologic ranges, and appropriate for further processing.

(4) Phase alignment of cardiac cycle boundaries. Although the acquisition of telemetry and Doppler flow data by the same device facilitates synchrony with regard to acquisition time, the input data may be out of phase with regard to cardiac cycle boundaries. In order for pulse-domain transformation to be carried out successfully, these records will require alignment, such as through cross-correlation spectrum analysis or other methodologies.

(5) Pulse domain transformation. Transformation of the linear, phase-aligned, time-domain telemetry and Doppler flow records to two-dimensional, normalized pulse-domain records may be desirable. This is a multi-step process and may involve calculation and storage of beat-to-beat instantaneous heart rate, normalization of each cardiac cycle to a fixed number of samples, and moving pulse-window smoothing or envelope calculation for the V_mca Doppler flow data.

(6) Presentation of pulse-domain input data to a fixed, validated network. This is the calculation step of the algorithm, in which a network that has been previously trained is used to accurately determine the ICP of an individual patient given that patient's acquired input data, such as telemetry data and TCD information. In a clinical system, no training of the system's network occurs. The network in a clinical system is fully trained and validated, and all connection weights are fixed. It is at this time that any subgroup segregation should occur.

(7) Inverse pulse-domain transformation and rescaling. The raw data output from the trained and validated network is a pulse-domain record normalized to lie on the interval [−1, 1]. This record must be transformed to a linear time-domain record, which may be achieved, for example, by resampling each pulse to represent its original duration and then concatenating linearly to the pulse before it. The resampled pulses are then rescaled to physiologic signal levels.

(8) Trend analysis and data display. Systems of the present invention for determining ICP preferably provide trend analysis and data display features. One suitable output display provides: (1) one or more trace(s) of ICP over a "long term" period of time of at lest several minutes and up to several hours or days to illustrate trends in patient ICP; (2) a trace of "instantaneous" or "short term" ICP, determined over several cardiac cycles; and (3) additional graphical representations that may aid in guidance of an acoustic transducer or transducer array, as described below. In addition, a representation of flow velocity vs. depth of the transducer focus may be provided. A display showing both instantaneous ICP determinations over fewer than ten (10) previous cardiac cycles and ICP determinations over a period of at least several minutes is preferred. It will be evident to one of ordinary skill in the art that data may be displayed in a variety of ways.

Using an ANN, as described above, is a convenient and reliable technique for deriving an accurate non-linear relationship between patient input variables, such as V_mca and ABP and the determined output, ICP. We expect that, using an ANN, we can also derive an accurate non-linear relationship between a single patient input variable, such as V_mca, and the determined output, ICP, using analysis of one or more specific features of the V_mca data. Other types of empirical methods may also be employed and are described below.

Determination of ICP using Cellular Automata

The relationship between ICP, ABP, V_mca, and/or other physiological measurements may be modeled as a cellular automaton (CA). CAs are mathematical constructs in which a regular, discreet lattice of cells, each of which can adopt one or more of a finite set or continuous range of states, evolve over successive discrete time steps according to specific rules regarding each cell's state and the state(s) of that cell's neighbor(s). Using CA's and similar modeling techniques, the propagation of natural phenomena through time can be modeled in reproducible ways that do not require extremely complex mathematical description. Exemplary techniques are described in Smith M A, Cellular Automata Methods in Mathematical Physics, PhD Thesis, Massachusetts Institute of Technology, May 1994.

The propagation of the CA model may then be used to produce statistical or expert systems describing the predicted behavior of the physical system after which the CA has been modeled. In the case of ICP prediction, for instance, a simple one-dimensional system of cells whose internal states describe blood flow or ABP and/or another physiological property, may be used to model the propagation of the cardiac pulse through the cerebral vasculature over time. The propagation rule may take into account physical factors such as the elastance of the arterial wall, the viscosity of blood, central venous pressure, the level of ICP, and other properties that could influence blood flow. By modifying the ICP parameter so that the blood flow pattern predicted by a given CA matches the physically observed pattern, ICP in a particular patient may be predicted accurately.

Determination of ICP using First Principles

First Principles Methods

Determination of ICP based on related physiological parameters measured using non-invasive or minimally invasive techniques may also be approached using first-principles methods based on non-linear relationships, or on linear differential equations. Such a system may be represented in the form of a more commonly encountered engineering system, such as an electrical transmission line, to which appropriate techniques from electrical engineering analysis may be applied and a closed form solution obtained, as described in Ursino M, Lodi C A, Interaction among autoregulation, $CO_2$ reactivity, and intracranial pressure: a mathematical model, Am J. Physiol. 1998 May; 274(5 Pt 2):H1715-28.

Alternatively, linearized equations, in which non-linear terms are neglected or modified to simplify the solution, may be derived from non-linear fluid dynamics equations (e.g. Navier-Stokes equations), and the closed form solution obtained or solved numerically, as described in Olufsen M S, A one-dimensional fluid dynamic model of the systemic arteries, Stud Health Technol Inform. 2000;71:79-97. ICP is an important variable in any reasonably inclusive system of derived equations describing cerebrovascular fluid mechanics, and may be solved for given ABP, V_mca, and/or other physiologic data.

An exemplary linear first-order differential equation model of the cerebral vasculature was developed using invasive ABP, invasive ICP, and V_mca signals. In this system, the radial artery ABP signal was taken as a surrogate for the ABP at the inlet of the MCA. Flow is presumed to be primarily resistive. Jugular venous pressure at the cranial outlet (JVP) is taken as the true outlet pressure of the cranial vasculature and is assumed to be zero. We have found, experimentally, that this assumption is generally appropriate for most patients without cardiac disease who are in a supine position with a 30 degree flex at the hips so that the head is significantly above the heart. ICP is assumed to act according to the $3^{rd}$ pressure principle, such that ICP acts in lieu of JVP as cranial outlet pressure to define the pressure drop between the cranial inlet and outlet.

Each patient is assumed to have a characteristic vascular resistance, k, that is unknown initially but that can be calculated from physiologic data. In particular, the heart is treated as a step-function generator with a given pulse height and resultant flow impulse response. The relationship between these two quantities determines k. Volumetric flow is assumed to be directly proportional to V_mca. Finally, ICP is calculated as the required cranial outlet pressure given MCA inlet pressure, characteristic resistance k, and volumetric flow derived from V_mca.

Figure 4:
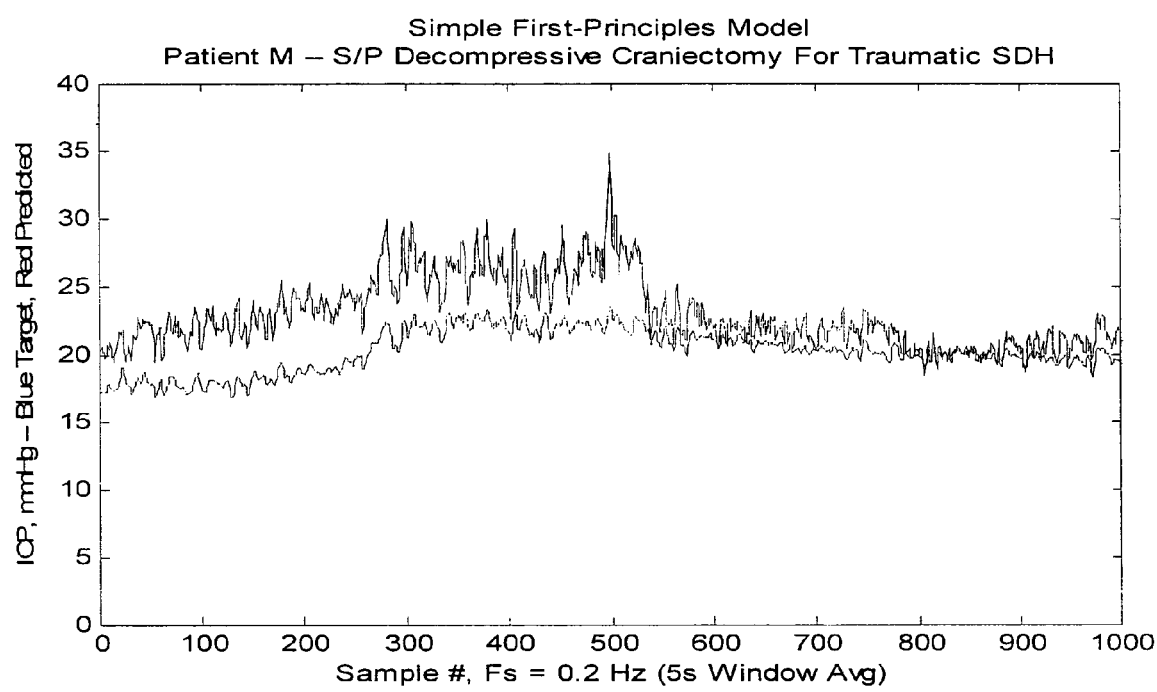
FIG. 4 shows the predicted ICP (lower trace) compared to measured ICP (upper trace) based on the simple mathematical first principles model described below.

This simple exemplary method utilizes intrinsic blood pressure and flow manipulations generated by the heart to determine the characteristics of the cerebral vasculature, which are then used to predict ICP. FIG. 4 shows the predicted ICP (lower trace at left axis) compared to invasively measured ICP (upper trace at left axis) based on the simple model described above that captures the step-down in arterial blood pressure as it enters the brain, with resistive, viscous flow in the middle cerebral artery, and the heart modeled as a step-function generator such that changes in arterial blood pressure lead to changes in cerebral blood flow. This particular model was driven using the systolic and diastolic values of arterial blood pressure and flow in the middle cerebral artery to predict ICP.

In one embodiment, first principles methods such as those described above are used in combination with an empirical approach, such as a neural network approach, to make ICP determinations non-invasively using acoustic scatter and/or ABP data. First principles methods may be applied to patient data in the first instance to make a preliminary ICP determination, with empirical methods used on all or a portion of patient data to make corrections to or adjust or refine the preliminary ICP findings.

It is also possible for extrinsic manipulations (e.g., blood pressure cuff inflation, pharmacological treatment) of any of these parameters to be used to determine the characteristics of the cerebral vasculature in a similar fashion, as described in Vavilala M S, Newell D W, Junger E, Douville C M, Aaslid R, Rivara F P, Lam A M, Dynamic cerebral autoregulation in healthy adolescents, Acta Anaesthesiol Scand. 2002 April; 46(4):393-7.

Non-linear Numerical Methods

The relationship between ICP, ABP, V_mca, and/or other physiological measurements may alternatively or additionally be modeled using well-known methods (e.g. finite element analysis) that allow the numerical solution of discretized versions of the Navier-Stokes equation, which describes the dynamics of fluid mechanical systems such as the cerebral vasculature. This type of modeling is described in Ma X, Lee G C, Wu S G, Numerical simulation for the propagation of non-linear pulsatile waves in arteries, J Biomech Eng. 1992 November; 114(4):490-6. Solution of the Navier-Stokes equation allows one to take many of the non-linear properties of the cardiovascular system into account, including non-linear arterial viscoelasticity, convective momentum and, potentially, non-Newtonian viscosity.

An important part of such an approach is the acquisition of physical parameters describing the specific cerebrovascular system(s) to be modeled. As computing and imaging resources continue to dramatically improve, one might imagine scanning the entire three-dimensional cerebral vasculature of a patient non-invasively (e.g. with MRI or CT angiography), modeling the fluid mechanics numerically (as described, for example, in Cebral J R, Yim P J, Lohner R, Soto O, Choyke P L, Blood flow modeling in carotid arteries with computational fluid dynamics and MR imaging, Acad Radiol. 2002 November; 9(11):1286-99), and deriving ICP from this first principles model. With limited computing resources, a simplified "average" vascular tree, with an arbitrary number of vascular bifurcations, could be used as the basis for a model for specific subtypes of patients and used to calculate ICP from other measured physiologic parameters.

Determination of ICP using a Combined Empirical/First Principles Approach

First principles methods may be applied to patient data in the first instance to make a preliminary ICP determination, with empirical methods used on all or a portion of patient data to make corrections to or adjust or refine the preliminary ICP findings, as described above. Other combinations of empirical and first principles approaches may also be used, and exemplary methods are described below.

Correlation of Non-Invasively Measured Spontaneous Tissue Displacement with ABP and ICP One method uses a derived relationship between spontaneous (intrinsic) tissue displacement (resulting from blood flow, CSF, etc.), determined by analyzing acoustic scatter from a CNS target tissue site, ABP, and invasively monitored ICP to determine ICP based upon invasively or non-invasively measured tissue displacement and ABP. V_mca may be used instead of, or in combination with, measured tissue displacement as variables using a combined empirical/first principles approach.

In one embodiment, using an ultrasound probe operating above 100 kHz, a given volume of tissue is insonated with a waveform having a specific frequency and amplitude, and the time or phase shift of a reflected ultrasound signal is used to calculate intrinsic tissue displacements. The equation that relates time or phase shift to tissue displacement is: $d=t*1500$ m/sec, where d=tissue displacement, t=the time or phase shift of the reflected signal, and 1500 m/sec is the estimated speed of sound through the brain. Since ICP=CPP−MAP, where MAP=(2*diastolic ABP+systolic ABP)/3, and d=F(CPP), where F can be any function, such as an exponential, vector, matrix, integral, etc., or a simply an empirical relationship with CPP, CPP=MAP−ICP=$F_2$(d), where $F_2$=$F^{-1}$. $F_2$ is determined empirically by taking measurements from a variety of patients under various circumstances, and the determination of displacement and ABP can then be used to calculate ICP, where ICP=$F_2$(d)−MAP.

Correlation of ICP with Amplitude of Acoustic Tissue Signal

This method uses a derived relationship between the amplitude of reflected acoustic signal(s) from CNS target tissue sites, ABP, and invasively monitored ICP to estimate ICP from non-invasively measured acoustic signals and ABP. Using an ultrasound probe operating above 100 kHz, a given volume of tissue is insonated with a waveform having a specific frequency and amplitude, and the amplitude of the backscatter is used to create a waveform of tissue reflection/absorption. This new waveform, α, can be generated by integrating the amplitude of the backscatter over a finite epoch (such as the cardiac cycle, measured with ECG tracing) and normalizing this by the time period of the epoch. Since the backscatter signal is related to the arterial pulse wave, α can be normalized to the MAP (as defined above), to produce a waveform β. The relationship between this normalized waveform, β, and invasively measured ICP is then determined by taking simultaneous measurements of the backscatter signal, ABP, and ICP and solving for the equation ICP=F(β), where F is any mathematical function, or simply an empirical relationship. Once F is established (by means of multiple empirical measurements from a variety of patients under various, known conditions), the non-invasive determination of β by the noninvasive determination of tissue displacement and noninvasive determination of arterial blood pressure can be used to calculate ICP.

Correlation Between Peak Backscatter Amplitude and ICP

In a manner similar to that described above, the peak amplitude of the backscatter signal over a given epoch (e.g., cardiac cycle) can be normalized by the MAP over the same epoch, producing a value, *, and this related with simultaneous invasive measurements of ICP to generate a relationship, ICP=F (*), where F is a mathematical or empirical relationship between * and ICP.

Many attempts have been made to infer ICP and/or autoregulation status using standard transcranial Doppler (TCD) data. In another embodiment, methods and systems of the present invention use existing methods for determining ICP, based on standard TCD measurements, replacing noninvasive measurements of V_mca with noninvasive measurements of the displacement of CNS tissue caused by blood flow, the cardiac cycle and respiration, or by combining one or more variables, including V_mca, tissue displacement, and other physiological variables. One such example is provided below, based on the work of Schmidt, B., et al., Noninvasive Prediction of Intracranial Pressure Curves Using Transcranial Dopper Ultrasonography and Blood Pressure Cures, Stroke Vol. 28, No. 12, December 1997. The processing steps of the present invention utilize simultaneous and continuous measurements of invasive ICP, invasive or noninvasive ABP, and displacement (or the like) to generate a set of equations that accurately predict ICP using only non-invasively-determined displacement and ABP data alone. Flow velocity and tissue displacement may replace the ABP measurement.

Step 1: A weight function is calculated between ABP and ICP, using a system of linear equations. The solution of this system of equations results in a vector containing the coefficients of the weight function. Any number of coefficients can be chosen to model this system. For example, we will select 25 coefficients. For any given weight function ($f_0, f_1, \ldots, f_{24}$), the ICP value at point k in the time sequence can be computed by the values of the AP recorded at time k−24, k−23, . . . , k−1, k according to the formula $ICP_k = f_0*ABP_k + f_1*ABP_{k-1} + \ldots + f_{23}*ABP_{k-23} + f_{24}*ABP_{k-24}$.

Step 2: The coefficients of a weight function between displacement and ABP curves are used as movement characteristics. The computation is similar to the one described in Step 1 and performed at the same time. Again, any number of coefficients can be used; we will select 6 for this example.

Step 3: The relationships between the movement characteristics of Step 2 and the 25 coefficients of the weight function in Step 1 are described by an approximating linear function (i.e., matrix A and vector B), which is calculated through a sequence of 25 multiple regression analyses of the patients' data.

After Steps 1-3 are performed, the noninvasive ICP determination is made as follows: while the displacement (or the like) and ABP curves are recorded non-invasively for a new patient (one not used in the derivation of the above simulation function), the movement characteristics are computed every 10 seconds and transferred to the simulation function. Finally, the simulation function transforms the ABP curve into a simulated ICP curve.

Blood pressure measurements made using the passive or active acoustic modes are described in PCT International Publication WO 02/43564 and U.S. Patent Application Publication No. U.S. 2002/0095087 A1, which publications are incorporated herein by reference in their entireties. Noninvasive systems and methods of the present invention provide a measure of arterial or venous blood pressure using acoustic techniques to measure alternating compression and dilation of the cross-section or other geometric or material properties of an artery or vein, using empirically established relationships and/or mathematical models. In another aspect, blood pressure is determined using acoustic techniques to measure alternating compression and dilation of tissue surrounding blood vessels that is displaced as the vessels are compressed and dilated with the cardiac cycle. Geometrical properties that may be determined using acoustic detection techniques include changes in diameter, cross-sectional area, aspect ratio, rates of changes in diameter, velocity, and the like. Material properties that may be determined using acoustic detection techniques include the stiffness of vessel walls or tissue in proximity to vessel walls. Blood pressure may be assessed, for example, by acquiring acoustic data, in an active and/or passive mode, from target tissue sites at or in proximity to one or more blood vessels. The acoustic data can be related to the stiffness of vessel walls or supporting tissue, which can be related to blood pressure, just as acoustic data from a CNS target tissue site can be related to tissue stiffness, which can be related to ICP. Suitable target tissue sites for determination of arterial or venous blood pressure may comprise any blood vessel or surrounding tissue. Detection of ultrasound scatter data may be related, for example, with synchronous Doppler flow measurements within the same vessel.

A calibration step using a measure of blood pressure taken with a conventional blood pressure device, may be incorporated in the blood pressure determination. Acoustic proxies for the pulsatility of the blood vessel—such as oscillation rate of the blood vessel wall—may be substituted for direct measures of those quantities. In this method, the spontaneous changes in the diameter (or other geometric property) of the vessel being monitored are assessed using ultrasound, and this information is related (e.g., using correlation techniques) to synchronous Doppler flow measurements within the same vessel. Since the diameter (or other geometric property) of the vessel is a function of the pressure being exerted against the wall of the vessel by blood, and since the velocity of blood flow is dependent on the diameter (or radius) of the vessel through which the blood travels, blood pressure can be calculated from flow velocity measured by Doppler. By simultaneously measuring the pulsatility of the blood vessel of interest and the Doppler flow velocity proximal and distal to this site, continuous blood pressure can be determined.

Autoregulation

A patient's autoregulation status, or autoregulation capacity, may also be determined using acoustic data related to intrinsic and/or induced tissue displacements according to the present invention, as described in greater detail below. ICP and autoregulation status, or autoregulation capacity, are intimately related. The net volume of blood within the brain at any time point within the cardiac cycle is a function of systemic blood pressure and protective autoregulatory mechanisms of the brain vasculature, from its major arteries, having diameters on the order of millimeters, to its arterioles, having diameters on the order of microns. These various physical scales of cerebral vasculature respond with different time scales and different levels of contribution to the determination of ICP and autoregulation. The different classes of cerebral vasculature have different material properties, such as Young's modulus, which contribute to the different displacement properties in the brain.

The brain receives a substantially constant rate of blood flow, which is determined by cerebral perfusion pressure (CPP), where CPP=MAP−ICP over a wide range of mean arterial pressures. In this way, under normal conditions, the brain and its vasculature are capable of altering CPP in order to maintain proper blood flow to the brain. This is referred to as a normal state of autoregulation. When the ability to alter CPP to maintain proper blood flow to the brain is lost, autoregulation is abnormal and ICP becomes directly proportional to the mean arterial blood pressure.

In one embodiment, using continuously acquired noninvasive CNS target site acoustic data relating to intrinsic and/or induced tissue displacement or emission, along with simultaneous noninvasive or invasive measurements of continuous ABP and transcranial Doppler flow velocity, the status of cerebral autoregulation is assessed. CPP is determined from the displacement or emission data and ABP data. Specifically, correlation coefficient indices between time averaged mean flow velocity (FVm) and CPP (Mx), and between the flow velocity during systole and CPP (Sx), are calculated during several minute epochs and averaged for each investigation. These correlation indices are determined for a variety of clinical situations in which autoregulation and outcome is known. From this, regression lines are determined to infer the status of cerebral autoregulation for any set of Mx and Sx values. See, Czosnyka et al, Monitoring of Cerebral Autoregulation in Head-Injured Patients, Stroke Vol. 27, No. 10, October, 1996)

In another embodiment, continuously acquired noninvasive acoustic data relating to tissue displacement(s) and/or emission(s) is used along with simultaneous measurements of continuous ABP, to determine the status of cerebral autoregulation. Specifically, a pressure reactivity index (PRx) is calculated as a moving correlation coefficient between a finite number of consecutive samples of values for displacement and/or emission and ABP averaged over several minutes. Thus, a continuous index of cerebrovascular reactivity (autoregulation) to changes in ABP is determined. A positive PRx is indicative of impaired autoregulation and predicts unfavorable outcome, while a negative PRx indicates intact autoregulation and likely good outcome. See, Czosnyka et al., Continuous Monitoring of Cerebrovascular Pressure-Reactivity in Head Injury, *Acta* Neurochir [Suppl] 71:74-77, 1998).

In another embodiment, spectral analysis of simultaneously acquired continuous, noninvasive acoustic data relating to tissue displacement(s) and/or emission(s) and continuous invasive or noninvasive ABP data is used to determine the status of cerebrovascular autoregulation. Transfer functions (TFn) are calculated from fast Fourier transform (FFT) spectra as ratios of displacement and/or emission and ABP harmonic peak amplitudes to distinguish states of vasoreactivity. TF are calculated for a variety of known clinical conditions, and this data is used to determine values for the TF that correspond to specific states of autoregulation. These TF values can differentiate impaired autoregulation from effects solely related to elevated ICP or active vasodilation. See, Nichols, J et al., Detection of Impaired Cerebral Autoregulation Using Spectral Analysis of Intracranial Pressure Waves, J. Neurotrauma vol. 13, No. 8, 1996.

To accurately determine ICP and/or the state of autoregulation, the hemodynamic and/or cerebrospinal systems may need to be perturbed for a finite period of time to cause a known alteration in ICP, or to challenge autoregulation. Several exemplary types of perturbations, involving physiological challenges, are described below:

1) Mechanical perturbations of the hemodynamic system for evaluation of autoregulation may involve the placement of large pneumatic or hydraulic blood pressure cuffs around the lower extremities and inflated in order to increase venous return to the heart, thereby increasing vascular blood volume, leading to increased blood flow to the brain. The state of autoregulation can be assessed by analysis of the Doppler information. Other means of increasing blood flow to the brain including placing the patient in a gravity suit, changing ventilatory parameters on mechanical ventilators for intubated patients, and restricting arterial blood flow to the periphery.

2) Pharmacological perturbations of hemodynamic system for evaluation of autoregulation. If autoregulation is intact, the brain can respond to this decreased blood flow by re-directing blood flow and altering resistance to ensure that it receives adequate perfusion. Alternatively, intravenous fluid boluses can be administered to transiently increase blood volume and flow to the brain. If autoregulation is intact, the brain can respond accordingly. Other means for altering the blood volume and flow include the use of vasopressors, vasodilators, chronotropic and contractility agents.

3) Changes in patient position that alter ICP (e.g., Trendelenberg vs. reverse-Trendelenberg position) and changes in patient equilibrium, such as coughing, sneezing, etc., that alter ICP.

4) Modulation of mechanical ventilator input and output that alters intrathoracic pressure.

Under most circumstances, patients with intact autoregulation and normal ICP can tolerate any change in head body position, including head down or head up positions. Even in the fully normal, healthy individual, there is a transient change in ICP that is associated with such alterations in body position; within a few seconds, however, the body compensates and ICP returns to normal. It is conceivable that a change in body position, for example, will be required to cause a known change in ICP or autoregulation in order to calibrate or re-set the method used to non-invasively determine ICP and autoregulation.

Acoustic Source/detector Assemblies, Scanning and Localization Methodologies

One aspect of the present invention relates to acoustic source/detector assemblies for use in methods and systems of the present invention. In operation, an acoustic source/detector combination, such as a TCD source/detector, is stably mounted, or held, in proximity to a patient's body surface, such that the focus of the acoustic source(s) is adjustable to provide an acoustic focal point on a blood vessel or other target site within the patient's body. For CNS target sites, the acoustic source/detector is stably mounted, or held, in proximity to a cranial window, such that the focus of the acoustic source(s) is adjustable to provide an acoustic focal point on CNS tissue, such as on a cranial blood vessel. The acoustic source/detector combination is preferably provided as a unitary component, but separate acoustic source and detector components may also be used. The acoustic source/detector combination may be provided in connection with a mounting structure or accessory that provides temporary adherence to desired patient sampling locations and may be provided as a single use component.

Various types of acoustic transducers and acoustic transducer arrays may be used as acoustic source/detector assemblies and acoustic data acquisition components of the present invention. A single acoustic transducer, or a singer acoustic transducer array may be operated both as a source and a detector, or separate source and detector transducers or transducer arrays may be provided. Conventional PZT acoustic transducers may be implemented as acoustic data acquisition components in methods and systems of the present invention. Acoustic transducer arrays composed of cMUT and PVDF cells or elements may also be used and are preferred for many implementations. PZT, cMUT and PVDF acoustic transducers and arrays may be combined in various data acquisition components and operated in acoustic source and/or receiver modes in yet other embodiments.

In one embodiment, the acoustic source/detector combination may be mounted on a stabilizer, or on or in a structure, such as a helmet-type structure or headband that may be mounted on the head. An applicator containing an acoustically transmissive material, such as an acoustic gel, may be placed between the surface of the acoustic source/detector combination and the head. Steering of the acoustic device may be accomplished manually or using automated mechanisms, such as mechanical or electronic steering mechanisms. Such mechanisms are well known in the art.

One drawback of using acoustic techniques for measuring physiological parameters using a standard TCD transducer is that localization of a desired CNS target area using an acoustic transducer is challenging and often requires a trained, experienced sonographer to find and (acoustically) illuminate the desired target area, such as the MCA. After locating the desired target area, the sonographer generally attaches a cumbersome and uncomfortable headset to the transducer that stabilizes the transducer position and reduces the effects of patient movement and other disturbances on the position of the transducer. The sonographer may also be required to monitor acoustic readings and reposition the transducer intermittently to maintain the focus on the desired data acquisition area.

Figure 5:
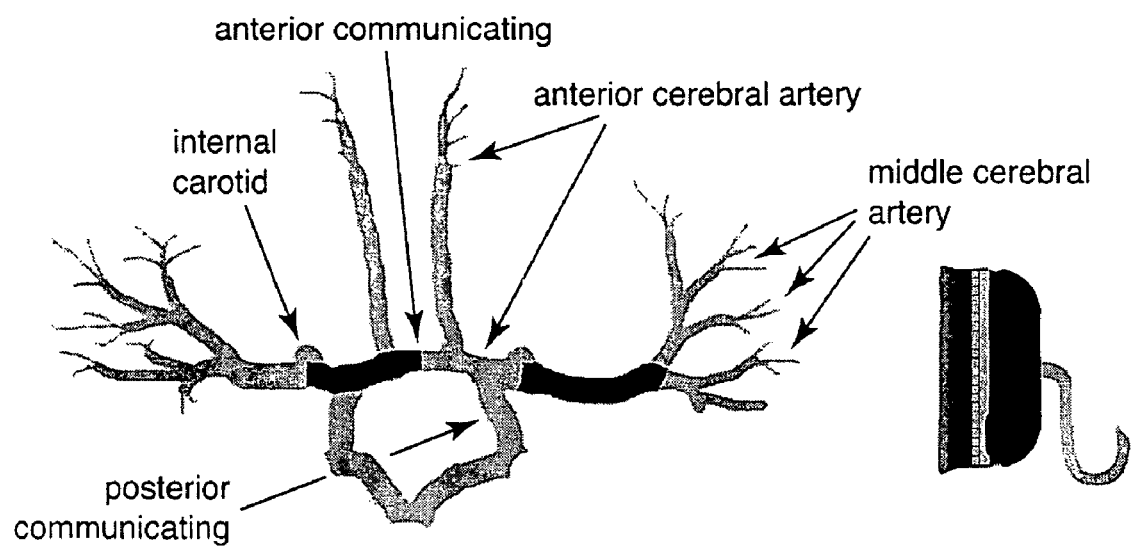
FIG. 5 illustrates the major cerebral vessels, including the middle cerebral artery (MCA), the target of standard transcranial Doppler procedures, and schematically illustrates an acoustic source emitting acoustic interrogation signals in a scanning mode.

It is desirable, in clinical settings, to provide systems and methods for locating and acoustically illuminating and/or probing a desired target area in a reliable and automated fashion, without requiring a trained sonographer. FIG. 5 illustrates the major cerebral vessels, including the middle cerebral artery (MCA) 10, the target of standard transcranial Doppler procedures and a target for acoustic measurements used in the methodology employed for determining ICP described above. The anterior cerebral arteries 14, anterior connecting artery 16, internal carotid artery 18 and posterior connecting artery 19 are shown. The darkened blood vessel branches denote blood flow towards acoustic device 12, while cross-hatched blood vessel sections denote flow away from the transducer. An acoustic source detector assembly 12 of the present invention is illustrated to the right of the cerebral vessels, emitting acoustic interrogation signals in a scanning mode as described below, in which a large target area is acoustically illuminated prior to the localization of a smaller target site.

Thus, another aspect of the present invention relates to methods and systems for locating and acoustically illuminating and/or probing a desired target site in an automated fashion using an array comprising a plurality of acoustic source and/or detector elements. An acoustic transducer/receiver array may be employed in a scanning mode, for example, to acquire acoustic data from numerous sites within a larger target area. Based on the acoustic data collected in the scanning mode, localized sites within the target area may be selected as target sites for focused acoustic illumination and/or probing. Localized target sites may be selected, or predetermined, based on any aspect of the acoustic data collected in the scanning mode, such as acoustic scatter amplitude, phase and/or frequency maxima or minima, tissue stiffness properties, endogenous and/or induced tissue displacement properties, rates of change of such properties, and the like. Focusing of elements of the acoustic transducer/receiver array on selected target sites may be accomplished in an automated fashion using mechanical or electronic beam steering and other automated acoustic focusing methodologies. In another embodiment, an automated system is provided that locates a desired target site within a larger target area in a scanning mode, focuses on the desired target site for acquisition of acoustic data, and thereafter periodically scans the target area and repositions the acoustic focus, if necessary, to maintain the focus of the acoustic source at the desired target site. Multiple target sites may also be located in a scanning mode and focused on sequentially and/or simultaneously for acoustic data acquisition from multiple target sites using acoustic transducer/receiver array assemblies of the present invention. Systems incorporating suitable arrays of acoustic source and/or detector elements are disclosed.

Figure 6A:
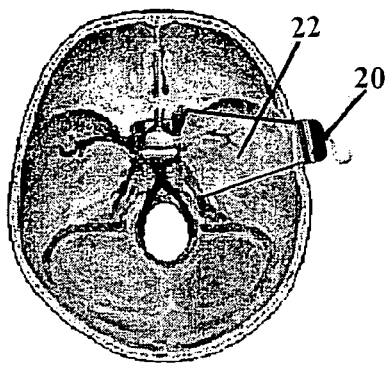
FIGS. 6A and 6B show, schematically, the use of a transducer array of the present invention in a scanning mode (FIG. 6A) used to locate the target area of interest based on its acoustic properties, and in a focusing and data acquisition mode (FIG. 6B).
Figure 6B:
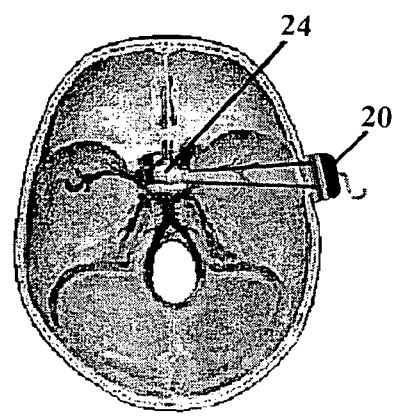

FIG. 6A illustrates, schematically, the use of a scanning acoustic transducer assembly 20 of the present invention that acoustically illuminates and acquires acoustic data from multiple points within a broad target area 22, such as a large portion of the cerebral blood vessel complex, in a scanning mode. Based on the acoustic data acquired in the scanning mode, localized target sites 24 within the scanned area may be identified and elements of the transducer assembly are focused on localized target site(s) for acquisition of acoustic data from the desired target site(s), as shown in FIG. 6B. Selection of localized target site(s) may be predetermined based on various acoustic properties, including the amplitude (or any amplitude derivative) of acoustic scatter data, Doppler analysis of acoustic scatter data, phase or frequency of acoustic data, changes in the primary and/or other maxima and/or minima amplitude, phase or frequency of acoustic signals within a cardiac and/or respiratory cycle or other period, or determinations derived from acoustic data, such as flow velocity, tissue stiffness properties, endogenous and/or induced tissue displacement properties, acoustic emissions associated with such displacements, rates of change of such properties, and the like. For determination of ICP using methods of the present invention, the selection of a desired localized target site, such as the MCA or another cranial blood vessel, is preferably accomplished by scanning the desired target area, as shown in FIG. 6A, and determining the localized site of highest amplitude acoustic scatter, or highest Doppler or flow velocity values, which represents the MCA. Acoustic elements of the acoustic source/receiver data acquisition component may then be focused on one or more localized MCA sites for acoustic data acquisition.

Various noninvasive, non-acoustic detection modalities may be employed alternatively or additionally to locate internal physiological structures, including blood vessels such as the MCA, prior to acquisition of acoustic data. Near infra-red spectroscopy (NIRS), magnetic resonance, and other techniques are known and used, for example, to image and locate internal physiological structures. Such techniques may be used in association with the methods and systems of the present invention for locating internal physiological structures prior to assessment of acoustic properties.

Using methodologies and assemblies described below, an acoustic source/detector combination, preferably an acoustic transducer array comprising multiple transducer elements, is operable in both a scanning mode and a focusing mode. One or more acoustic source element(s) of the acoustic data acquisition component scan(s) target areas of the interior of the cranium (or another target area) in a scanning mode to identify target sites having predetermined or desired acoustic properties. When the acoustic source has identified one or more target sites having the predetermined or desired acoustic properties, one or more of the acoustic source(s) may be manually or automatically focused on the desired target site(s) for operation in an acoustic interrogation or data acquisition mode. The acoustic source may also be programmed to monitor acquired acoustic data and to adjust the positioning and/or focus of the source to maintain the focus of selected or predetermined acoustic source(s) on the desired target site. Similarly, the acoustic source(s) may be programmed to collect data from a plurality of predetermined or programmed target sites at predetermined time points. Acoustic transducer source and detector elements of the present invention may, in fact, be programmed to collect one or more types of acoustic data from a single or multiple target sites, at one or more times. Acquisition of acoustic data, using methods and systems of the present invention, is preferably accomplished in an automated fashion.

Methodologies for scanning and locating desired target areas based on their acoustic properties may be based on "range-Doppler" search methodologies that were developed, for example, for programming torpedoes to hunt targets such as submarines. Range-Doppler processing is an efficient implementation of matched filtering that has been used in the radar and sonar signal processing community for many years. It is a robust technique, in part because it makes very few assumptions about the statistical nature of the environment and targets that it encounters. Range-Doppler processing provides a useful decomposition of the spatial and temporal (i.e. Doppler) scattering properties of the target of interest. Sensor time series data are divided into frames, often overlapped, multiplied by the transmitted waveform replica and then transformed into the frequency domain via the Fast Fourier Transform (FFT) algorithm. These operations implement, very efficiently, a bank of matched filters, each matched to a narrow range of Doppler shifts. Range-Doppler processing affords separation of targets in terms of their range and speed relative to the acoustic device. Intracranially, MCA flow is by far the largest target, which makes it a natural for this 'search and home in' approach.

Other methodologies for finding and maintaining an acoustic focus on a desired target area are also applicable. Acoustic holography techniques such as those described in Porter, R. P., P. D. Mourad, and A. Al-Kurd (1992), Wavefront reconstruction in variable, multimode waveguides. *J. Opt. Soc. Am.*, A9(11) 1984-1990 and Mourad, P. D., D. Rouseff, R. P. Porter, and A. Al-Kurd (1992), Source localization using a reference wave to correct for oceanic variability, *J. Acoust. Soc. Am.*, 92(1) 1031-1039, may also be used. Using acoustic holography techniques, signals from a target are combined in a convolution with signals from a reference source after each is measured on an acoustic array. The net result is a formula whose maximum occurs at the target site. To determine ICP using acoustic holography techniques, for example, all of the acoustic fields may be replaced by the Fourier transform of the acoustic field, or a component of the Fourier transform of the acoustic field, e.g. the Doppler signal. In this embodiment, the Fourier transform of the acoustic backscatter from an acoustic array serves as the target signal, and the forward scatter from a TCD or array placed on the opposite temple may be used as the reference source. These signals would be mathematically combined to find and maintain an acoustic focus on a desired target area.

In another embodiment, it would be useful to have the option for the user to have the opportunity to assist the automated targeting, user independent aspects of the present invention. This may be useful, for example, for cases where systems for automatically identifying the feature of interest may not be uniquely converging on that feature, or so that the user can validate whether or not the feature chosen by the computer is, in their opinion, the optimal feature. The key idea is that the feature of interest will be known to represent a local if not global minimum or maximum among a spatial distribution of values of the feature of interest. We will use the example of finding the maximum flow velocity in the middle cerebral artery, where the velocity in the middle cerebral artery is known to have a range of values spatially distributed along the middle cerebral artery, with the understanding that this technology is not limited to this application.

An exemplary acoustic system providing an automated targeting feature while allowing user participation in targeting may utilize conventional TCD systems made by DWL, Spencer Technologies, Nicolet, etc., where the acoustic sensor consists of a single transducer element, and where the acoustic system provides information only along the beam of the single transducer for a given orientation of that transducer. Here, the user manually manipulates the transducer so that it insonifies different portions of the cerebral architecture, and electronically steers the depth along the transducer beam axis. The user would be guided by the real-time display of information, along with the user's memory of what the display has shown in the preceding moments, to seek out the maximum in flow velocity in the MCA. One portion of the display may provide the real time value of the variable of interest at a position relative to the face of the transducer (reported in absolute units, or arbitrary units, since the actual depth is not important) that is chosen by the user with a cursor designated for this purpose. The display may provide, for example, the real time value of flow velocity in the MCA, otherwise known as the spectrogram of the flow.

Another portion of the display may provide a graphical image designed to communicate to the user, at any given orientation of the transducer, the direction of larger values of flow in the MCA relative to the real time position of the cursor. This may take the form of two arrows pointing in different directions, e.g. one pointing 'up' one pointing 'down,' where up and down are known to the user to represent deeper relative to the present position of the cursor, and more shallow relative to the present position of the cursor, respectively. If there are local maxima in flow velocity in both directions, the direction in which a greater maximum exists would be designated by having a brighter arrow pointing in that direction. These flow velocity gradients may be calculated within the associated controller component by measuring the Doppler shift along all of the points insonified at a given moment by the transducer to provide a real-time calculation of the local gradient of the flow velocity. This calculation may be performed using a variety of well-known mathematical formulae (one-sided differences, centered differences to a variety of orders, etc). The absolute position of the local flow velocity maximum in flow in the MCA need not be known or reported or displayed to the user.

What the user gains from this analysis is a direction, relative to the current position of the cursor, which position need not be defined, of the local maximum in flow velocity. The user may then manipulate the cursor to report the spectrogram at a deeper or a shallower position along the acoustic beam and judge for themselves whether they have achieved a local maximum in flow velocity. By providing guided exploration of the flow velocity along the beam axis in this fashion, in combination with physical manipulation of the relative position or angle of the transducer, the user will be able to locate the flow velocity maximum in a guided fashion.

Standard TCD devices also allow for the device to emit sound whose amplitude is tied to the flow velocity at a given point along the beam of the transducer, the one, in particular, whose spectrogram is shown to the user. Such supplemental information would be of interest to the user of the present invention. In addition, one could designate the intensity of the display to increase or decrease as the absolute value of the flow velocity increased or decreased as the cursor was manipulated along the beam of the transducer. In this way visual information would supplement the aural information already available to the user.

Using an acoustic array comprising a relatively dense distribution of acoustic transducers rather than a single transducer or a sparse array, one may have, at any given moment, information relating to the relative spatial distribution of flow velocity in depth at a variety of angles from the center of the acoustic beam. A user assist feature may provide a display showing the direction of the local flow velocity maximum. Using a transducer array, however, locational information relating to the direction of maximum flow velocity may be provided in additional dimensions, and the user may be guided by an arrow pointing in each of the three possible directions of cursor movement relative to the real time cursor position. One set of arrows may indicate the local maximum is deeper than, or shallower than, the present cursor position. Another set of arrows may indicate that the local maximum is more anterior or posterior to the present cursor position. Yet another set of arrows may indicate that the local maximum in flow velocity is more superior or inferior to the present cursor position. This information may be calculated as described above, using Doppler analysis of acoustic backscatter from the field of positions insonified by the transducer array. The user's positioning of the array may be guided by this information, along with supplemental aural and visual information as described above, including the instantaneous spectrogram at the position of interest, to move the cursor, and re-examine the spectrogram.

Acoustic systems and transducer assemblies for locating and illuminating one or more desired target site(s) are described below with reference to the middle cerebral artery (MCA) as the desired target site. It will be understood that this target site is exemplary only and that methods and acoustic assemblies of the present invention may be used for locating and acoustically illuminating other target sites as well, including cranial blood vessels and both CNS and non-CNS target sites. The acoustic methods and systems described below may be useful for any application in which collecting data relating to an acoustic property of a desired target site is required.

It will be appreciated that acoustic transducer arrays having various configurations and structures are known in the art and may be useful for various applications. Acoustic transducer arrays of the present invention are generally thin and generally comprise a single layer or thickness of transducer elements. Stacked, multiple layer transducer cells, or elements, may be used for some applications. The transducer elements or cells may be arranged on a single plane to form a generally flat, planar array, or they may be arranged to form a curved or a geometrically stepped array. Transducer arrays having various configurations and structures may be useful for applications contemplated in this disclosure.

In one embodiment, data acquisition components comprising acoustic source/detector combinations of the present invention comprise a plurality of capacitive micromachined ultrasound transducer (cMUT) cells. cMUT ultrasound transducers are manufactured using semiconductor processing techniques and have sufficient power and sensitivity to transmit and receive at diagnostic ultrasound energy levels, which is necessary and sufficient for purposes of the present invention. The transducer elements are fabricated using small capacitive diaphragm structures mounted on a silicon substrate. cMUT transducer arrays have the potential of being produced very inexpensively, and may also have the support electronics integrated onto the same chip.

Figure 7:
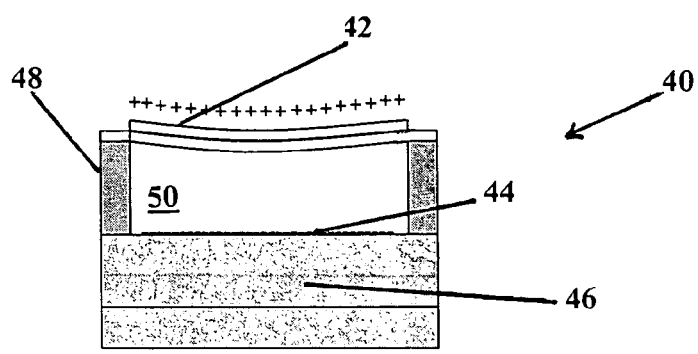
FIG. 7 shows a schematic illustration of a single cMUT transducer cell structure.

FIG. 7 shows a schematic illustration of a single cMUT ultrasound transducer cell structure. As shown in FIG. 7, cMUT ultrasound transducer cell 40 comprises a positive electrode 42 illustrated as the top electrode and a negative electrode 44 illustrated as the bottom electrode. The top electrode is generally provided on or in connection with a flexible membrane and the bottom electrode is generally provided on or in connection with a substrate 46, such as a silicon substrate. Insulating supports 48 are provided to form a sealed chamber 50 between the positive and negative electrodes. Chamber 50 may contain a gas or liquid or gel-like substance, or it may be provided as an evacuated chamber. The diaphragm structures of the cMUT ultrasound transducer convert acoustic vibrations into a modulated capacitance signal, or vice versa. A DC bias voltage is applied and an AC signal is either imposed on the DC signal in transmission or measured in reception. In general, cMUT transducer elements may be operated in various modes of transmit and receive operation, including unbiased mode, non-collapsed mode, collapsed mode and collapsed snapback mode (transmit only). One advantage of using cMUT transducer cells, elements and arrays is that the electronics may be provided on or in the cell structure, greatly simplifying the electronic communication to and from the array and facilitating programmable array features.

Figure 8:
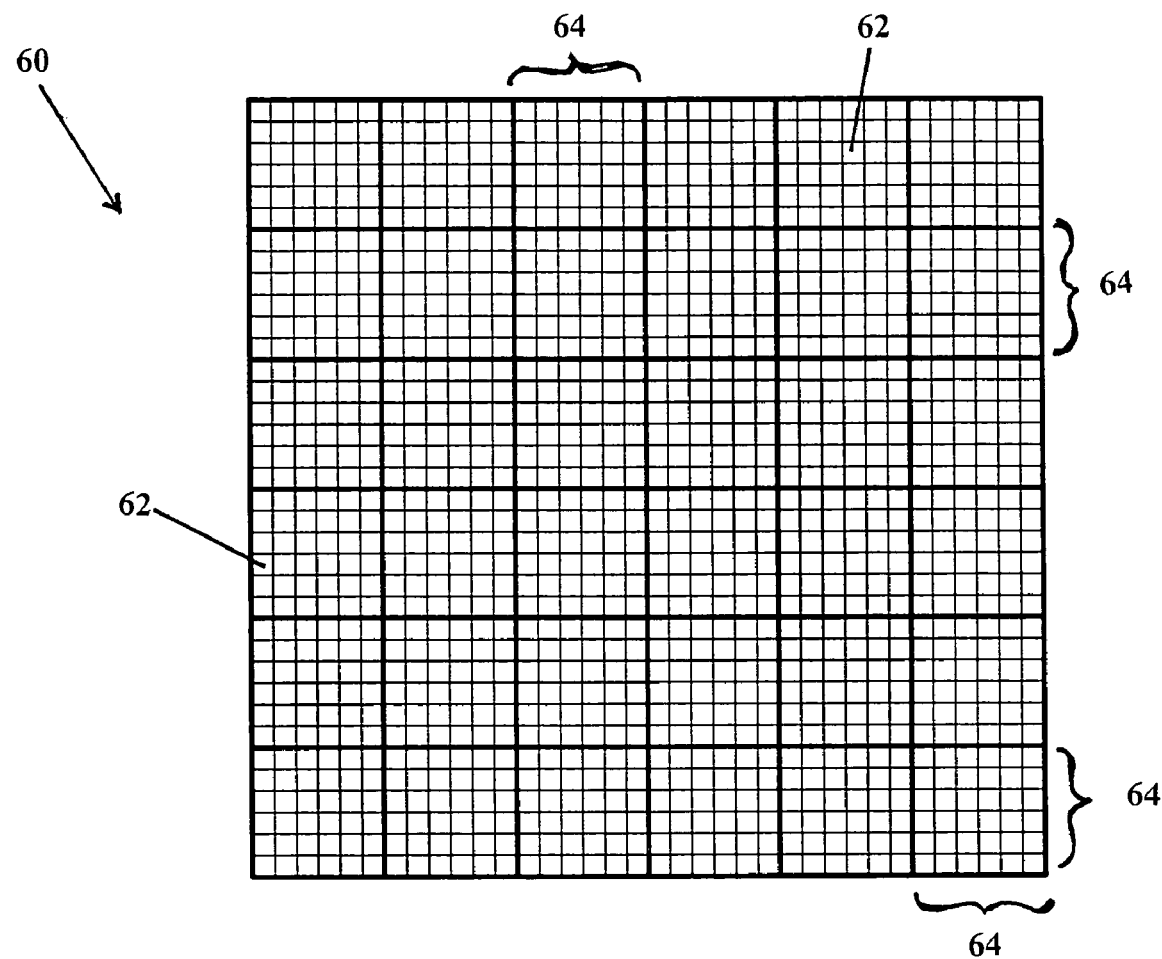
FIG. 8 shows a schematic illustration of a cMUT transducer array comprising a plurality of cMUT transducer cell structures.

A cMUT transducer array is composed of multiple individual cMUT ultrasound transducer cell structures arrayed as elements, with the elements arrayed in rows and/or columns and/or smaller divisions forming the array. FIG. 8 schematically illustrates such an array 60. The number of cMUT transducer cells 62 forming each of the transducer elements 64, and the number of elements forming the array may be varied, depending on the array application. The cMUT transducer array 60 illustrated in FIG. 8 comprises a plurality of cMUT transducer elements 64, each of the transducer elements 64 comprising a 6×6 arrangement of individual cMUT cells 62. The array 60 thus comprises a 6×6 arrangement of 36 transducer elements 62, each of the transducer elements 62 being composed of 36 individual cMUT transducer cells. cMUT transducer arrays having various configurations may be assembled and used in the present invention.

The inventors have made the unexpected discovery that cMUT transducer arrays can be configured and operated to achieve acoustic transmission and sensitivity levels sufficient to perform as acoustic transmit/receive devices suitable for use in medical devices, such as TCD devices. More specifically, cMUT transducer arrays of the type illustrated in FIG. 8 having a plurality of cMUT element columns operated at an 80V bias, 28 Vac to transmit acoustic energy to CNS target sites at intensities of up to 1.75 W/cm$^2$, while typical transmission intensities of only about 0.6-0.7 W/cm$^2$ are required for determining cerebral blood flow using conventional TCD acoustic devices. cMUT transducer arrays operated experimentally at an 80 Vbias and at a gain of 60 and 80 dB to receive signals from CNS target sites in a range of less than 4 to greater than 6 cm from the array at a level sufficient to make Doppler determinations.

cMUT transducer cells and elements may be arranged in different combinations to provide cMUT transducer arrays having different capabilities. If each of the cMUT cells is provided with independently controlled or controllably electronics, each of the cMUT cells may act as a transducer element and an array may be provided as a plurality of independently controlled or independently controllable cMUT cells. More typically, a transducer element comprises a plurality of cMUT cells that is electronically controlled or controllable as a unit. Thus, in the array illustrated in FIG. 8, each of the elements 64 is composed of multiple (6×6) cMUT transducer cells 62 that are controlled or controllable as a unit. Alternatively, a plurality of the elements 64, such as elements forming a row or a column, may be electronically controlled or controllable as a unit to provide a cMUT transducer array comprising a plurality of row or column transducer elements. A one-dimensional (1D) array may be composed of a single transducer element comprising multiple cells, while a two-dimensional (2D) array is composed of multiple transducer elements arranged in a generally planar, two-dimensional configuration.

In one embodiment, two cMUT acoustic arrays, each composed of a single or multiple transducer elements, are aligned in a "Mills Cross" configuration in which two transducer arrays are arranged generally orthogonal to one another, which allows one array to sweep vertically in send and receive modes and the other to sweep horizontally in receive and send modes. In this implementation, a first linear cMUT transmit array may be steerable in a first direction, such as a vertical direction and a second linear cMUT receive array is arranged generally orthogonal to the first linear array and may be steerable in a direction orthogonal to the first direction. The two, crossed linear cMUT arrays alternatively transmit and receive ultrasound beams while steering the sending and listening beams, to identify and focus on acoustic signals having the desired property.

In another embodiment, an acoustic array comprising PVDF (polyvinylidene fluoride) film transducers is used as an acoustic detector array, alone or in combination with a cMUT array or a single element PZT transducer employed as the source. In an exemplary embodiment comprising a PVDF array in combination with another transducer or array, the source transducer or array transmits sound through the PVDF array, sweeping the sound in a single dimension generally perpendicular to the arrangement of the PVDF array. The PVDF array serves as the acoustic detector, receiving and processing acoustic signals.

Figure 9:
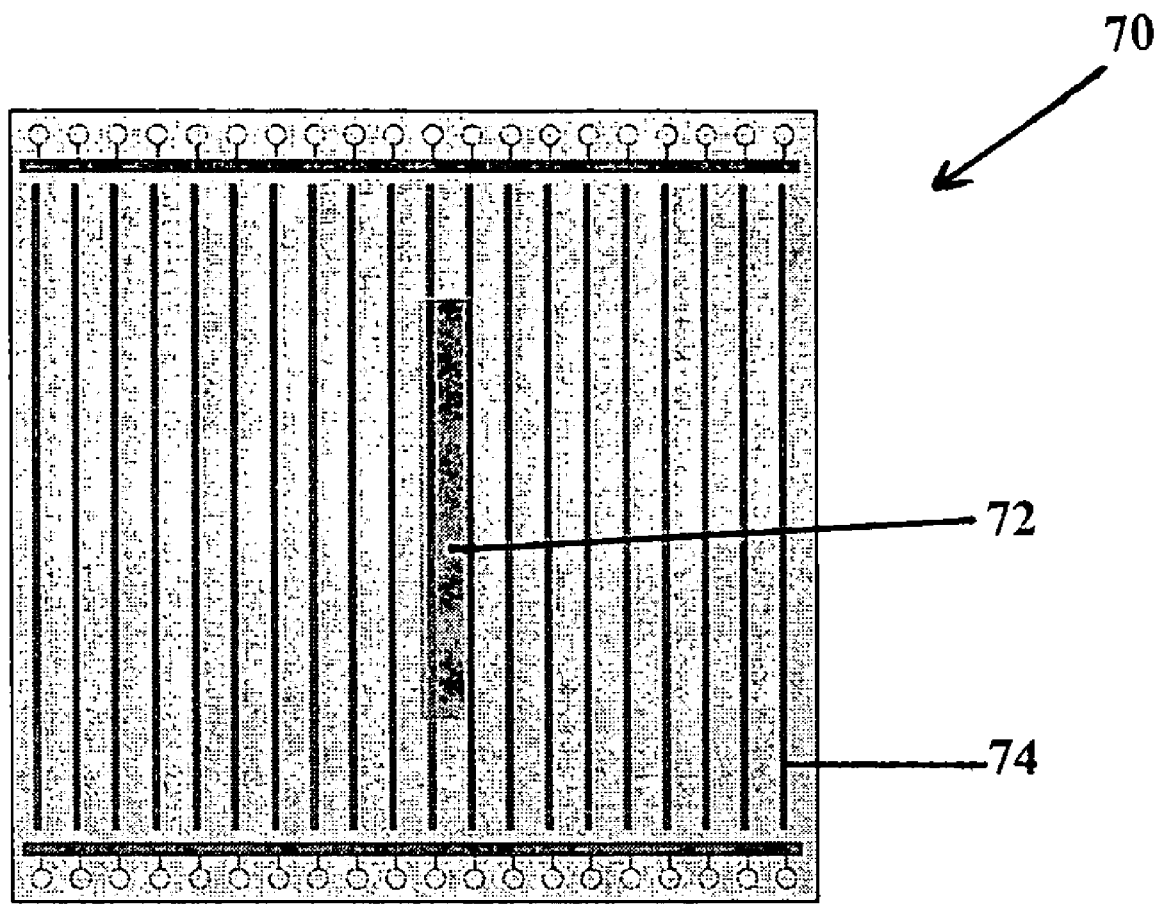
FIG. 9 shows a schematic diagram of an acoustic source/detector combination comprising a combination PVDF/cMUT tranducer structure.

FIG. 9 presents a schematic diagram illustrating an acoustic transducer array 70 of the present invention comprising combination PVDF/cMUT arrays. The combined depth of the arrays is generally quite small and may be on the order of about 1 cm. The cMUT array 72 is arranged below the PVDF array 74, with the PVDF array 74 arranged closest to the subject's surface during use. In this configuration, the cMUT array operates as the acoustic source and transmits acoustic beams through the PVDF array. cMUT array 72 may be composed of a 1D (as shown) or 2D array comprising one or more cMUT acoustic elements. The PVDF array may also be provided as a 1D array (as shown) or as a 2D array. When acoustic source(s) and/or detector(s) are provided as 2D arrays, they are capable of sending and/or detecting acoustic signals in two dimensions, rather than a single direction.

Figure 10A:
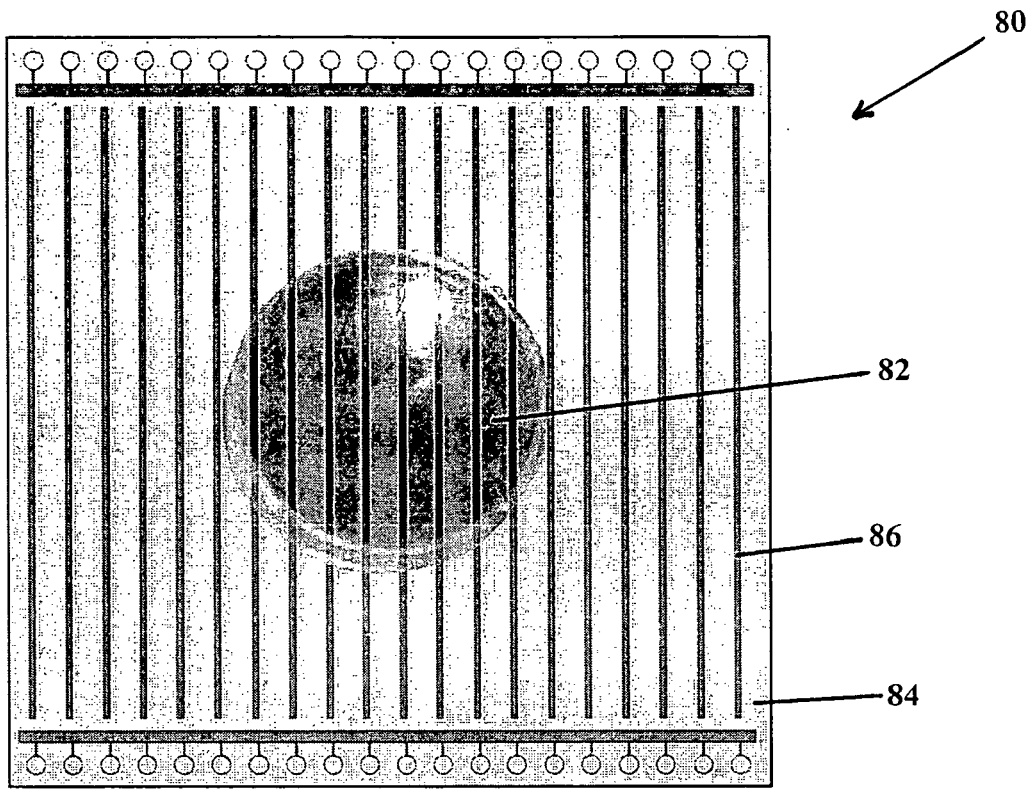
FIGS. 10A and 10B show schematic diagrams of an acoustic source/detector combination comprising combination PVDF array/PZT transducer structure.
Figure 10B:
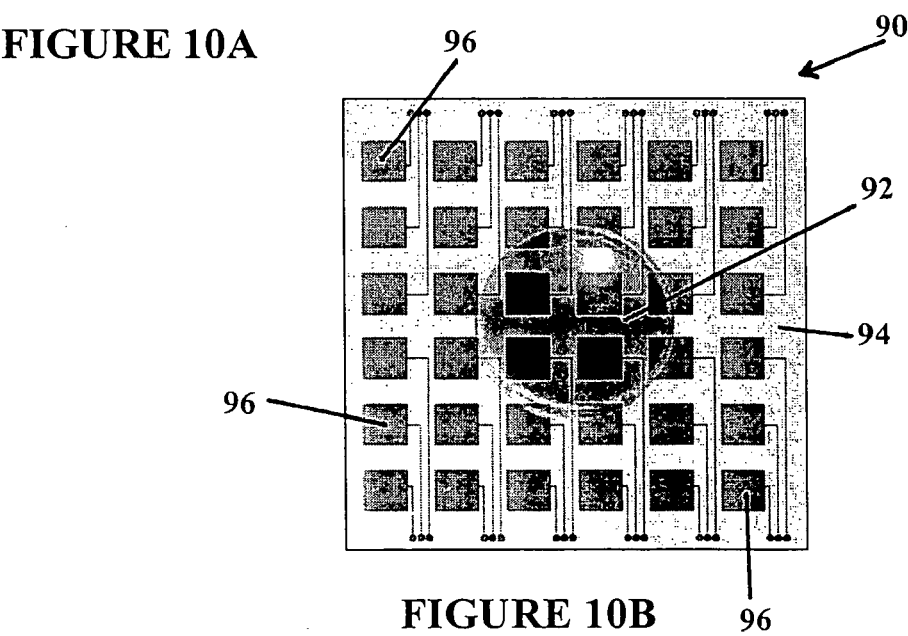

FIGS. 10A and 10B show a schematic diagram illustrating an acoustic array of the present invention comprising combination PVDF array/PZT transducer. A cMUT array may similarly be used in combination with a PZT transducer. The PVT transducer is generally mounted below the PVDF or cMUT array and transmits as an acoustic source through the PVDF or cMUT array in a single, broad beam. In these embodiments, the PZT transducer generally serves as the acoustic source and the PVDF or cMUT array generally serves as the acoustic detector.

FIG. 10A shows an acoustic source/detector combination 80 comprising a PZT transducer 82 underlying a PVDF or cMUT transducer array 84 having a plurality of aligned transducer elements 86. Each of the aligned transducer elements 86 is controlled or controllable as a unit. FIG. 10B illustrates another acoustic source/detector combination 90 comprising a PZT transducer 92 underlying a PVDF or cMUT transducer array 94. transducer array 94 comprises a plurality of transducer elements 96 controlled or controllable as a unit spaced in a two-dimensional configuration. Thus, the PVDF or cMUT array may be constructed as a 1D array comprising a plurality of aligned transducer elements, as shown in FIG. 10A, or as a 2D array comprising a plurality of transducer elements arranged in a two dimensional configuration, as shown in FIG. 10B.

One of the advantages of the ultrasound transducer array systems of the present invention is that multifunctional arrays may be provided in a relatively high power, yet inexpensive system. Such arrays are very versatile, are capable of performing multiple acoustic functions and may be pre-programmed or programmable to provide desired functions, and may be provided as disposable or single-use elements of an integrated clinical diagnostic system. In one embodiment, acoustic arrays of the present invention are provided as a single-use acoustic data acquisition component of a medical device, such as an ICP monitoring device, comprising one or more acoustic transducer arrays in operative communication with a controller component having data processing, storage and/or display capability. The one or more acoustic transducer arrays may communicate with the controller component by means of one or more detachable cables, or using a radio frequency, infrared or other wireless technology. The transducer array(s) may be steerable and may be programmed to scan one or more target areas having certain boundaries or parameters, and locate one or more desired target site(s) based on preselected or selectable acoustic properties. The transducer array(s) may furthermore be programmed and/or controllable to establish and maintain a focus by directing ultrasound beams having a preselected intensity, amplitude, phase, frequency, etc., to the target site(s) in an automated fashion. Transducer arrays of the present invention may also be programmed to collect acoustic data from multiple target sites simultaneously, or at different times. In one embodiment, a transducer array, or a plurality of arrays, may be programmed to operate alternatively as acoustic sources and detectors. In one embodiment, multiple transducer arrays used for monitoring multiple patients provide data to and communicate with a single data processing, storage and display device.

Figure 11A:
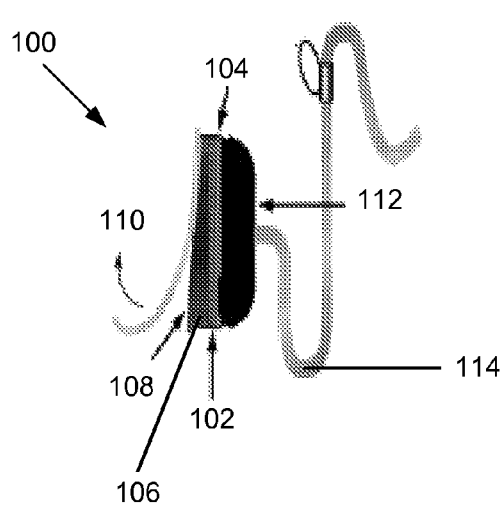
FIGS. 11A and 11B illustrate an exemplary patient interface unit having an acoustic source/detector combination of the present invention.
Figure 11B:
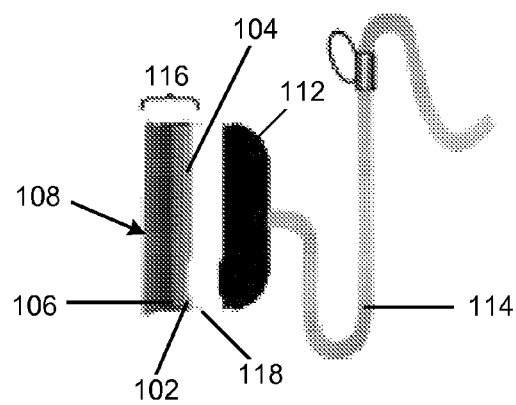

FIGS. 11A and 11B illustrate one exemplary embodiment of acoustic data acquisition components comprising acoustic source/detector systems, such as acoustic arrays, of the present invention. In the embodiments illustrated in FIGS. 11A and 11B, both disposable and non-disposable elements are shown. In this system of FIG. 11B, costly elements of the acoustic system are provided as non-disposable components, while less costly components, which require close interaction with a patient and, perhaps, sterilization, are provided as a single-use component.

FIG. 11A illustrates an acoustic data acquisition component 100 comprising an acoustic transducer array 102 that interfaces with an array electronics component 104 and an acoustic transmission component 106 that facilitates high fidelity acoustic transmission between transducer array 102 and a subject's body surface. Acoustic transmission component 106 preferably comprises a sealed enclosure containing an acoustically transmissive material, such as an acoustic gel having uniform properties and being substantially free from acoustically significant discontinuities, such as bubbles. Acoustic transmission component 106 may incorporate an adhesive substance on a least a portion of an exposed surface 108 to facilitate temporary adherence of the data acquisition component to a subject's body surface. Exposed surface 108 bearing an adhesive substance may be protected by a detachable cover 110 that may be removed prior to placement on a subject's body surface.

The transducer array and array electronics component may be permanently mounted in or on a structure 112 that facilitates communication of data and/or power to and/or from a controller component. Structure 112 may incorporate control and/or power features or may provide operable connection of the transducer array and array electronics to control and/or power features that are housed in a separate controller component. Data acquisition component 100 may communicate with a controller component through a structure 112 and cable 114, as illustrated in FIG. 11A, or communication may be provided using alternative communications methodologies, such as RF communications systems. If transducer array 102 and array electronics component 104 are mounted permanently or semi-permanently in structure 12, acoustic transmission component 106 may be provided as a single use component and may be affixed to an exposed surface of transducer array 102 prior to mounting on a subject's body surface.

Alternatively, acoustic transducer array 102, array electronics component 104 and acoustic transmission component 106 may be provided as a single use acoustic data acquisition component 116, as illustrated schematically in FIG. 11B. Single use acoustic data acquisition component 116 has an electronics interface component, illustrated schematically as wire 118, that provides communication between array 102 and array electronics component 104 and electronics and/or power capabilities provided in structure 112 or in a remote controller component. The electronics interface component provided in connection with data acquisition component 116 may be a hard-wired interface component that relies on contact with a mating interface component in structure 112, or it may be provided as a wireless interface communications component. In this embodiment, single use data acquisition components 116 may be packaged in a sterile or non-sterile fashion.

In this embodiment, an acoustic array is provided as part of a single use or disposable system element, in combination with a patient interface component. The acoustic array is preferably in contact with acoustically transmissive material, such as an acoustic gel, that provides high fidelity acoustic transmission into and from the target area. The acoustically transmissive material is preferably interfaced with a contact material, such as an adhesive material, that facilitates temporary positioning and affixation of the disposable system element to a patient's skin. The patient contact material may be protected by a removable cover, which is removable at the time of use. The disposable system element, including the acoustic array, may be provided as a unitary element that may be sterilized and packaged for one-time use.

Alternative single use systems and elements may also be employed. In one such alternative system, acoustically transmissive material layers may be provided as a separately sterilized, packaged component that is designed to interface with a non-disposable component including the acoustic array(s). Such layers may be provided with an adhesive layer on one side for contact with the patient's skin. Or, a recess may be provided for manual application of acoustically transmissive material. It will be evident that many different embodiments and arrangements of disposable and non-disposable elements may be employed.

This compact, disposable array element may be placed in contact with the temple of the patient and, when activated, electronically scans a target area of interest, such as the area of cerebral blood vessels, and then focuses the acoustic source(s) and detector(s) on the target site of interest, such as the MCA. The acoustic array monitors and stays focused on the target area of interest during operation. In this embodiment, the acoustic array forms part of a disposable assembly including an acoustic gel, or another acoustic material that facilitates transmission of acoustic signals at the interface with the patient's skin during operation. The exposed surface of the acoustic gel is preferably interfaced with one or more adhesive elements that facilitate temporary placement on and consistent contact with a desired patient surface. A removable cover may be provided over the acoustic gel to preserve the acoustic array and other components.

These elements may be provided as a disposable unit, as shown in FIG. 11B, that is mountable on non-disposable elements of the system. Non-disposable elements of the system may include mounting hardware, one or more cables or wireless transmission interfaces, and a data processing, storage and display device (not shown).

Placement of the acoustic source(s) and detector(s) on a subject for assessment of acoustic properties of CNS tissue (including blood and blood vessels) may be at known "acoustic windows" in the cranium. The placement of the source(s) with respect to the detector(s) will depend on the acoustic data desired—e.g., for collection of back scatter acoustic data, the source(s) and detector(s) are in proximity to one another, while the source(s) and detector(s) are positioned generally opposite one another for collection of forward scatter acoustic data. Acoustic scatter or reflection data may be collected at various angles by placing the source(s) and detector(s) at various locations on the patient.

To implement methods and systems of the present invention for determining ICP, data relating to the height difference between the transcranial Doppler measurement and the peripheral blood-pressure measurement may be desirable. To that end, a hydrostatic sensor may be provided when the acoustic source/detector device comprises an acoustic, microwave or infra-red receiver, with a corresponding sender being provided on the peripheral blood-pressure monitor. With the known travel time of these transmission modalities, one can measure the linear distance between the headset and the peripheral blood-pressure monitor. A sensor that measures the direction towards the ground may also be placed on the acoustic source/detector device to create a coordinate system that allows the automatic measurement of the angle between the ground and the peripheral blood-pressure monitor. Feeding that information into a small integrated circuit appropriately programmed, one can take this direct distance, and the angle, and calculate the vertical height difference between the headset and the peripheral blood-pressure monitor. Other types of hydrostatic sensors may also be used.

Methods and systems of the present invention have been described with reference to ICP determinations using $V\_mca$ measurements, although acoustic properties from other cranial target sites may be used in determining ICP. Automated acoustic scanning and target location may be facilitated using displayed information.

In certain embodiments, the user may simply mount a transducer array on the patient, and an automated acoustic source/detector scanning feature operates to find desired targets, such as maximum $V\_mca$. Other sites having unique acoustic properties may also be located. Coordinates for target locations and values for acoustic properties may be stored, over time, and displayed in a variety of formats.

Methods and systems of the present invention may be used in a variety of settings, including emergency medicine settings such as ambulances, emergency rooms, intensive care units, and the like, surgical settings, in-patient and out-patient care settings, residences, airplanes, trains, ships, public places, and the like. The techniques used are non-invasive and do not irreversibly damage the target tissue. They may thus be used as frequently as required without producing undesired side effects. The methods and systems of the present invention do not require patient participation, and patients that are incapacitated may also take advantage of these systems. The methods and systems for assessing tissue properties, including ICP, may be used on a continuous or intermittent basis for monitoring tissue properties or ICP.

All of the publications described herein, including patent and non-patent publications, are hereby incorporated herein by reference in their entireties.

The following examples are offered by way of illustration and are not intended to limit the invention in any fashion.

EXAMPLE 1

ICP Prediction Results Based on Empirical Studies Using TCD $V\_mca$ and Invasively Determined Continuous ABP Measurements as Variables A prototype system for collecting data, deriving and applying a non-linear relationship between the variables of cranial blood vessel velocity and ABP was assembled using commercially available components. This prototype consisted of a notebook computer with a PCMCIA National Instruments (NI) 6024-E data acquisition (DAQ) card, a box containing the exposed backplane of the NI-DAQ card and a microphone input matching circuit, a specialized adapter designed to mate to the signal output port of a Spacelabs telemetry unit, and a Spencer Technologies TCD 100M Power M-Mode Digital Transcranial Doppler device and control pad with standard TCD ultrasound transducer and FDA-approved headband device for mechanical fixation to the head. The Spencer TCD 100M device was not modified in any way from its FDA-approved configuration. All electronic items were powered using an approved uninterruptible power supply (UPS). No portion of the data acquisition system, except portions of the FDA-approved Spencer TCD device, interacted with the patient in any way.

Using the flow velocity in the middle cerebral artery ($V\_mca$), determined by analysis of acoustic backscatter data taken using the Spencer Technologies device, and arterial blood pressure (ABP), measured invasively with an arterial line, as variables, a non-linear relationship between $V\_mca$, ABP and ICP was derived by training and validating an ANN as described above.

We acquired data from a set of patients for whom we were able to measure ICP invasively along with V_mca and ABP. For patients with a focal injury, ICP was invasively measured from the same hemisphere as the injury focus, and V_mca was measured from this side as well. This is an issue because the brain, being a compartmentalized solid, can support pressure gradients across its structure. For example, in baboons, inter-hemispheric ICP differences up to 10 mmHg have been measured, while in people, these differences have been measured up to 25 mmHg. We also need the height difference between the point of ICP and ABP measurements, to take into account the hydrostatic pressure difference between the point of ABP and the brain. For example, this would be zero in supine patients. Then we required another set of patents, independent of the first set, on which we tested our model. For these patients invasive ICP devices were placed and the V_mca measurements were taken in the appropriate hemisphere.

We successfully collected data from 15 patients, eight of whom matched our patient criteria. After data acquisition from these 15 patients, we analyzed the data from 11 of them, and initialized our algorithm in the following way. Because we had a small patient population, we serially determined the algorithm using seven of the eight patients, and tested it on the eighth. Doing this eight times tested our nICP methodology eight times, through the formation of eight slightly different algorithms. We also used these eight core patients to develop a single algorithm that we then tested against three other patients that did not quite fit our patient criteria, but for whom we had data sets, as described below.

Figures 12A, 12B:
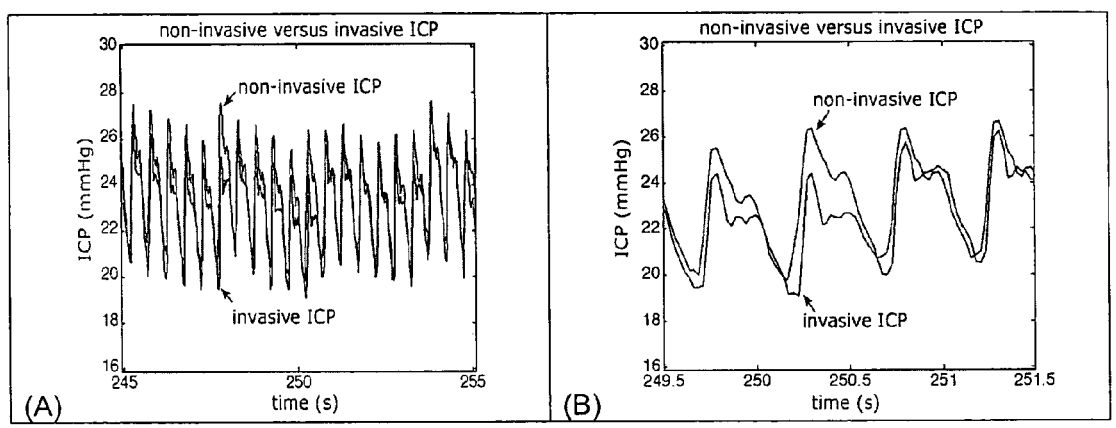
FIGS. 12A and 12B show comparisons of instantaneous traces of invasively measured (generally, lower trace) and non-invasively determined ICP (generally, upper trace) for an exemplary patient described in Example 1.

FIGS. 12A and 12B show a comparison of the instantaneous time traces of measured and predicted ICP from one of the core eight patients, reduced down from an initial data acquisition rate of 250 Hz to 20 Hz (i.e., there are twenty data points per second for each data set, or roughly twenty points per cardiac cycle). The invasively measured ICP is shown in the generally lower traces, while the non-invasively inferred ICP is shown in the generally upper traces. The data in FIG. 12A manifests both cardiac and respiratory forcing, while the enlarged trace of FIG. 12B highlights the signals on the time scale of the cardiac cycle. The predicted ICP traces are remarkably similar to the measured ones, with a tendency to under-predict the low values of ICP during diastole and over-predict the high values of ICP during systole. This is typical of seven out of our eight predictions, with an exception discussed below.

Point-by-point comparisons of time series for each patient demonstrates our successful prediction of invasively measured ICP, using only invasively measured ABP and acoustic measurement of the blood flow rate in the middle cerebral artery (V_mca), and a properly determined algorithm. Comparisons of invasively measured instantaneous ICP and predicted instantaneous ICP for eight patients are shown below, in Table 1. The Invasive ICP column shows the mean and standard deviation of the invasively measured ICP. The Predicted ICP column shows the mean and standard deviation of the predicted ICP. The Error column shows the mean and standard deviation of the error derived by subtracting the value of the measured and predicted ICP at each time point.

TABLE 1

| Patient | Invasive ICP | Predicted ICP | Error |
|---|---|---|---|
| 1 | 11.54 ± 1.55 | 11.20 ± 1.53 | 0.34 ± 1.79 |
| 2 | 12.31 ± 1.31 | 11.98 ± 1.05 | 0.34 ± 1.12 |
| 3 | 23.14 ± 2.27 | 22.98 ± 2.01 | 0.16 ± 1.71 |

TABLE 1-continued

| Patient | Invasive ICP | Predicted ICP | Error |
|---|---|---|---|
| 4 | 18.81 ± 1.06 | 18.20 ± 1.90 | 0.61 ± 1.68 |
| 5 | 22.28 ± 3.70 | 21.48 ± 6.43 | 0.80 ± 6.61 |
| 6 | 17.09 ± 2.43 | 15.24 ± 1.39 | 1.85 ± 1.95 |
| 7 | 7.29 ± 2.57 | 28.27 ± 6.15 | −20.98 ± 5.71 |
| 8 | 22.63 ± 3.04 | 22.75 ± 2.64 | −0.12 ± 2.86 |

The comparison of invasive and predicted ICP for Patient #4 shows that the average point-by-point difference between invasive and predicted ICP was 0.80 mmHg, with the likelihood that 95% of the predicted ICP values will be within 1.68 mmHg of the measured value. FIGS. 12A and 12B show representative data from this representative patient. For six of the eight patients (#1-5 and 8), the average value of the instantaneous difference between measured and predicted ICP is less than 1 mmHg—the average uncertainty in the invasive ICP measurements. For another patient (#6), the average value of the instantaneous difference between measured and predicted ICP is less than 2 mmHg. Moreover, for these seven patients, the vast majority of the instantaneous differences are less than 2 mmHg.

We formulated our prediction methodology using all eight core patients and applied it to three other patients who were not included in with the group of core patients. Because the site of brain injury was unknown in these patients, the acoustic measurements were taken from the hemisphere opposite from the site of invasive ICP measurements, or because the invasive ICP measurements were on the side opposite from the focal injury. For two of these patients, the predicted, instantaneous ICP was, on average, within 1 mmHg of the invasively measured, instantaneous ICP, as above. For the third patient, the predicted, instantaneous ICP was within an average of 4 mmHg of the invasively measured, instantaneous value, consistent with known inter-hemispheric differences in ICP in brain-injured patients. These are clinically acceptable uncertainties.

That the results for Patients #5 and #7 were not as successful as the others and provide important information. While the mean error for Patient #5 was 0.80 mmHg, the standard deviation of the error was quite large, 6.61 mmHg. This was because this particular patient was in cardiac arrhythmia, resulting in completely unpredictable cardiac cycles, which would occasionally throw the predicted ICP significantly far from the measured ICP. Regarding Patient #7, our methodology failed completely. We believe that Patient #7, whose mean ICP was 5 mmHg below its nearest neighbor, was sufficiently far from the other Patient's data that it could not be adequately simulated by our methodology.

Figure 13:
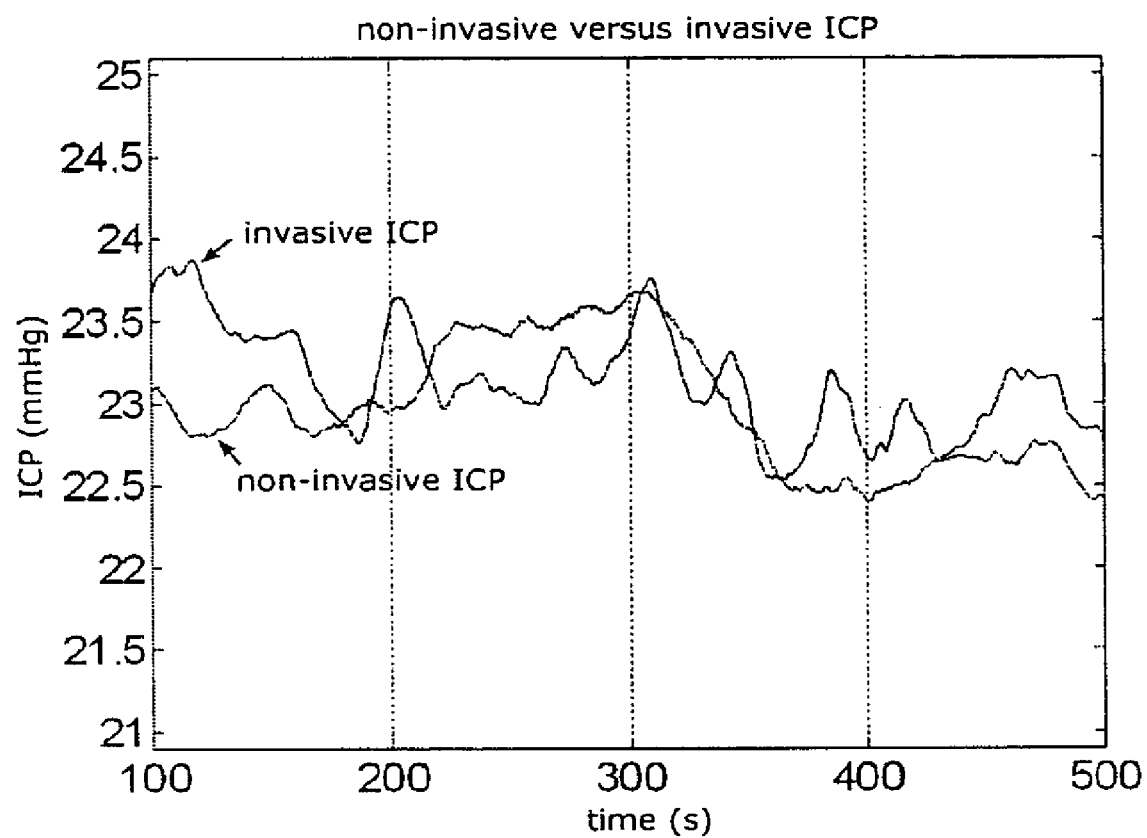
FIG. 13 shows traces of invasively measured (upper trace at left) and non-invasively measured (lower trace at left) ICP, averaged with a moving box-car filter on a one-minute time scale.

For clinical purposes, the methodology does not need to predict instantaneous ICP. Short-term mean ICP values, and/or ICP trends, are sufficient for patient management. Therefore, the predicted ICP values were averaged and compared with averages of the invasively measured ICP. When we averaged our time traces for Patient #4 with a one-minute running box-car filter, time traces of invasively measured ICP (upper trace at left) compared well with time traced of predicted ICP (lower trace at left), as shown in FIG. 13. With this minimal averaging, a point-by-point comparison of these time series shows that their values lie within 1 mmHg of one another, which is equivalent to the documented uncertainty in invasively measured ICP. In practical terms, to achieve this level of accuracy, the system would have to process one minute worth of data before making a prediction of ICP, which is a clinically acceptable situation.

The mean and variance of the differences between invasively measured and predicted ICP were examined as a function of different averaging lengths. As the averaging length increases, this difference, along with the variance, decreases. Our experimental observation was that a twenty second running average yielded a maximum variance that is within the documented uncertainty of the invasive ICP measurements and would therefore provide adequate reliability. The practical implication is that the first predicted ICP value will be available twenty seconds following initiation of collection and processing of the input data. After that, the system output is a predicted running mean of ICP with a time scale of twenty seconds. This is a clinically useful output.

EXAMPLE 2

ICP Prediction Results Based on Empirical Studies and Training and Validation of an ANN The prototype device described in Example 1 and the nICP determination methodology described in this specification was successfully tested on eighteen (18) patients at Harborview Medical Center in Seattle Wash., using blood pressure derived either directly from an arterial line or using arterial line-based ABP data simplified to mimic ABP data obtained from a blood-pressure cuff. A detailed description of the results for eight (8) of the eighteen patients was presented above in Example 1. Additional results are summarized below.

To determine the constants in the ICP prediction methodology, we acquired data from a set of patients (known as the 'training set') for whom we knew invasively measured ICP, as well as acoustic backscatter and ABP. For patients within the training set having a focal injury, their ICP was invasively measured from the same hemisphere as the injury focus, and the acoustic backscatter was measured from this side as well. This was a consideration because the brain, being a compartmentalized solid, can support pressure gradients across its structure. We then acquired data from another set of patients (the 'validation' set), whose members are independent of the first set, and on whom we tested our model. For these patients, invasive ICP devices and the acoustic backscatter measurements were also placed in and taken from the appropriate hemisphere. Acoustic backscatter data was used to derive MCA flow velocity using conventional Doppler techniques. All of the patients used in this study satisfied our inclusion criteria.

To test our methodology on the eighteen patients, we serially created empirical algorithms on seventeen of the eighteen 'training set' patients, where we allowed knowledge of acoustic backscatter, MCA flow velocity determinations derived from the acoustic backscatter, arterial blood pressure, and invasively measured ICP to determine the constants in our algorithm. We then used that methodology to determine nICP on the eighteenth 'validation set' patient, without exposing the algorithm to the invasively measured values of ICP and compared the invasively measured ICP to non-invasively determined ICP value. By doing this iteratively (once for each of the eighteen patients), we developed eighteen similar methodologies using seventeen 'training set' patients and one 'validation set' patient. We performed a one-minute running average of the ten-minute time series of ICP and nICP for each validation patient, then plotted the average and standard deviation of those invasively and non-invasively measured quantities.

Figure 14:
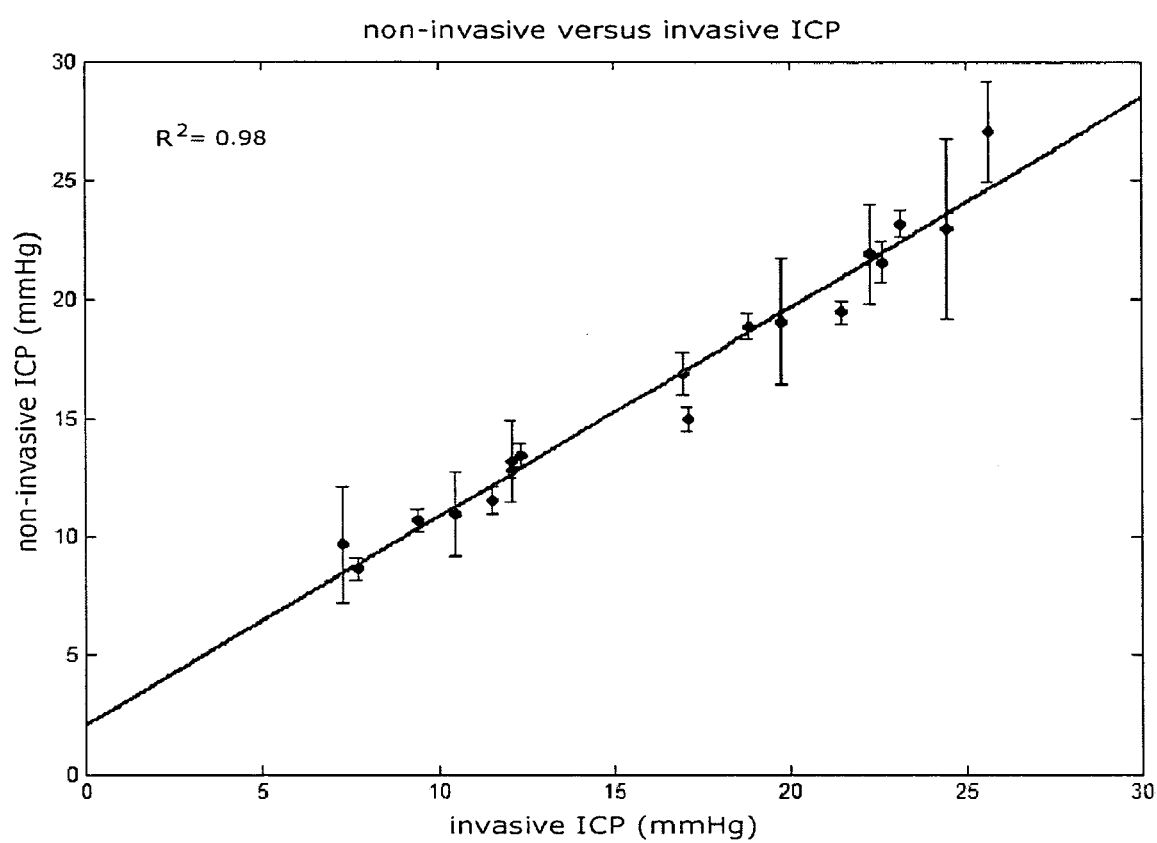
FIG. 14 shows the mean values for invasively measured ICP plotted against mean values for non-invasively determined ICP with data collected over a 10 minute period and subjected to a one minute running average.

We used ten minutes worth of data from each of our eighteen patients. We performed a one-minute running average on each of ICP and nICP (as in FIG. 13), then plotted the mean and variance of those results, using a version of the methodology based on continuous arterial blood pressure collected from an arterial line. The results are shown in FIG. 14, which demonstrates the feasibility of determining nICP using our novel analysis of acoustic backscatter from the brain collected using a trans-temporal approach, along with arterial blood pressure data captured using an arterial line. The mean of ICP is plotted against the mean of nICP collected over a ten-minute period, and subjected to a one-minute running average. The variance shown on the figure is that of the difference between actual, invasively measured ICP and predicted nICP after application of a one-minute running average.

In another analysis, we again used ten minutes worth of data from each of our eighteen patients. We performed a one-minute running average on each of actual, invasively measured ICP and predicted nICP and then plotted the mean and variance of those results. In this case, we used a version of the methodology based on invasively measured arterial line ABP data that has been simplified down to what one would expect to collect using a pressure cuff every one hundred seconds. This simulates the methodology of the present invention for predicting ICP based on V_mca data collected using non-invasive means and ABP measured using non-invasive means.

Figure 15:
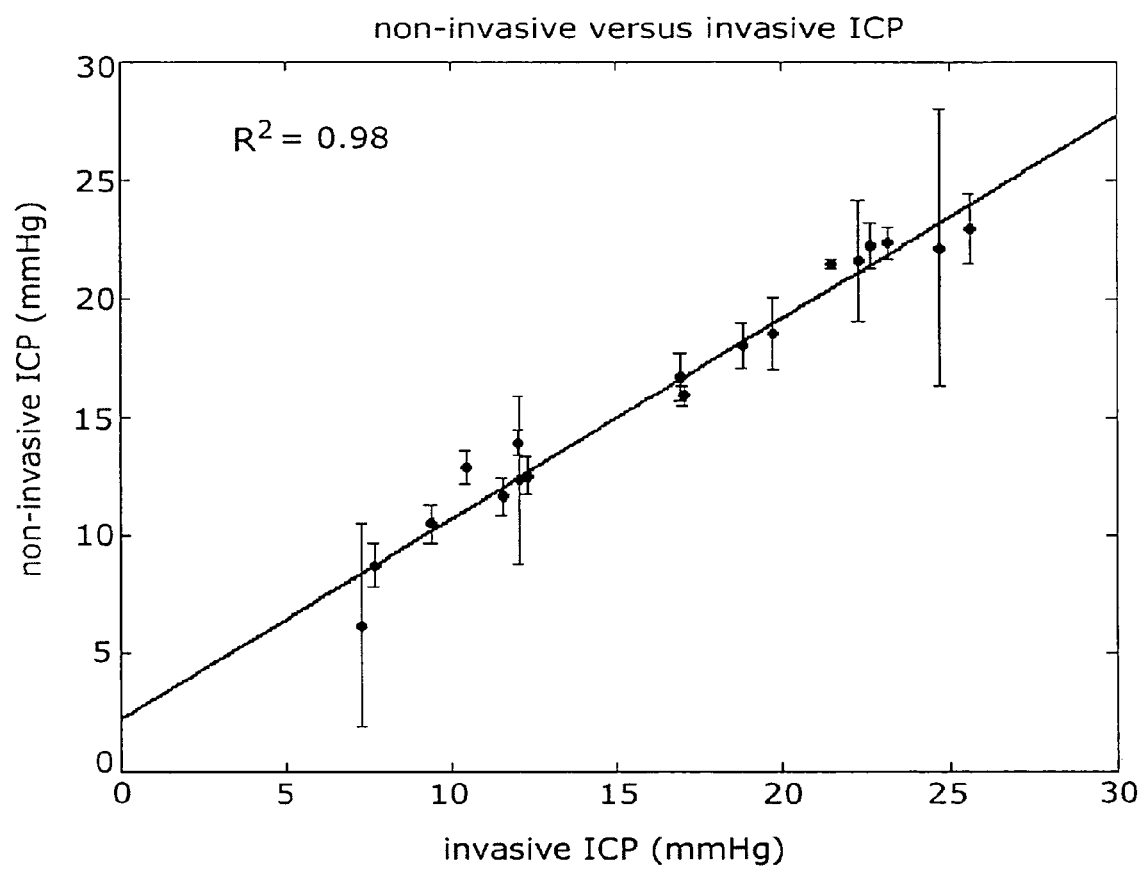
FIG. 15 shows the mean values for invasively measured ICP plotted against mean values for non-invasively determined ICP with data collected over a 10 minute period and subjected to a one minute running average.

FIG. 15 shows the results of this analysis and demonstrates the feasibility of determining ICP based on variables measured using non-invasive techniques and implementing novel analysis of acoustic backscatter from the brain collected, for example, in a trans-temporal approach, and arterial blood-pressure data captured initially using an arterial line and then decimated for determining and testing the methodology in a way to mimic what one could learn about arterial blood pressure from a standard arterial blood pressure cuff that was used every 100 seconds. The mean of actual, invasively measured ICP is plotted against the mean of predicted ICP determined over a ten-minute period, and subjected to a one-minute running average. The variance shown on the figure is that of the difference between actual, invasively measured ICP and predicted ICP calculated after application of a one-minute running average.

To further test our methodology, we collected invasively measured ICP from a larger "training set" of 29 patients, some of whom were included in the earlier 18 patient study. We also collected acoustic backscatter and ABP data (acquired from an arterial line) from the 29 patient set. Data was collected over a 5 to 20 minute period (depending on the patient) and subjected to a one-minute running average. For patients within the training set having a focal injury, ICP was invasively measured from the same hemisphere as the injury focus, and acoustic backscatter was measured from that side as well. A neural network was trained as described herein using the 29 patient training set and an algorithm for determining nICP (non-invasively measured ICP) using the acoustic backscatter and ABP data was formulated.

Figure 16:
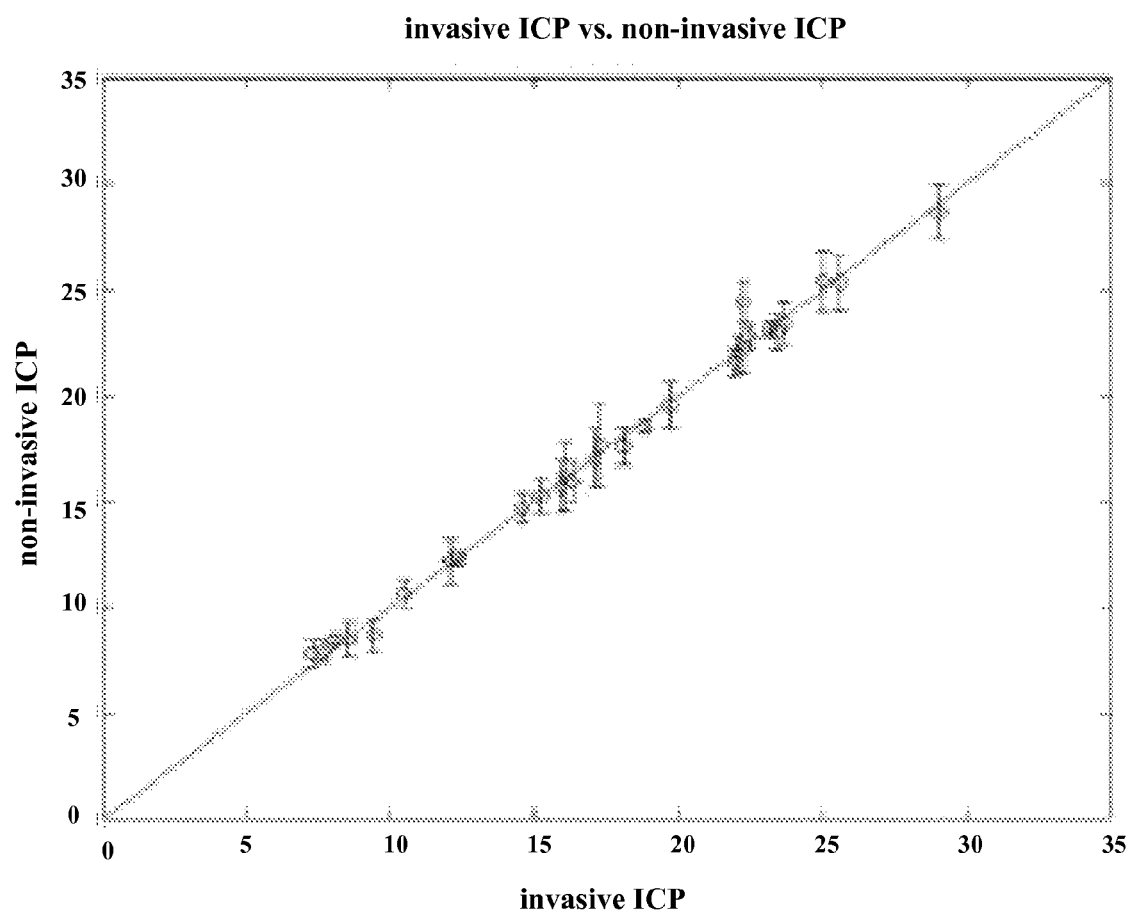
FIG. 16 shows application of an algorithm formulated using a neural network and a 29 patient training set to determine ICP for each of the 29 patient members of the training set using acoustic scatter and ABP data.

The algorithm formulated using the 29 patient training set with the neural network was then applied to the acoustic backscatter and ABP data for each of the 29 patients in the training set to determine nICP, and the non-invasively determined ICP was plotted against the invasively measured ICP. The results are shown in FIG. 16. The variance shown in FIG. 16 is that of the difference between (invasively measured) ICP and (non-invasively determined) nICP calculated after application of a one-minute running average. The (non-invasive) ICP determination algorithm was highly effective in determining ICP non-invasively using the acoustic backscatter and ABP data on the individual members in the training set over a broad range of ICP values of from less than 10 mm Hg to nearly 30 mm Hg.

Figure 17:
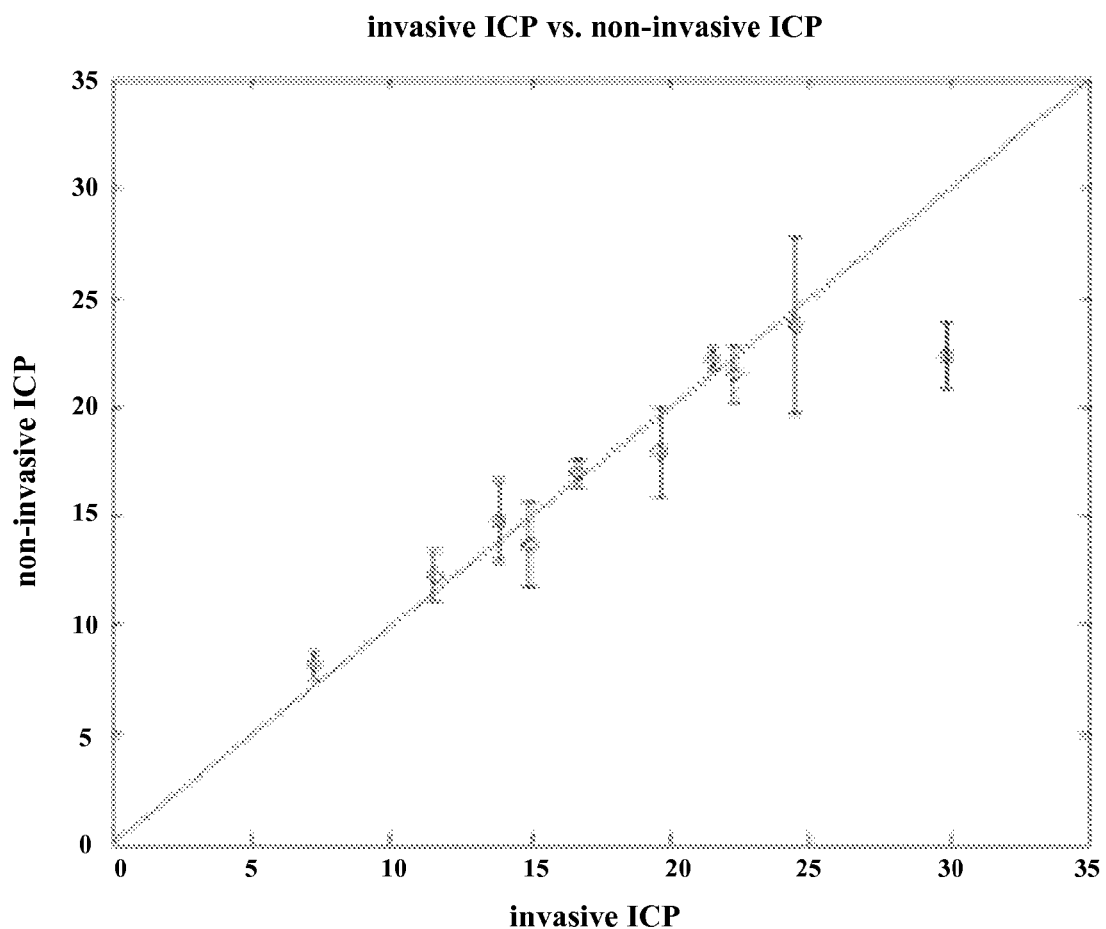
FIG. 17 shows application of the algorithm formulated using the 29 patient training set described above to the acoustic backscatter and ABP data for each of 10 patients that were not part of the 29 patient training group.

The algorithm formulated using the 29 patient training set as described above was then applied to the acoustic backscatter and ABP data for each of 10 patients that were not part of the 29 patient training group. Data was collected over a five to 20-minute period (depending on the patient) and subjected to a one-minute running average. The results are shown in FIG. 17. The variance shown is the figure is that of the difference between ICP and nICP calculated after application of a one-minute running average. The results demonstrate that the algorithm formulated using the 29 patient training set was effective in determining ICP non-invasively using the acoustic backscatter and ABP data on new patients over a broad range of ICP values.

EXAMPLE 3

Additional feasibility and efficacy testing of the methodology described above was performed using the experimental system described in Example 1. Acoustic backscatter, ABP and invasively measured ICP data was collected from a set of 25 patients (the 'training set'). For training set patients having a focal injury, the ICP was invasively measured from the same hemisphere as the injury focus and acoustic backscatter was measured from this hemisphere as well. The acoustic backscatter data was collected from the MCA and MCA flow velocity values were derived from the acoustic backscatter using conventional Doppler techniques. An empirical algorithm was derived using this data and the neural network training protocol described above.

Figure 18:
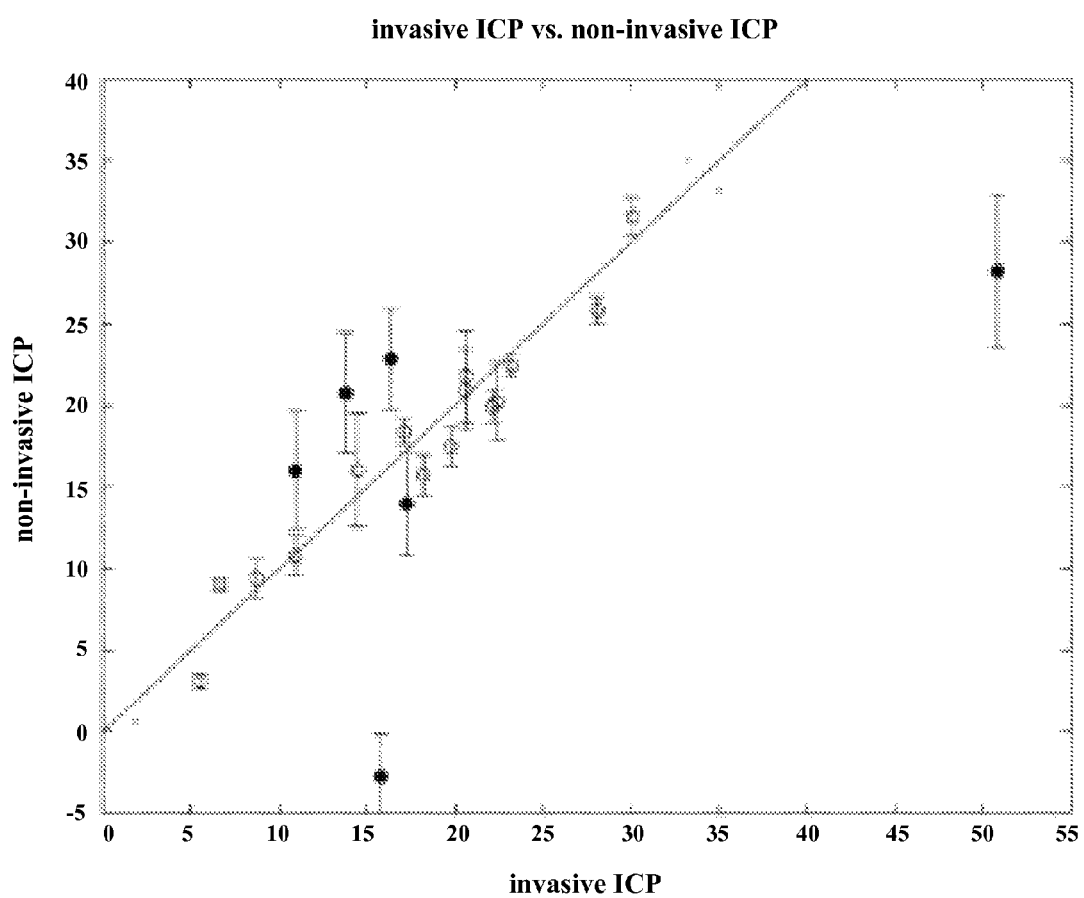
FIG. 18 illustrates application of an algorithm formulated using a neural network and acoustic scatter and ABP data from a 25 patient training set to determine ICP for each of 21 validation patients that were not part of the 25 patient training set.

The derived algorithm was then tested in an iterative fashion to determine ICP for 21 patients using only acoustic backscatter and ABP data for the 21 validation patients for whom invasively measured ICP data had also been collected. The results of this validation testing are illustrated in FIG. 18, which plots the non-invasively determined ICP against the invasively measured ICP for each of the 21 validation patients. The model algorithm provided a highly accurate determination of ICP using only the acoustic backscatter and ABP data for fifteen of the 21 patients, shown as open circle data points in FIG. 18. ICP determinations for six of the 21 validation patients fell outside the predetermined acceptability standards, although four of the six outlying data points may be within an acceptable error range. Using a larger patient population for derivation of the ICP algorithm is anticipated to eliminate substantially all outlying patient ICP determinations.

Figure 19:
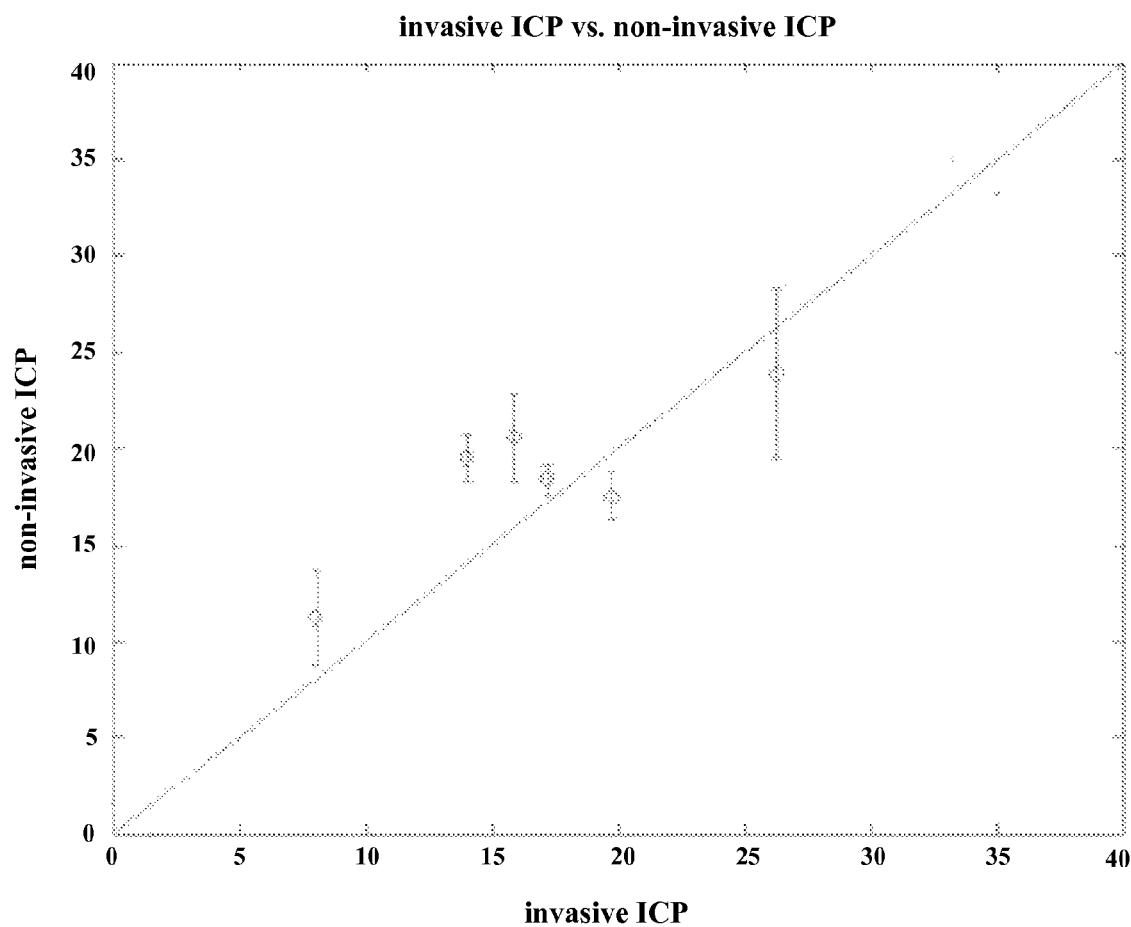
FIG. 19 illustrates application of an algorithm formulated using a neural network and acoustic scatter and ABP data from the 25 patient training set in an efficacy demonstration to determine ICP for each of 6 patients that were not part of the training or validation patient sets.

The model algorithm derived during the validation testing was tested for efficacy and shown to be efficacious in a 6 patient sample for whom invasively measured ICP data had also been collected. The non-invasively determined ICP is shown plotted against the invasively measured ICP for the 6 efficacy patients in FIG. 19. Data from four of the six patients produced ICP determinations within or very close to the predetermined acceptability standards; the two other patients would be within an error range that may be acceptable for some purposes. Using a larger patient population for derivation and validation of the ICP algorithm is anticipated to eliminate substantially all outlying patient ICP determinations.

We claim:

1. A method for determining ICP of a subject based on at least two variable inputs, comprising: acquiring acoustic data from a target site on a cranial blood vessel of the subject and using, as a first variable input, the acoustic data or a measurement derived from the acoustic data; acquiring, as a second variable input, arterial blood pressure (ABP) data; and determining ICP based on the first and second variable inputs using a non-linear relationship.

2. A method of claim 1, wherein the acoustic data is selected from the group consisting of: acoustic scatter and changes in acoustic scatter, including values of and changes in amplitude, phase and/or frequency of acoustic signals, values of and changes in length of scattered signals relative to the interrogation signal, values of and changes in the primary and/or other maxima and/or minima amplitudes of an acoustic signal within a cardiac and/or respiratory cycle; ratios of and changes in the ratios of the maximum and/or minimum amplitude to that of mean or variance or distribution of subsequent signals within a cardiac cycle, values of and changes in temporal or spatial variance of scattered or emitted signals at different times in the same target location and/or at the same time in different target locations, values of and rates of change of endogenous and/or induced brain tissue displacement or relaxation, acoustic emissions produced by the endogenous and/or induced brain tissue displacement or relaxation, and combinations thereof.

3. A method of claim 1, wherein the first variable input is acoustic scatter data.

4. A method of claim 1, wherein the first variable input is blood flow velocity in a cranial blood vessel.

5. A method of claim 1, wherein the first variable input is acquired using transcranial Doppler (TCD) techniques.

6. A method of claim 1, wherein ABP is measured non-invasively.

7. A method of claim 1, wherein ABP is measured using active and/or passive ultrasound techniques.

8. A method of claim 1, wherein ABP is measured using an active and/or passive ultrasound technique at a target site on a cranial blood vessel.

9. A method of claim 1, wherein the acoustic data is acquired from a first target site on a cranial blood vessel and data for determining ABP is acquired from a second CNS target site different from the first target site.

10. A method for determining ICP of a subject based on at least three variable inputs, comprising: acquiring acoustic data from a target site on or in a cranial blood vessel of the subject and using, as a first variable input, the acoustic data or a measurement derived from the acoustic data; acquiring, as a second variable input, arterial blood pressure (ABP) data; acquiring, as a third variable input, physiological data relating to a physiological property other than blood flow velocity and ABP; and determining ICP based on the first, second and third variable inputs using a non-linear relationship.

11. A method of claim 10, wherein the third variable input is selected from the group consisting of: CNS tissue stiffness, brain tissue displacement, partial pressure of at least one or more gases associated with brain respiration and metabolism, $pCO_2$, blood perfusion, hematocrit, EKG and electrophysiological properties.

12. A method of claim 1, wherein the acoustic data and ABP data are acquired by and processed in an integrated electronic device and are synchronous.

13. A method of claim 1, wherein the acoustic data and ABP data acquired are not synchronous, additionally comprising synchronizing the acoustic scatter and ABP data prior to determining ICP.

14. A method of claim 1, additionally comprising aligning the input variable data with respect to cardiac cycle boundaries prior to determining ICP.

15. A method of claim 1, wherein the ICP is derived using a non-linear, empirically derived relationship.

16. A method of claim 1, wherein the non-linear relationship of acoustic data and ABP data to ICP is derived using a neural network technique.

17. A method of claim 1, wherein the non-linear relationship of acoustic data and ABP data to ICP is derived using a first principles relationship.

18. A method of claim 1, wherein the non-linear relationship of acoustic data and ABP data to ICP is derived using a combined empirical/first principles approach, and the first principles approach is based on linear or non-linear relationships.

19. A method of claim 1, additionally comprising displaying at least one of acoustic data or a measurement derived from acoustic data and an image representing the target site.

20. A method of claim 1, additionally comprising scanning a CNS target area using at least one acoustic source/receiver array composed of multiple acoustic source and receiver elements; localizing a desired CNS target site within the CNS target area based on acoustic data acquired during scanning; and focusing one or more source and receiver elements on the desired CNS target site prior to collecting acoustic data.

21. A method of claim 1, wherein acoustic data is acquired using an acoustic transducer array.

22. A method of claim 1, wherein the ABP data is acquired from a target site on a cranial blood vessel of the subject.

23. A method of claim 22, wherein the target site for acquisition of the acoustic data and the target site for acquisition of the ABP data are on the same cranial blood vessel.

24. A method of claim 22, wherein the target site for acquisition of the acoustic data and the target site for acquisition of the ABP data is the middle cerebral artery (MCA).

25. A method of claim 1, wherein the target site for acquisition of the acoustic data and a target site for acquisition of the ABP data are different.

26. A method of claim 1, wherein there is a likelihood that 95% of the ICP values determined using the method are within 1.68 mmHg of an invasively measured ICP value.

27. A method of claim 1, wherein for seven of eight subjects for whom ICP determinations are made, the average value of instantaneous differences between ICP determined using the non-linear relationship between the first and second variables and ICP measured invasively is less than 2 mmHg.

28. A method of claim 1, wherein for 75% of subjects for whom ICP determinations are made, the average value of instantaneous differences between ICP determined using the non-linear relationship between the first and second variables and ICP measured invasively is less than 1 mmHg.

29. A method for determining intracranial pressure (ICP) of a subject based on at least two variable inputs, each variable input being acquired using non-invasive techniques, comprising:
acquiring acoustic data from a first target site on a cranial blood vessel of the subject and using, as a first variable input, the acoustic data or a measurement derived from the acoustic data;
acquiring a second variable input relating to one or more acoustic properties of a target CNS site, the second variable input being different from the first variable input and being selected from the group consisting of: acoustic scatter and changes in acoustic scatter, including values of and changes in amplitude, phase and/or frequency of acoustic signals, values of and changes in length of scattered signals relative to the interrogation signal, values of and changes in the primary and/or other maxima and/or minima amplitudes of an acoustic signal within a cardiac and/or respiratory cycle; ratios of and changes in the ratios of the maximum and/or minimum amplitude to that of mean or variance or distribution of subsequent signals within a cardiac cycle, values of and changes in temporal or spatial variance of scattered or emitted signals at different times in the same target location and/or at the same time in different target locations, values of and rates of change of endogenous and/or induced tissue displacement or relaxation, acoustic emissions produced by the endogenous and/or induced tissue displacement or relaxation, and combinations thereof; and
determining ICP based on the first and second variable inputs using a non-linear relationship.

30. A method of claim 29, wherein the target CNS site is different from the first target site on a cranial blood vessel.

31. A method of claim 29, wherein the first target site on a cranial blood vessel is the MCA or a carotid or a vertebral artery.

32. A method of claim 29, wherein the first variable input is acoustic scatter data.

33. A method of claim 32, wherein the second variable input is ABP.

34. A method of claim 33, wherein the ABP measured using active and/or passive acoustic techniques.

35. A method of claim 29, wherein the first variable input is acoustic scatter and the second variable input is CNS tissue displacement.

36. A method of claim 35, wherein the CNS tissue displacement is measured using active and/or passive acoustic techniques.

37. A method of claim 29, wherein the first variable input is acoustic scatter data acquired from a target site on a cranial blood vessel and the second variable input is acoustic scatter data acquired from one or more target CNS sites different from the target site on the cranial blood vessel.

38. A method of claim 29, wherein the first variable input is acoustic scatter, the second variable input is CNS tissue displacement, and additionally comprising acquiring ABP as a third variable input and determining ICP based on the first, second and third variable inputs.

39. A method for determining intracranial pressure (ICP) of a subject based on at least two variable inputs, comprising: locating and acoustically illuminating a desired target site in an automated fashion using an array comprising a plurality of acoustic source and/or detector elements by operating the array to acquire acoustic data from numerous sites within a larger target area, selecting at least one localized target site within the target area based on the acoustic data acquired for focused acoustic illumination and/or probing, and focusing the acoustic source and/or detector elements on the at least one selected localized target site and acquiring acoustic data from the at least one selected localized target site; using the acquired acoustic data from the at least one selected localized target site as a variable input; acquiring another variable input from acquired acoustic data or from an arterial blood pressure (ABP) measurement; and determining ICP based on the variable inputs using a non-linear relationship.

40. A method of claim 39, wherein selection of a localized target site is predetermined based on an acoustic property selected from the group consisting of: acoustic scatter data; Doppler analysis of acoustic scatter data, phase or frequency of acoustic scatter data; changes in the primary and/or other maxima and/or minima amplitude, phase or frequency of acoustic signals within a cardiac and/or respiratory cycle.

41. A method of claim 39, wherein selection of a localized target site is predetermined based on a determination derived from acoustic data selected from the group consisting of: flow velocity, tissue stiffness properties, endogenous and/or induced tissue displacement properties, acoustic emissions associated with tissue displacements, and rates of change of such properties.

42. A method of claim 39, wherein selection of the localized target site is determined based on the localized site of highest amplitude acoustic scatter.

43. A method of claim 39, wherein the selected localized target site is on the MCA.

* * * * *

UNITED STATES PATENT AND TRADEMARK OFFICE
CERTIFICATE OF CORRECTION

PATENT NO. : 7,547,283 B2  Page 1 of 1
APPLICATION NO. : 10/861197
DATED : June 16, 2009
INVENTOR(S) : Pierre Mourad et al.

It is certified that error appears in the above-identified patent and that said Letters Patent is hereby corrected as shown below:

| Col. No. | Line(s) | Edits |
|---|---|---|
| Title page | Item (73) | Please add: Assignee: "The University of Washington, Seattle, WA (US)" |

| Col. No. | Line(s) | Edits |
|---|---|---|
| 1 | 21 | Please replace the paragraph beginning at Column 1, line 21 with the following amended paragraph: "This invention was made with U.S. Government support under NS002234-03 awarded by the National Institutes of Health. The U.S. Government has certain rights in the invention." |

Signed and Sealed this

Tenth Day of August, 2010

David J. Kappos
*Director of the United States Patent and Trademark Office*